(12) United States Patent
Mao et al.

(10) Patent No.: US 10,752,928 B2
(45) Date of Patent: Aug. 25, 2020

(54) PRODUCTION OF NON-CALORIC SWEETENERS USING ENGINEERED WHOLE-CELL CATALYSTS

(71) Applicant: Conagen Inc., Bedford, MA (US)

(72) Inventors: Guohong Mao, Burlington, MA (US);
Jacob Edward Vick, Cambridge, MA (US); Shi-Yan Li, Bedford, MA (US);
Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 81 days.

(21) Appl. No.: 15/566,244

(22) PCT Filed: Apr. 14, 2016

(86) PCT No.: PCT/US2016/027458
§ 371 (c)(1),
(2) Date: Oct. 13, 2017

(87) PCT Pub. No.: WO2016/168413
PCT Pub. Date: Oct. 20, 2016

(65) Prior Publication Data
US 2018/0080055 A1    Mar. 22, 2018

Related U.S. Application Data

(60) Provisional application No. 62/147,160, filed on Apr. 14, 2015.

(51) Int. Cl.
| | | |
|---|---|---|
| C12N 9/10 | (2006.01) |
| C12P 19/56 | (2006.01) |
| C12N 15/52 | (2006.01) |
| A23L 27/30 | (2016.01) |

(52) U.S. Cl.
CPC .......... C12P 19/56 (2013.01); A23L 27/36 (2016.08); C12N 9/1048 (2013.01); C12N 9/1062 (2013.01); C12N 15/52 (2013.01); *A23V 2002/00* (2013.01)

(58) Field of Classification Search
None
See application file for complete search history.

(56) References Cited

U.S. PATENT DOCUMENTS

| | | |
|---|---|---|
| 9,107,436 B2 | 8/2015 | Purkayastha et al. |
| 9,522,929 B2 | 12/2016 | Mao et al. |
| 9,527,880 B2 | 12/2016 | Mao et al. |
| 9,567,619 B2 | 2/2017 | Mao et al. |
| 9,643,990 B2 | 5/2017 | Mao et al. |
| 9,765,104 B2 | 9/2017 | Mao et al. |
| 9,783,566 B2 | 10/2017 | Mao et al. |
| 9,850,270 B2 | 12/2017 | Mao et al. |
| 9,988,414 B2 | 6/2018 | Mao et al. |
| 10,138,263 B2 | 11/2018 | Mao et al. |
| 10,450,339 B2 | 10/2019 | Mao et al. |
| 2008/0148432 A1 | 6/2008 | Abad |
| 2009/0183270 A1 | 7/2009 | Adams et al. |
| 2014/0329281 A1 | 11/2014 | Houghton-Larson et al. |
| 2014/0357588 A1 | 12/2014 | Markosyan et al. |
| 2015/0315623 A1 | 11/2015 | Mao et al. |
| 2016/0095338 A1 | 4/2016 | Mao et al. |
| 2016/0097070 A1 | 4/2016 | Mao et al. |
| 2016/0097071 A1 | 4/2016 | Mao et al. |
| 2016/0097072 A1 | 4/2016 | Mao et al. |
| 2016/0153018 A1 | 6/2016 | Mao et al. |
| 2016/0207954 A1 | 7/2016 | Mao et al. |
| 2016/0208225 A1 | 7/2016 | Mao et al. |
| 2016/0208303 A1 | 7/2016 | Mao et al. |
| 2017/0181452 A1 | 6/2017 | Mao et al. |
| 2017/0196248 A1 | 7/2017 | Mao et al. |
| 2017/0218420 A1 | 8/2017 | Mao et al. |
| 2017/0218421 A1 | 8/2017 | Mao et al. |
| 2017/0362267 A1 | 12/2017 | Mao et al. |
| 2018/0009835 A1 | 1/2018 | Mao et al. |
| 2018/0037600 A1 | 2/2018 | Mao et al. |
| 2018/0051049 A1 | 2/2018 | Mao et al. |
| 2018/0244709 A1 | 8/2018 | Mao et al. |

FOREIGN PATENT DOCUMENTS

| | | |
|---|---|---|
| CN | 102559528 A | 7/2012 |
| CN | 102766667 A | 11/2012 |
| CN | 103397064 A | 11/2013 |
| CN | 104232496 A | 12/2014 |
| JP | H4-149191 A | 5/1992 |
| WO | WO 2002/010210 | 2/2002 |
| WO | WO 2011/028671 | 3/2011 |
| WO | WO 2011/097620 A1 | 8/2011 |
| WO | WO 2012/125991 | 9/2012 |
| WO | WO 2013/022989 | 2/2013 |

(Continued)

OTHER PUBLICATIONS

Coleman HD1, Ellis DD, Gilbert M, Mansfield SD, Up-regulation of sucrose synthase and UDP-glucose pyrophosphorylase impacts plant growth and metabolism. Plant Biotechnol J. Jan. 2006;4(1):87-101. (Year: 2006).*
Pieter P. Jacobs, Stefan Ryckaert, Steven Geysens, Kristof De Vusser, Nico Callewaert, Roland Contreras, Pichia surface display: display of proteins on the surface of glycoengineered Pichia pastoris strains, Biotechnol Lett (2008) 30:2173-2181 (Year: 2008).*
Uniprot accession No. F2DT21. May 31, 2011.
Zhang et al., Screening for glycosylphosphatidylinositol-modified cell wall proteins in Pichia pastoris and their recombinant expression on the cell surface. Appl Environ Microbiol. Sep. 2013;79(18):5519-26. doi: 10.1128/AEM.00824-13. Epub Jul. 8, 2013.

(Continued)

*Primary Examiner* — Mindy G Brown
(74) *Attorney, Agent, or Firm* — Wolf, Greenfield & Sacks, P.C.; Karen K. Chan

(57) ABSTRACT

Disclosed are whole-cell catalysts, methods of making the whole-cell catalysts, and methods of using the whole-cell catalysts to produce steviol glycosides.

25 Claims, 24 Drawing Sheets

Specification includes a Sequence Listing.

(56) References Cited

FOREIGN PATENT DOCUMENTS

| WO | WO 2013/093880 | 6/2013 |
|---|---|---|
| WO | WO 2013/093881 | 6/2013 |
| WO | WO 2013/096290 | 6/2013 |
| WO | WO 2013/096663 | 6/2013 |
| WO | WO 2013/110673 | 8/2013 |
| WO | WO 2013/176738 | 11/2013 |
| WO | WO 2014/122227 | 8/2014 |
| WO | WO 2014/193934 A | 12/2014 |
| WO | WO 2015/065650 A2 | 5/2015 |
| WO | WO 2015/171555 | 11/2015 |
| WO | WO 2016/054534 A1 | 4/2016 |

OTHER PUBLICATIONS

Bieniawska et al., Analysis of the sucrose synthase gene family in *Arabidopsis*. Plant J. Mar. 2007;49(5):810-28.

Bock, The UDP-glycosyltransferase (UGT) superfamily expressed in humans, insects and plants: Animal-plant arms-race and co-evolution. Biochem Pharmacol.Jan. 1, 2016;99:11-7. doi: 10.1016/j.bcp.2015.10.001. Epub Oct. 8, 2015.

Chaturvedula et al., NMR Spectral Analysis and Hyrdolysis Studies of Rebaudioside N, A Minor Steviol Glycoside of Stevia Rebaudiana Bertoni. Food and Nutrition Science. Oct. 2013; 4(10):1004-8.

Elleuche, Bringing functions together with fusion enzymes—from nature's inventions to biotechnological applications. Appl Microbiol Biotechnol. Feb. 2015;99(4):1545-56. doi: 10.1007/s00253-014-6315-1. Epub Dec. 24, 2014.

Hong et al., A cell plate-specific callose synthase and its interaction with phragmoplastin. Plant Cell. Apr. 2001;13(4):755-68.

Kim et al., Natural high potency sweeteners. Handbook of Sweeteners. S. Marie et al. (eds.). Springer Science +Business Media. New York. 1991;116-185.

Kraska et al., GRAS Assessment of Glucosylated Steviol Glycosides Steviten Rich Food Usage Conditions for General Recognition of Safety for Daepyung Co., Ltd. GRAS Notice (GRN) No. 448; Sep. 27, 2012; 63 pages.

Kubica et al., Determination of eight artificial sweeteners and common Stevia rebaudiana glycosides in non-alcoholic and alcoholic beverages by reversed-phase liquid chromatography coupled with tandem mass spectrometry. Anal Bioanal Chem. Feb. 2015;407(5):1505-12. doi: 10.1007/s00216-014-8355-x. Epub Dec. 4, 2014.

Martin et al., Expression of an *Arabidopsis* sucrose synthase gene indicates a role in metabolization of sucrose both during phloem loading and in sink organs. Plant J. Aug. 1993;4(2):367-77.

Masada et al., An efficient chemoenzymatic production of small molecule glucosides with in situ UDP-glucose recycling. FEBS Lett. May 29, 2007;581(13):2562-6.

Prakash et al., Bioconversion of rebaudioside I from rebaudioside A. Molecules. Oct. 28, 2014;19(11):17345-55. doi: 10.3390/molecules191117345.

Prakash et al., Catalytic hydrogenation of the sweet principles of Stevia rebaudiana, Rebaudioside B, Rebaudioside C, and Rebaudioside D and sensory evaluation of their reduced derivatives. Int J Mol Sci. Nov. 16, 2012;13(11):15126-36. doi: 10.3390/ijms131115126.

Prakash et al., Isolation and characterization of a novel rebaudioside M isomer from a bioconversion reaction of rebaudioside A and NMR comparison studies of rebaudioside M isolated from Stevia rebaudiana Bertoni and Stevia rebaudiana Morita. Biomolecules. Mar. 31, 2014;4(2):374-89. doi: 10.3390/biom4020374.

Prakash et al., Isolation and structure elucidation of rebaudioside D2 from bioconversion reaction of rebaudioside A to rebaudioside D. Nat Prod Commun. Aug. 2014;9(8):1135-8.

Reeck et al., "Homology" in proteins and nucleic acids: a terminology muddle and a way out of it. Cell. Aug. 28, 1987;50(5):667.

Son et al., Production of flavonoid o-glucoside using sucrose synthase and flavonoid o-glucosyltransferase fusion protein. J Microbiol Biotechnol. Jul. 2009;19(7):709-12.

Terasaka et al., In situ UDP-glucose regeneration unravels diverse functions of plant secondary product glycosyltransferases. FEBS Lett. Dec. 14, 2012;586(24):4344-50. doi: 10.1016/j.febslet.2012.10.045.

UniprotKB accession No. B8AQD6_ORYSI. Mar. 3, 2009. Yu et al.

UniprotKB accession No. P49040. Feb. 1, 1996. Martin et al.

Zheng et al., The structure of sucrose synthase-1 from *Arabidopsis thaliana* and its functional implications. J Biol Chem. Oct. 14, 2011;286(41):36108-18. doi: 10.1074/jbc.M111.275974. Epub Aug. 24, 2011.

U.S. Appl. No. 15/701,599, filed Sep. 12, 2017, Mao et al.

U.S. Appl. No. 15/701,613, filed Sep. 12, 2017, Mao et al.

\* cited by examiner

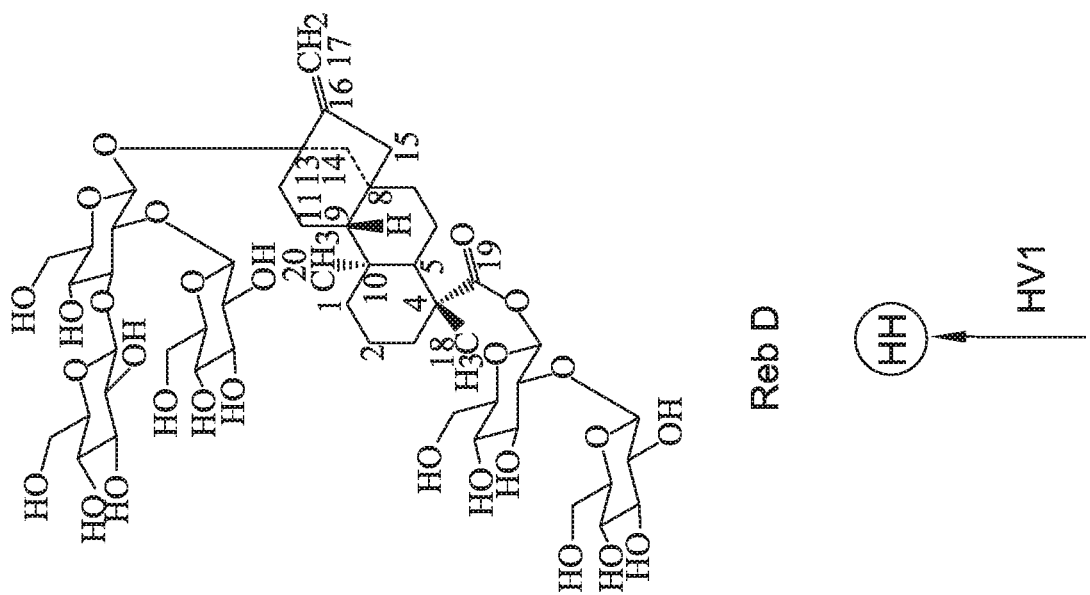
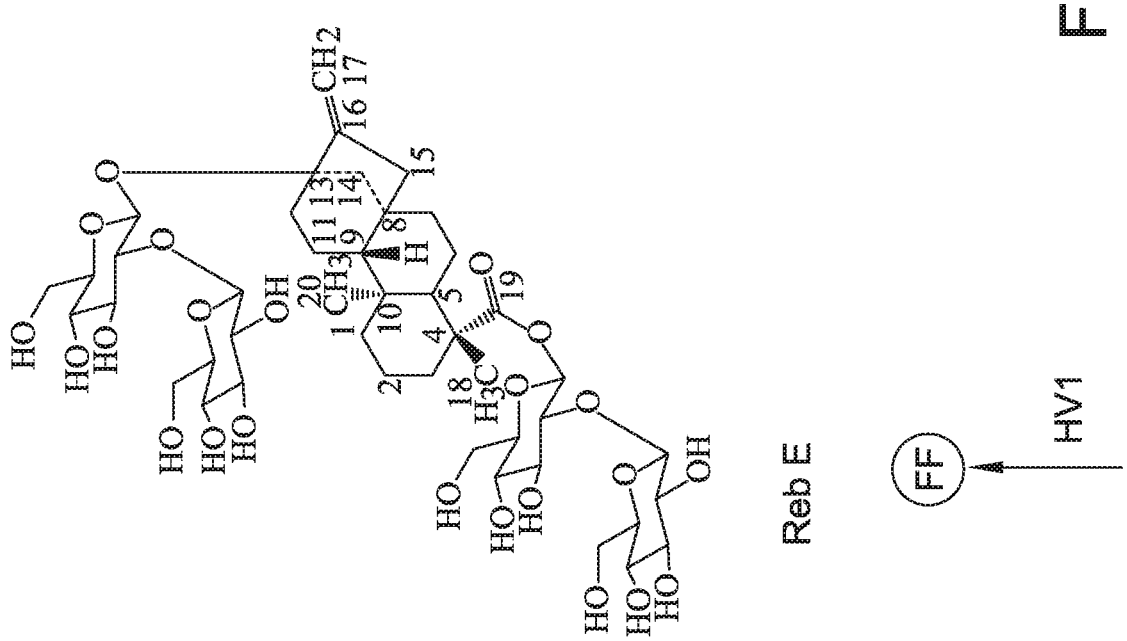
FIG. 1D

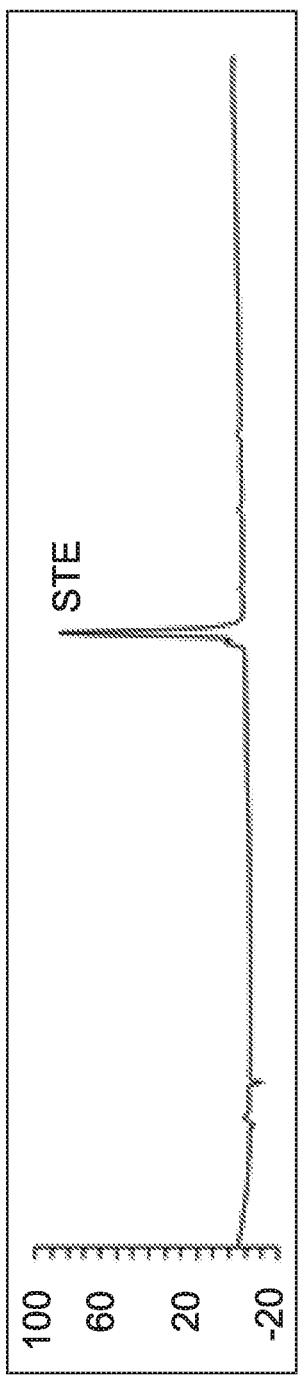
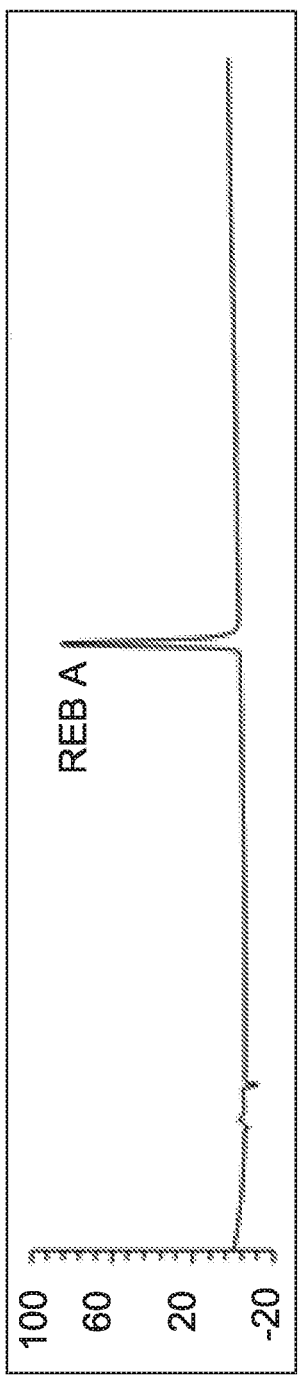
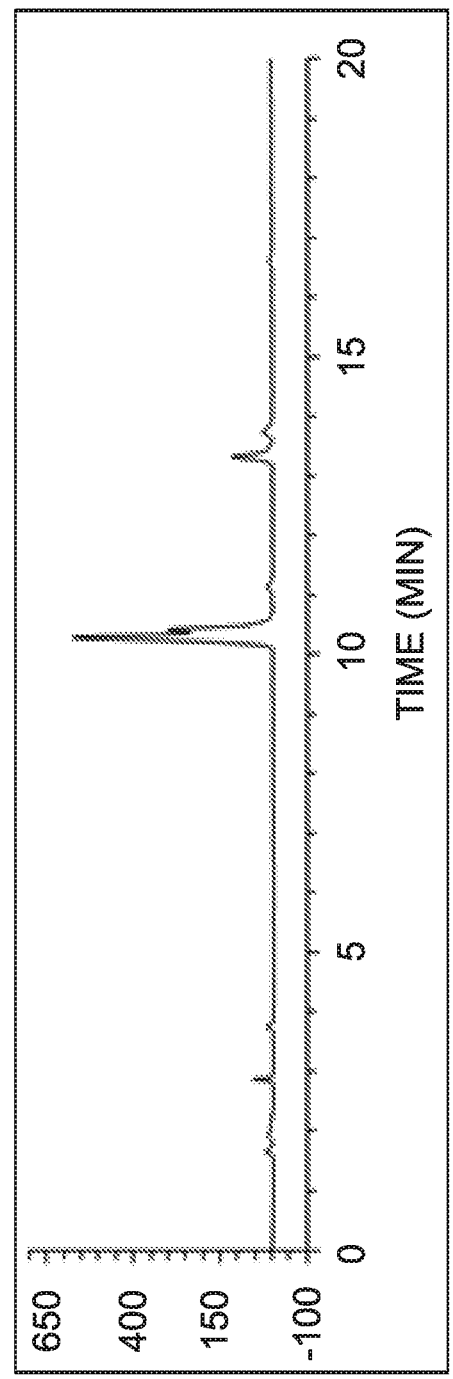
FIG. 2A
FIG. 2B
FIG. 2C

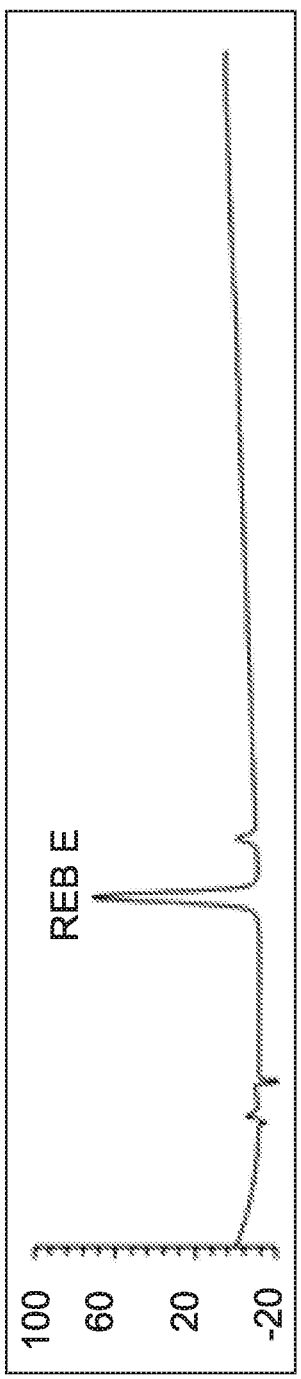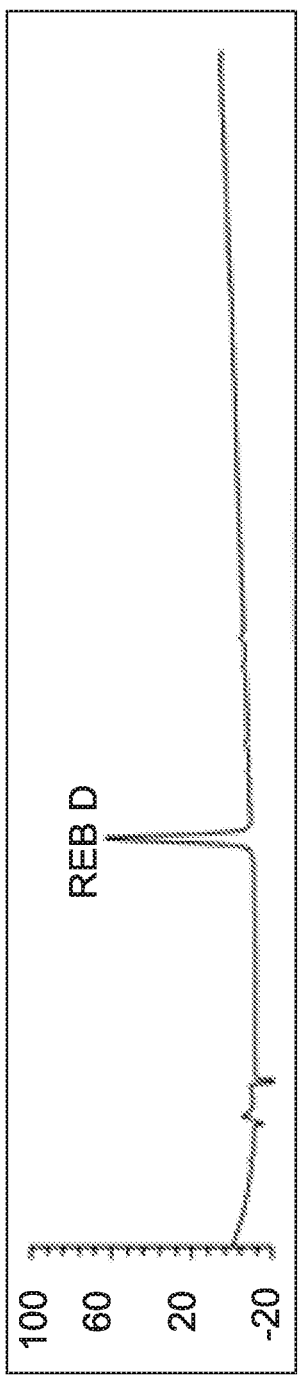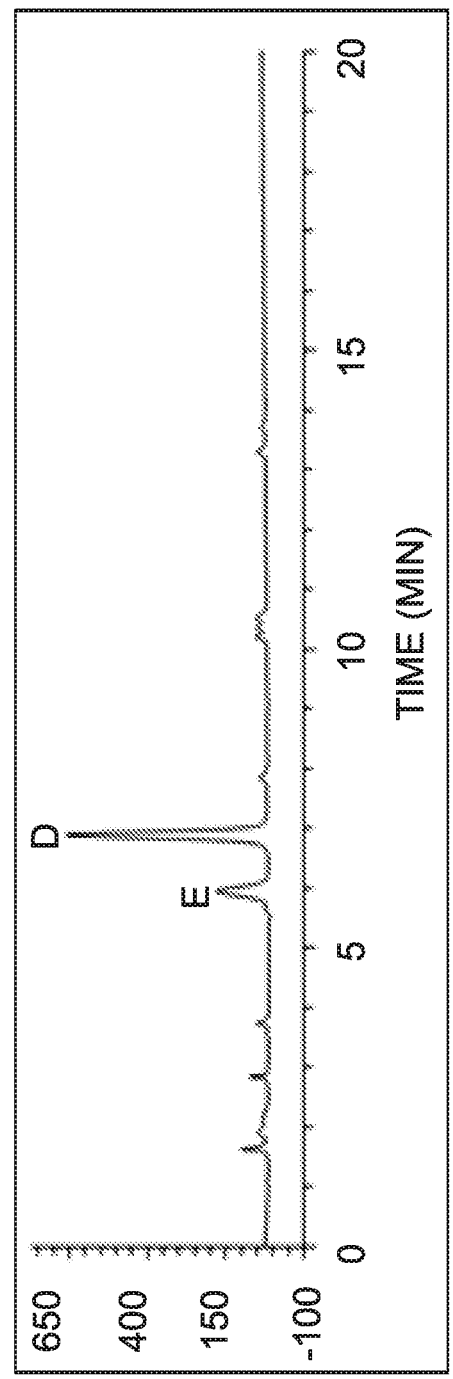

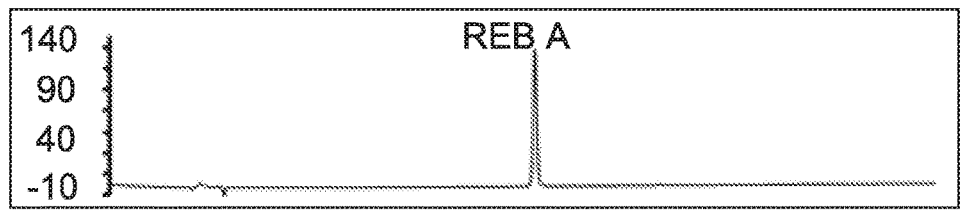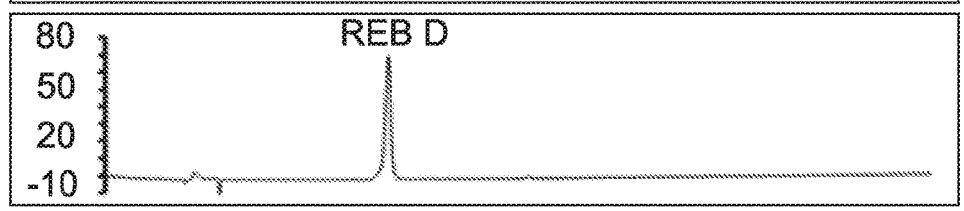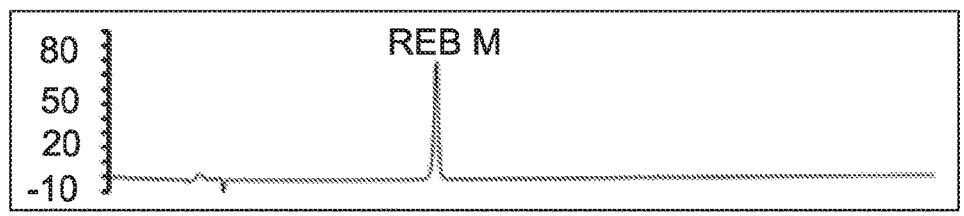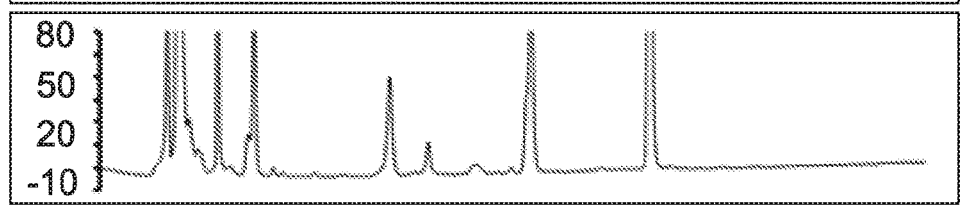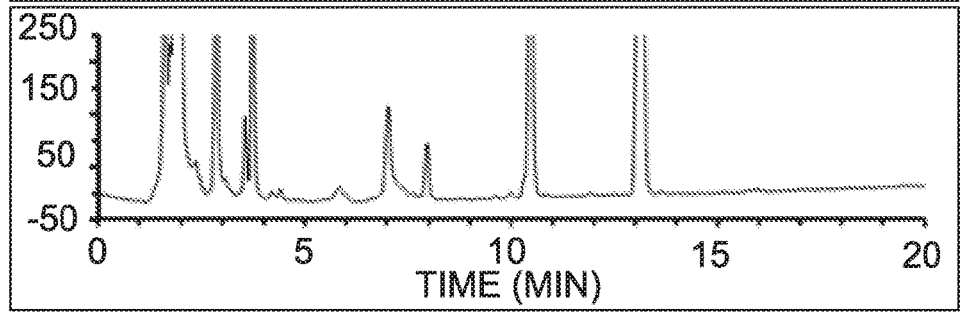

PRODUCTION OF NON-CALORIC SWEETENERS USING ENGINEERED WHOLE-CELL CATALYSTS

RELATED APPLICATIONS

This application is a National Stage Application under 35 U.S.C. § 371 of International PCT Application No. PCT/US2016/027458, filed Apr. 14, 2016, and entitled "PRODUCTION OF NON-CALORIC SWEETENERS USING ENGINEERED WHOLE-CELL CATALYSTS", which claims the benefit under 35 U.S.C. § 119(e) of U.S. Provisional Application Ser. No. U.S. 62/147,160, filed on Apr. 14, 2015, and entitled "PRODUCTION OF NON-CALORIC SWEETENERS USING ENGINEERED WHOLE-CELL CATALYSTS," the contents of each of which are herein incorporated by reference in their entirety.

Statement in Support for Filing a Sequence Listing

A computer readable form of the Sequence Listing, a text file named "C149770014US01-SEQLIST-AM.txt", which is 36,388 bytes in size (as measured in MICROSOFT WINDOWS® EXPLORER), is filed concurrently herewith via EFS-Web and is herein incorporated by reference. This Sequence Listing consists of SEQ ID NOs:1-12.

BACKGROUND OF THE DISCLOSURE

The present disclosure relates generally to natural sweeteners. More particularly, the present disclosure relates to a non-caloric sweetener and methods for synthesizing the non-caloric sweetener.

Steviol glycosides are natural products isolated from *Stevia rebaudiana* leaves. Steviol glycosides are widely used as high intensity, low-calorie sweeteners and are significantly sweeter than sucrose. As natural sweeteners, different steviol glucosides have different degrees of sweetness and after-taste. The sweetness of steviol glycosides is significantly higher than that of sucrose. For example, stevioside is 100-150 times sweeter than sucrose with bitter after-taste. Rebaudioside C is between 40-60 times sweeter than sucrose. Dulcoside A is about 30 times sweeter than sucrose.

Naturally occurring steviol glycosides share the same basic steviol structure, but differ in the content of carbohydrate residues (e.g., glucose, rhamnose and xylose residues) at the C13 and C19 positions. Steviol glycosides with known structures include, steviol, stevioside, rebaudioside A, rebaudioside B, rebaudioside C, rebaudioside D, rebaudioside E, rebaudioside F and dulcoside A (see e.g., Table 1). Other steviol glycosides are rebaudioside M, rebaudioside N and rebaudioside O.

TABLE 1

| Name | Structure | Molecular Formula | Molecular Weight |
|---|---|---|---|
| Steviol | 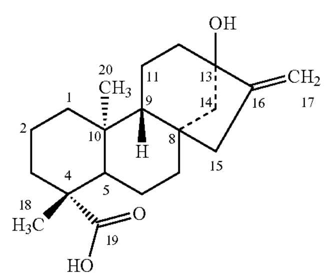 | $C_{20}H_{30}O_3$ | 318 |
| Stevioside | 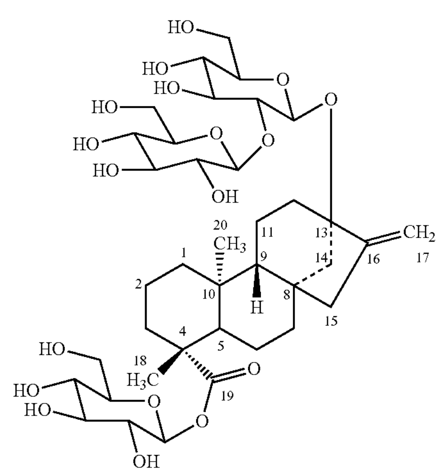 | $C_{38}H_{60}O_{18}$ | 804 |

TABLE 1-continued
Steviol glycosides.
| Name | Structure | Molecular Formula | Molecular Weight |
|---|---|---|---|
| Rebaudioside A | 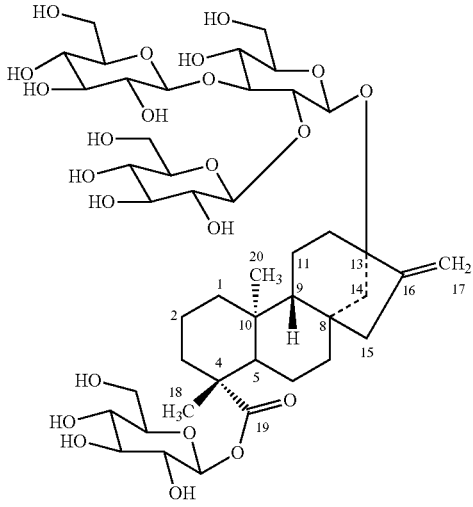 | $C_{44}H_{70}O_{23}$ | 966 |
| Rebaudioside-B | 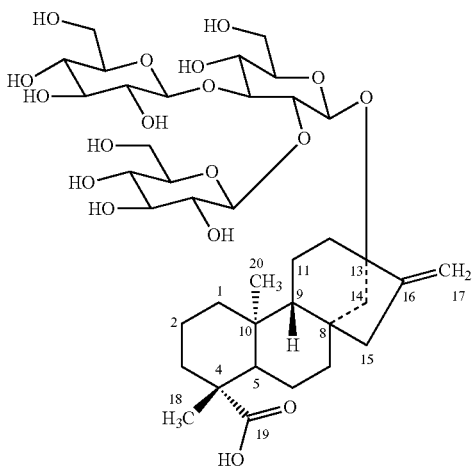 | $C_{38}H_{60}O_{18}$ | 804 |

TABLE 1-continued
Steviol glycosides.
| Name | Structure | Molecular Formula | Molecular Weight |
|---|---|---|---|
| Rebaudioside C | 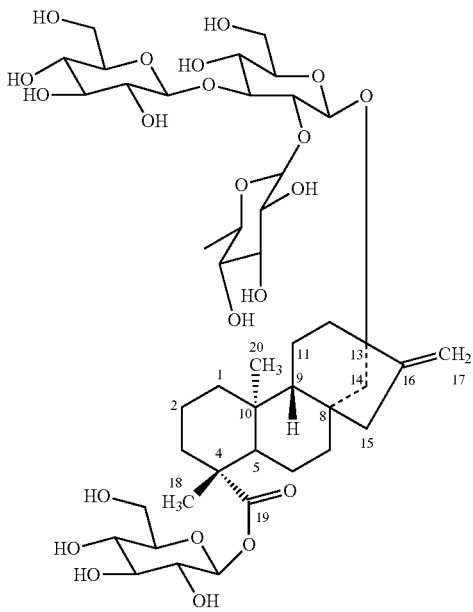 | $C_{44}H_{70}O_{22}$ | 950 |
| Rebaudioside D | 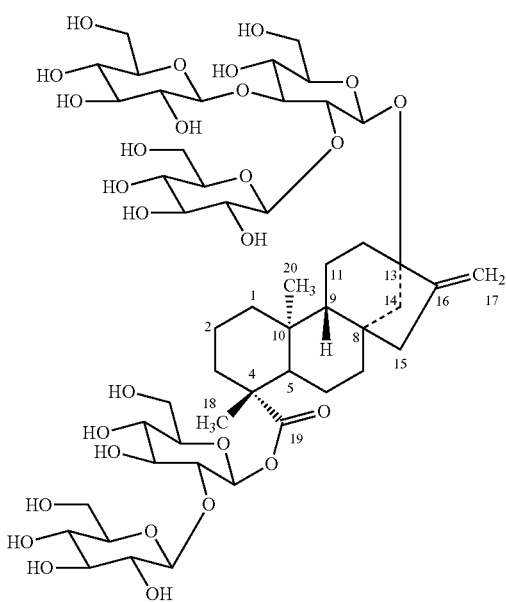 | $C_{50}H_{80}O_{28}$ | 1128 |

TABLE 1-continued

Steviol glycosides.

| Name | Structure | Molecular Formula | Molecular Weight |
|---|---|---|---|
| Rebaudioside E | 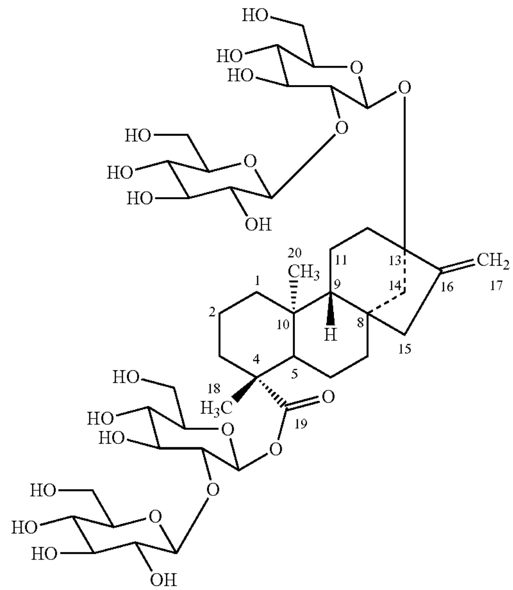 | $C_{44}H_{70}O_{23}$ | 966 |
| Rebaudioside F | 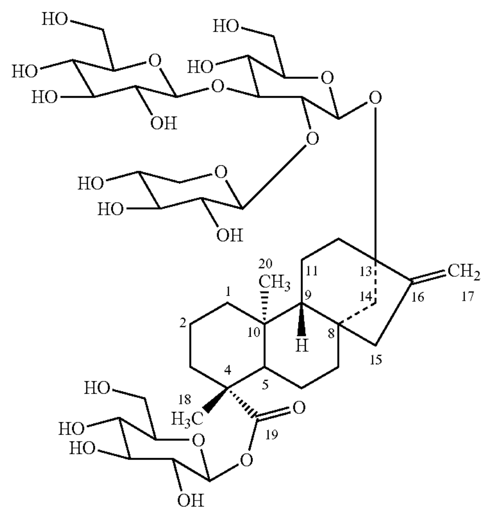 | $C_{43}H_{68}O_{22}$ | 936 |
| Rebaudioside G | 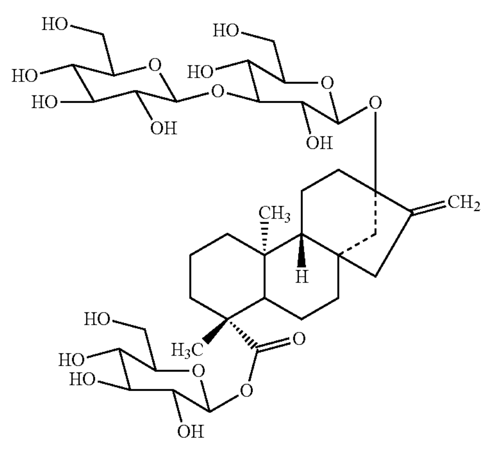 | $C_{38}H_{60}O_{18}$ | 804 |

TABLE 1-continued
Steviol glycosides.
| Name | Structure | Molecular Formula | Molecular Weight |
|---|---|---|---|
| Rebaudioside KA | 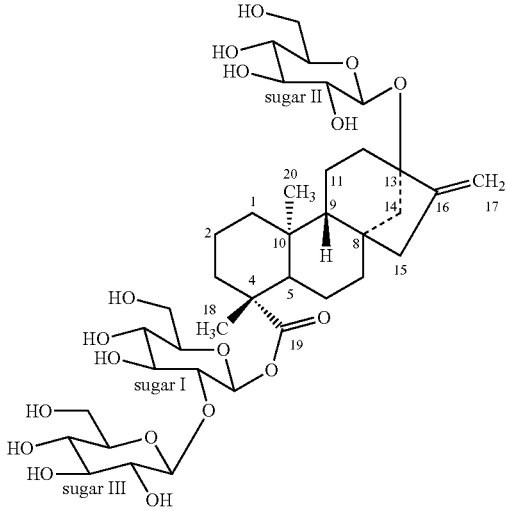 | $C_{38}H_{60}O_{18}$ | 804 |
| Dulcoside A | 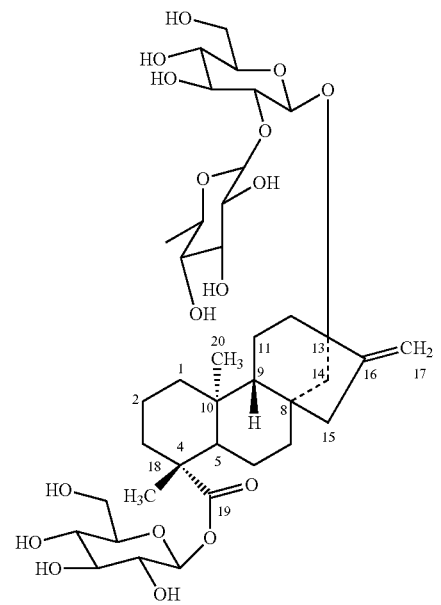 | $C_{38}H_{60}O_{17}$ | 788 |

TABLE 1-continued

Steviol glycosides.

| Name | Structure | Molecular Formula | Molecular Weight |
|---|---|---|---|
| (13-[(2-O-β-D-glucopyranosyl-3-O-β-D-glucopyranosyl-β-D-glucopyranosyl)oxy]ent-kaur-16-en-19-oic acid [(2-O-β-D-glucopyranosyl-3-O-β-D-glucopyranosyl-β-D-glucopyranosyl) ester] Rebaudioside M | (structure) | $C_{56}H_{90}O_{33}$ | 1290 |

On a dry weight basis, stevioside, rebaudioside A, rebaudioside C, and dulcoside A, account for 9.1, 3.8, 0.6, and 0.3% of the total weight of the steviol glycosides in the leaves, respectively, while the other steviol glycosides are present in much lower amounts. Extracts from the *Stevia rebaudiana* plant are commercially available, which typically contain stevioside and rebaudioside A as primary compounds. The other steviol glycosides typically are present in the stevia extract as minor components. For example, the amount of rebaudioside A in commercial preparations can vary from about 20% to more than 90% of the total steviol glycoside content, while the amount of rebaudioside B can be about 1-2%, the amount of rebaudioside C can be about 7-15%, and the amount of rebaudioside D can be about 2% of the total steviol glycosides.

The majority of steviol glycosides are formed by several glycosylation reactions of steviol, which are typically catalyzed by the UDP-glycosyltransferases (UGTs) using uridine 5'-diphosphoglucose (UDP-glucose) as a donor of the sugar moiety, as illustrated in FIGS. 1A, 1B, 1C, 1D, and 1E. UGTs in plants make up a very diverse group of enzymes that transfer a glucose residue from UDP-glucose to steviol. For example, glycosylation of the C-3' of the C-13-O-glucose of stevioside yields rebaudioside A; and glycosylation of the C-2' of the 19-O-glucose of the stevioside yields rebaudioside E. Further glycosylation of rebaudioside A (at C-2'-19-O-glucose) or rebaudioside E (at C-3'-13-O-glucose) produces rebaudioside D. Glycosylation of rebaudioside D (at C-3'-19-O-glucose) produces rebaudioside M.

Alternative sweeteners are receiving increasing attention due to awareness of many diseases in conjunction with the consumption of high-sugar foods and beverages. Although artificial sweeteners are available, many artificial sweeteners such as dulcin, sodium cyclamate and saccharin have been banned or restricted by some countries due to concerns over their safety. Therefore, non-caloric sweeteners of natural origin are becoming increasingly popular. One of the main obstacles for the widespread use of stevia sweeteners are their undesirable taste attributes. Accordingly, there exists a need to develop alternative sweeteners and methods for their production to provide the best combination of sweetness potency and flavor profile.

SUMMARY OF THE DISCLOSURE

The present disclosure relates generally to natural sweeteners. More particularly, the present disclosure relates to non-caloric sweeteners and methods for synthesizing the non-caloric natural sweeteners.

Whole-Cell Catalyst.

In one aspect, the present disclosure is directed to at least one whole-cell catalyst. In this aspect, the at least one whole-cell catalyst is a transformed host cell that includes at least one nucleotide sequence encoding at least one enzyme including, but not limited to, a uridine diphospho glycosyltransferase (UDP-glycosyltransferase) and a sucrose synthase (SUS). Non-limiting examples of suitable uridine diphospho glycosyltransferases include: UGT76G1, HV1, EUGT11, and any combination thereof.

In this aspect, the transformed host cell may be any suitable host cell transformed by at least one expression cassette that includes at least one nucleotide sequence encoding the at least one enzyme. Non-limiting examples of suitable host cells include bacteria, yeast, filamentous fungi, cyanobacteria algae, and plant cells. In an aspect, the at least one expression cassette is selected for compatibility with the host cell type, and the codons within the at least one nucleotide sequence encoding the at least one enzyme may be subjected to codon-optimization using known methods in order to enhance expression of the at least one enzyme within the selected host cell type.

Method of Synthesizing Steviol Glycosides.

In another aspect, the at least one whole-cell catalyst may be used in a method of synthesizing at least one steviol glycoside as described herein. The method includes culturing the at least one whole-cell catalyst in vitro within a culture medium that includes a substrate. Without being limited to any particular theory, the at least one enzyme produced from the at least one expression cassette within the transformed host cell enzymatically glycosylates the substrate within the culture medium to synthesize the desired at least one steviol glycoside.

Whole-Cell Catalyst *Pichia pastoris* Strains.

In another aspect, the present disclosure is directed to a whole-cell catalyst that includes a *Pichia pastoris* host cell transformed by at least one expression cassette containing at least one nucleotide sequence including: a first nucleotide sequence encoding a fusion protein that includes a first nucleotide segment encoding a *Pichia* cell wall protein inserted in frame to the C-terminal of a second nucleotide segment encoding a UDP-glycosyltransferase; and a second nucleotide sequence encoding a sucrose synthase. The at least one nucleotide sequence of the transformed *Pichia pastoris* cell may be expressed to produce the whole-cell catalyst characterized by an amount of UDP-glycosyltransferase displayed on the cell surface of the *Pichia pastoris* cell and an amount of intracellular sucrose synthase.

The transformed *Pichia pastoris* may include one or more copies of each of the at least one nucleotide sequences in an aspect. A first *Pichia pastoris* strain (G/K4S2) includes: four copies of the expression cassette containing the first nucleotide sequence including the *Pichia* cell wall protein (GCW61) inserted in frame to the C-terminal of the second nucleotide segment encoding a UDP-glycosyltransferase (UGT76G1); and two copies of the expression cassette containing the second nucleotide sequence encoding a sucrose synthase (mbSUS1). A second *Pichia pastoris* strain (G/H5S2) includes: five copies of the expression cassette containing the first nucleotide sequence including the *Pichia* cell wall protein (GCW61) inserted in frame to the C-terminal of the second nucleotide segment encoding a UDP-glycosyltransferase (HV1); and two copies of the expression cassette containing the second nucleotide sequence encoding a sucrose synthase (mbSUS1).

Method of Producing Rebaudioside A from Stevioside.

In another aspect, the present disclosure is directed to a method for synthesizing rebaudioside A from stevioside. The method includes culturing a whole-cell catalyst with a culture medium including a stevioside substrate for a sufficient time to produce rebaudioside A, wherein a glucose is covalently coupled to the stevioside to produce the rebaudioside A. The whole-cell catalyst is a transformed host cell expressing an amount of UDP-glycosyltransferase (UGT76G1) and an amount of sucrose synthase (mbSUS1). In an aspect, the whole-cell catalyst may be the G/K4S2 strain of *Pichia pastoris* and the culture medium may further include: potassium phosphate buffer, MgCl$_2$, sucrose, UDP-glucose, UDP, and any combination thereof.

Method of Producing Rebaudioside M from Rebaudioside D.

In another aspect, the present disclosure is directed to a method for synthesizing rebaudioside M from rebaudioside D. The method includes culturing a whole-cell catalyst with a culture medium including a rebaudioside D substrate for a sufficient time to produce rebaudioside M, wherein a glucose is covalently coupled to the rebaudioside D to produce the rebaudioside M. The whole-cell catalyst is a transformed host cell expressing an amount of UDP-glycosyltransferase (UGT76G1) and an amount of sucrose synthase (mbSUS1). In an aspect, the whole-cell catalyst may be the G/K4S2 strain of *Pichia pastoris* and the culture medium may further include: potassium phosphate buffer, MgCl$_2$, sucrose, UDP-glucose, UDP, and any combination thereof.

Method of Producing Rebaudioside D from Rebaudioside E.

In another aspect, the present disclosure is directed to a method for synthesizing rebaudioside D from rebaudioside E. The method includes culturing a whole-cell catalyst with a culture medium including a rebaudioside E substrate for a sufficient time to produce rebaudioside D, wherein a glucose is covalently coupled to the rebaudioside E to produce the rebaudioside D. The whole-cell catalyst is a transformed host cell expressing an amount of UDP-glycosyltransferase (UGT76G1) and an amount of sucrose synthase (mbSUS1). In an aspect, the whole-cell catalyst may be the G/K4S2 strain of *Pichia pastoris* and the culture medium may further include: potassium phosphate buffer, MgCl$_2$, sucrose, UDP-glucose, UDP, and any combination thereof.

Method of Producing Rebaudioside D from Rebaudioside A.

In another aspect, the present disclosure is directed to a method for synthesizing rebaudioside D from rebaudioside A. The method includes culturing a whole-cell catalyst with a culture medium including a rebaudioside A substrate for a sufficient time to produce rebaudioside D, wherein a glucose is covalently coupled to the rebaudioside A to produce the rebaudioside D. The whole-cell catalyst is a transformed host cell expressing an amount of UDP-glycosyltransferase (HV1-GCW61) and an amount of sucrose synthase (mbSUS1). In an aspect, the whole-cell catalyst may be the G/H5S2 strain of *Pichia pastoris* and the culture medium may further include: potassium phosphate buffer, MgCl$_2$, sucrose, UDP-glucose, UDP, and any combination thereof.

Method of Producing Rebaudioside E from Stevioside.

In another aspect, the present disclosure is directed to a method for synthesizing rebaudioside E from a stevioside substrate. The method includes culturing a whole-cell catalyst with a culture medium including a stevioside substrate for a sufficient time to produce rebaudioside E, wherein a glucose is covalently coupled to the stevioside to produce the rebaudioside E. The whole-cell catalyst is a transformed host cell expressing an amount of UDP-glycosyltransferase (HV1-GCW61) and an amount of sucrose synthase (mbSUS1). In an aspect, the whole-cell catalyst may be the G/H5S2 strain of *Pichia pastoris* and the culture medium may further include: potassium phosphate buffer, MgCl$_2$, sucrose, UDP-glucose, UDP, and any combination thereof.

Method of Producing Rebaudioside M from Stevioside and/or Rebaudioside A.

In another aspect, the present disclosure is directed to a method for synthesizing rebaudioside M from stevioside and/or rebaudioside A. The method includes culturing a whole-cell catalyst with a culture medium including a stevioside and/or rebaudioside A substrate for a sufficient time to produce rebaudioside M. The whole-cell catalyst includes: a first transformed host cell expressing an amount of UDP-glycosyltransferase (UGT76G1) and an amount of sucrose synthase (mbSUS1); and a second transformed host cell expressing an amount of UDP-glycosyltransferase (HV1-GCW61) and an amount of sucrose synthase (mbSUS1). In an aspect, the whole-cell catalyst may be the G/K4S2 and G/H5S2 strains of *Pichia pastoris* and the culture medium may further include: potassium phosphate buffer, MgCl$_2$, sucrose, UDP-glucose, UDP, and any combination thereof.

Method of Producing Rebaudioside E from Rebaudioside KA.

In another aspect, the present disclosure is directed to a method for synthesizing rebaudioside E from rebaudioside KA. The method includes culturing a whole-cell catalyst with a culture medium including a rebaudioside KA substrate for a sufficient time to produce rebaudioside E, wherein a glucose is covalently coupled to the rebaudioside KA to produce the rebaudioside E. The whole-cell catalyst is a transformed host cell expressing an amount of UDP-glycosyltransferase (HV1-GCW61) and an amount of sucrose synthase (mbSUS1). In an aspect, the whole-cell catalyst may be the G/H5S2 strain of Pichia pastoris and the culture medium may further include: potassium phosphate buffer, $MgCl_2$, sucrose, UDP-glucose, UDP, and any combination thereof.

Method of Producing Rebaudioside KA and Rebaudioside E from Rubusoside.

In another aspect, the present disclosure is directed to a method for synthesizing rebaudioside KA from rubusoside. The method includes culturing a whole-cell catalyst with a culture medium including a rubusoside substrate for a sufficient time to produce rebaudioside KA, wherein a glucose is covalently coupled to the rubusoside to produce the rebaudioside KA, continually a glucose is covalently coupled to the rebaudioside KA to produce the rebaudioside E. The whole-cell catalyst is a transformed host cell expressing an amount of UDP-glycosyltransferase (HV1-GCW61) and an amount of sucrose synthase (mbSUS1). In an aspect, the whole-cell catalyst may be the G/H5S2 strain of Pichia pastoris and the culture medium may further include: potassium phosphate buffer, $MgCl_2$, sucrose, UDP-glucose, UDP, and any combination thereof.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A, 1B, 1C, 1D, and 1E depict a steviol glycosides biosynthesis pathway from steviol.

FIGS. 2A, 2B, and 2C summarize the production of rebaudioside A ("Reb A") from stevioside using cultured G/K4S2 cells. FIG. 2A and FIG. 2B summarize the HPLC retention times of stevioside (FIG. 2A) and rebaudioside A (FIG. 2B) standards, respectively. FIG. 2C summarizes the HPLC retention time of rebaudioside A enzymatically produced by the induced G/K4S2 cells as sampled from the G/K4S2 culture medium 24 hours after the introduction of the induced G/K4S2 cells into the in vitro reaction system.

FIG. 3A and FIG. 3B summarize the HPLC retention times of rebaudioside D (FIG. 3A) and rebaudioside M (FIG. 3B) standards, respectively. FIG. 3C summarizes the HPLC retention time of rebaudioside M enzymatically produced by the induced G/K4S2 cells and of remaining rebaudioside D as sampled from the G/K4S2 culture medium 24 hours after the introduction of the induced G/K4S2 cells into the in vitro reaction system.

FIGS. 4A, 4B, and 4C summarize the production of rebaudioside D ("Reb D") from rebaudioside E ("Reb E") using cultured G/K4S2 cells. FIG. 4A and FIG. 4B summarize the HPLC retention times of rebaudioside E (FIG. 4A) and rebaudioside D (FIG. 4B) standards, respectively. FIG. 4C summarizes the HPLC retention time of rebaudioside D enzymatically produced by the induced G/K4S2 cells and of remaining rebaudioside E as sampled from the G/K4S2 culture medium 24 hours after the introduction of the induced G/K4S2 cells into the in vitro reaction system.

FIG. 5A and FIG. 5B summarize the HPLC retention times of rebaudioside A (FIG. 5A) and rebaudioside D (FIG. 5B) standards, respectively. FIG. 5C summarizes the HPLC retention time of rebaudioside D enzymatically produced by the cultured G/H5S2 cells and of remaining rebaudioside A as sampled from the culture medium 24 hours after the introduction of the G/H5S2 cells into the in vitro reaction system. FIG. 5D summarizes the HPLC retention time of rebaudioside D enzymatically produced by a cultured Pichia pastoris strain (H5) in which a vector containing only the HV1-GCW61 sequences was introduced, as well as the remaining rebaudioside A, as sampled from the H5 culture medium 24 hours after the introduction of the induced H5 cells into the in vitro reaction system; the reduced amount of rebaudioside D in the H5 culture medium indicates that both the HV1-GCW61 and the mbSUS1 genes are involved in the conversion of Reb A to Reb D by the G/H5S2 cells. FIG. 5E summarizes the HPLC retention time of rebaudioside D enzymatically produced by a cultured Pichia pastoris strain (pHKA) in which an empty vector lacking both the HV1-GCW61 and the mbSUS1 sequences was incorporated, as well as the remaining rebaudioside A, as sampled from the pHKA culture medium 24 hours after the introduction of the induced pHKA cells into the in vitro reaction system; the lack of rebaudioside D in the pHKA culture medium further indicates that both the HV1-GCW61 and the mbSUS1 sequences are involved in the conversion of Reb A to Reb D by the G/H5S2 cells.

FIG. 6A and FIG. 6B summarize the HPLC retention times of stevioside ("Ste") and rebaudioside E ("Reb E") standards, respectively. FIG. 6C summarizes the HPLC retention time of rebaudioside E enzymatically produced by the cultured G/H5 S2 cells and of remaining stevioside as sampled from the culture medium 24 hours after the introduction of induced G/H5S2 cells into the in vitro reaction system. FIG. 6D summarizes the HPLC retention time of rebaudioside E enzymatically produced by a cultured Pichia pastoris strain (pHKA) in which an empty vector lacking both the HV1-GCW61 and the mbSUS1 sequences was incorporated, as well as the remaining stevioside, as sampled from the reaction 24 hours after the introduction of the induced pHKA cells into the in vitro reaction system; the lack of rebaudioside E in the reaction further indicates that both the HV1-GCW61 and the mbSUS1 sequences are involved in the conversion of Reb A to Reb D by the G/H5S2 cells.

FIGS. 7A, 7B, 7C, 7D, and 7E summarize the production of rebaudioside M ("Reb M") from rebaudioside A ("Reb A") using co-cultured G/K4S2 and G/H5S2 cells. FIG. 7A, FIG. 7B, and FIG. 7C summarize the HPLC retention times of rebaudioside A ("Reb A"), rebaudioside D ("Reb D"), and rebaudioside M ("Reb M") standards, respectively. FIGS. 7D and 7E summarizes the HPLC retention time of rebaudioside M and rebaudioside D enzymatically produced by the co-cultured G/K4S2 and G/H5S2 cells and of remaining rebaudioside A as sampled from the culture medium 24 hours (FIG. 7D) and 48 hours (FIG. 7E) after the introduction of the induced G/K4S2 and G/H5S2 cells into the in vitro reaction system.

Figure 8A:
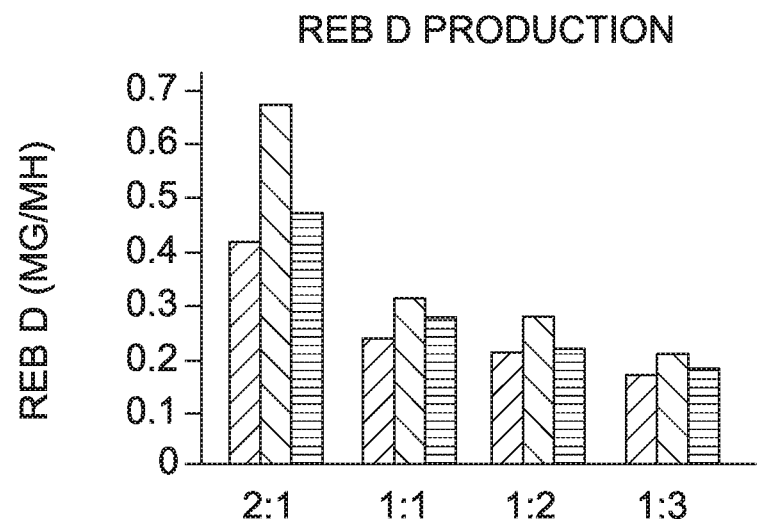
Figure 8B:
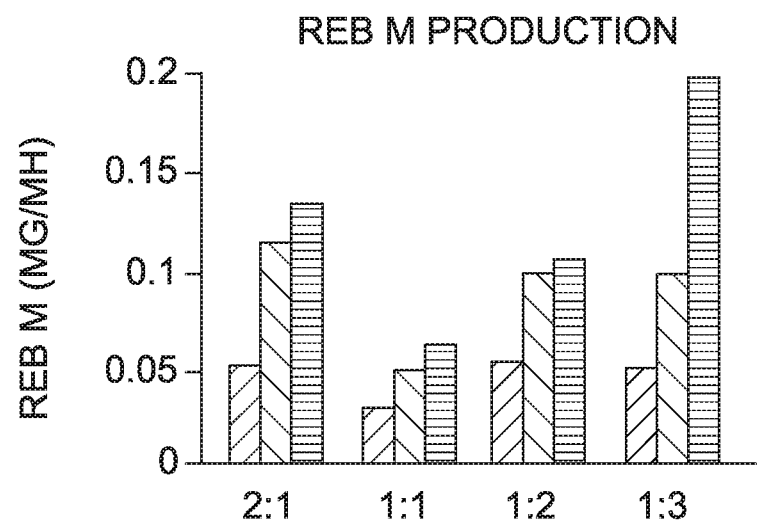
Figure 9A:
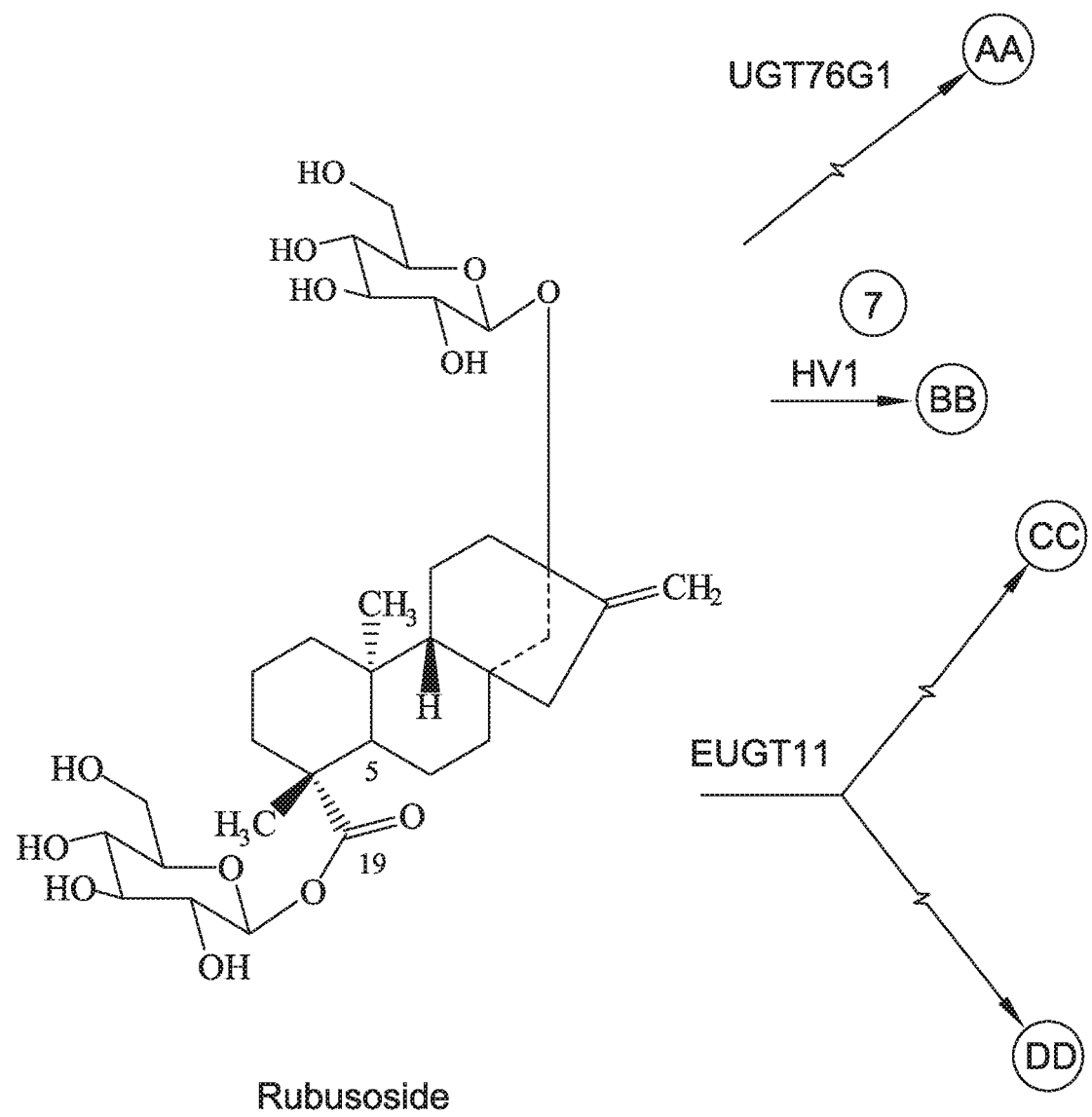
Figure 9B:
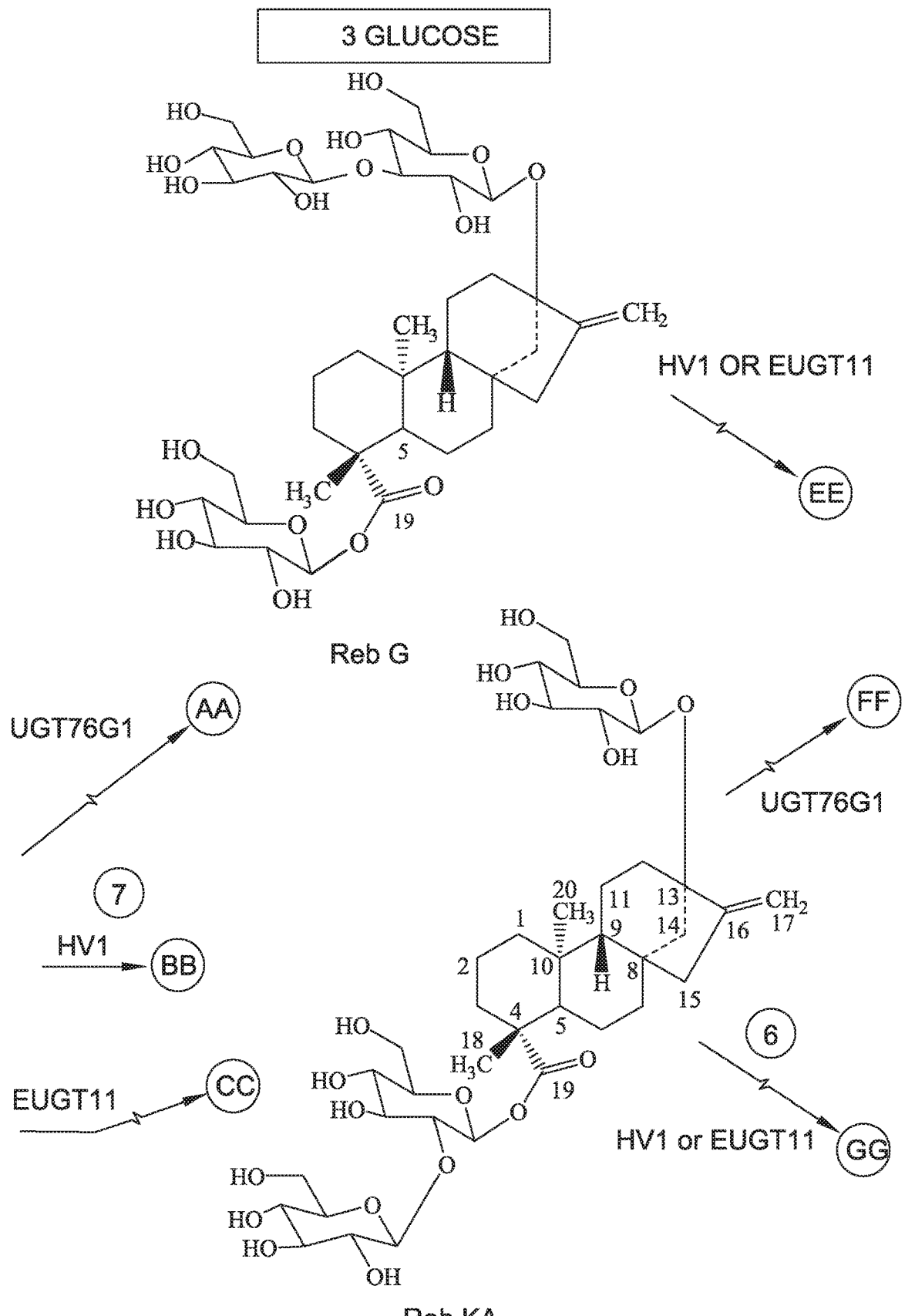
Figure 9C:
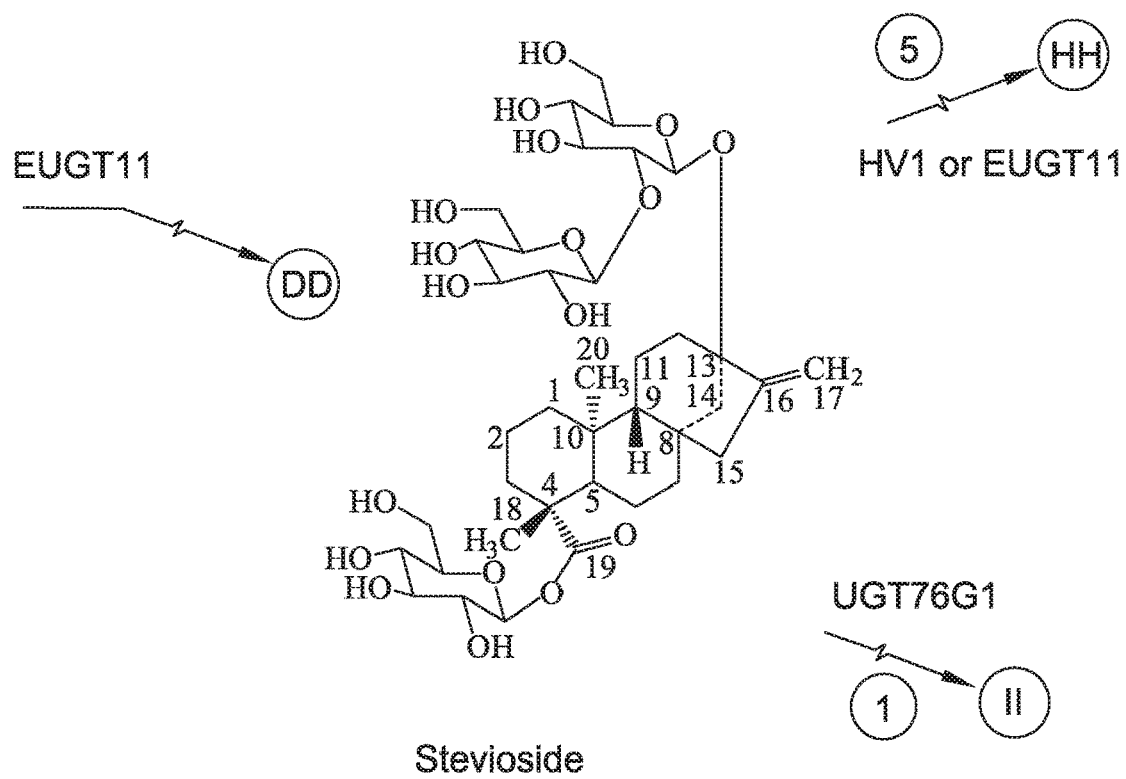
Figure 9D:
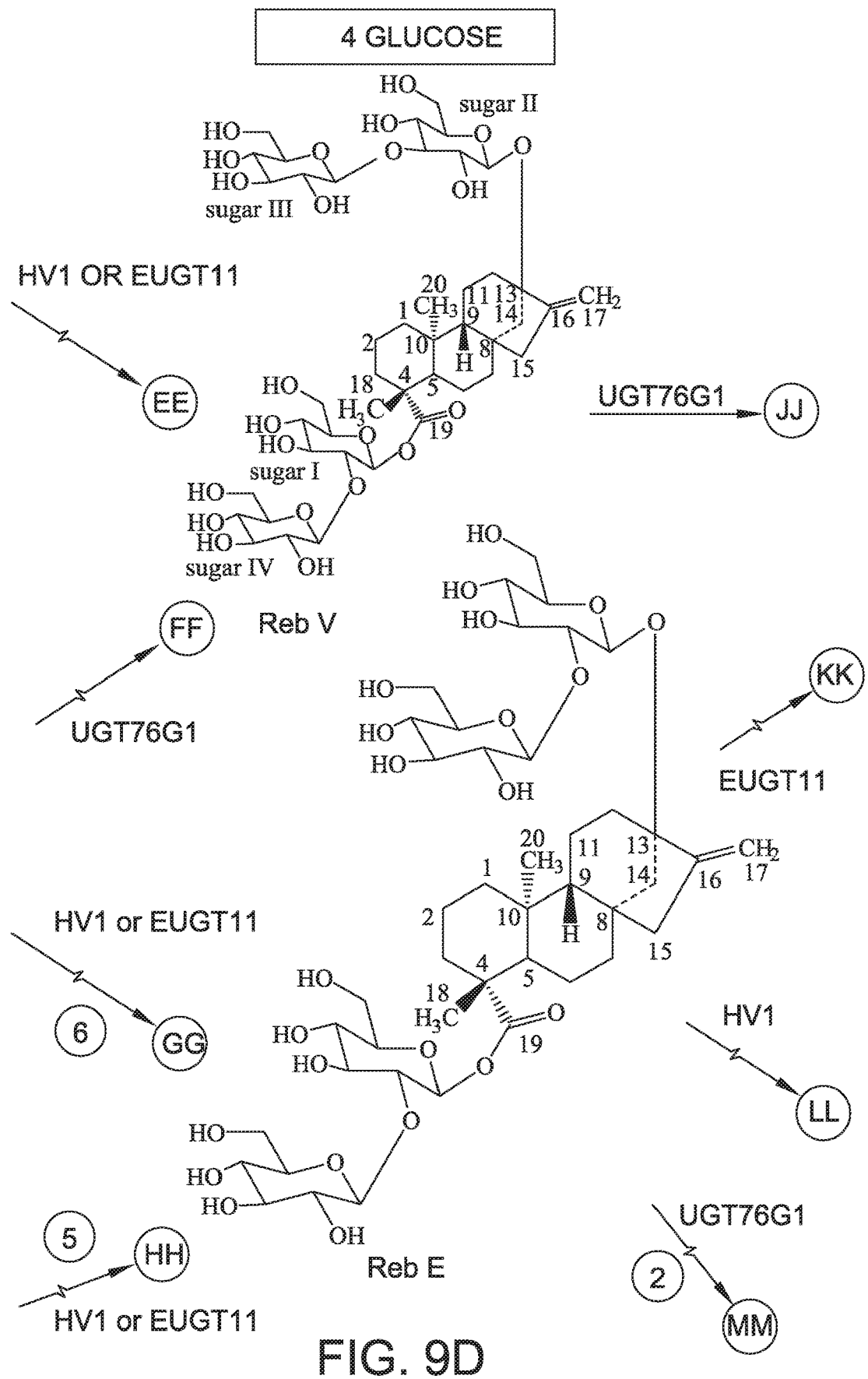
Figure 9E:
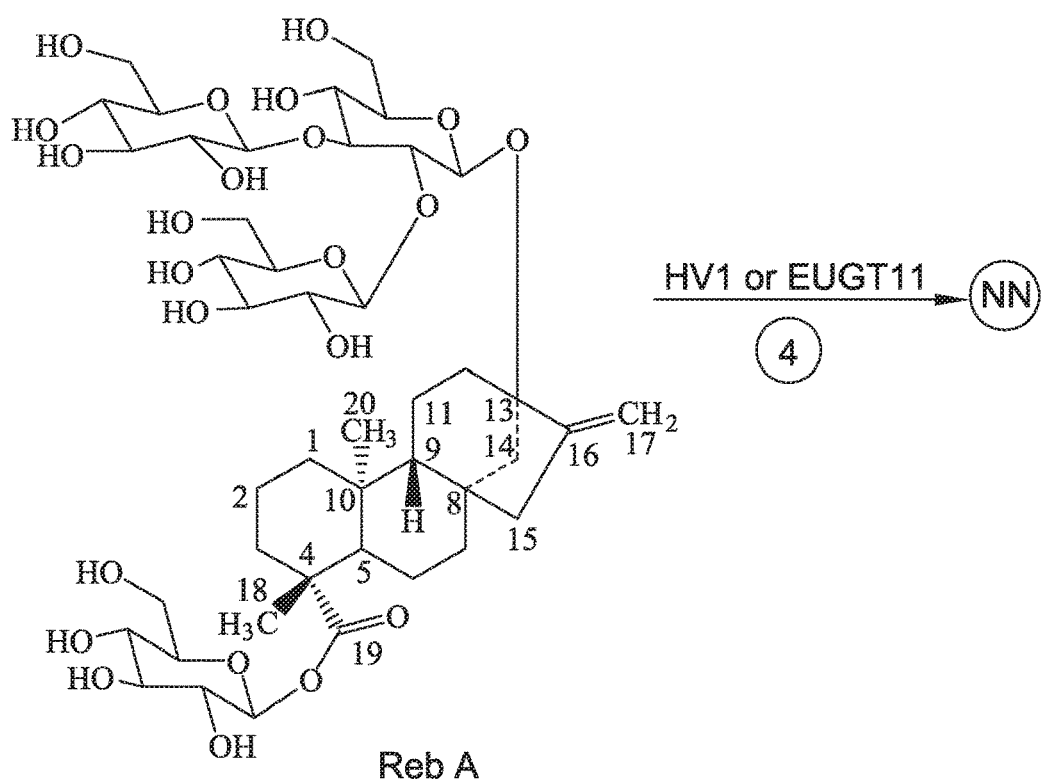
Figure 9F:
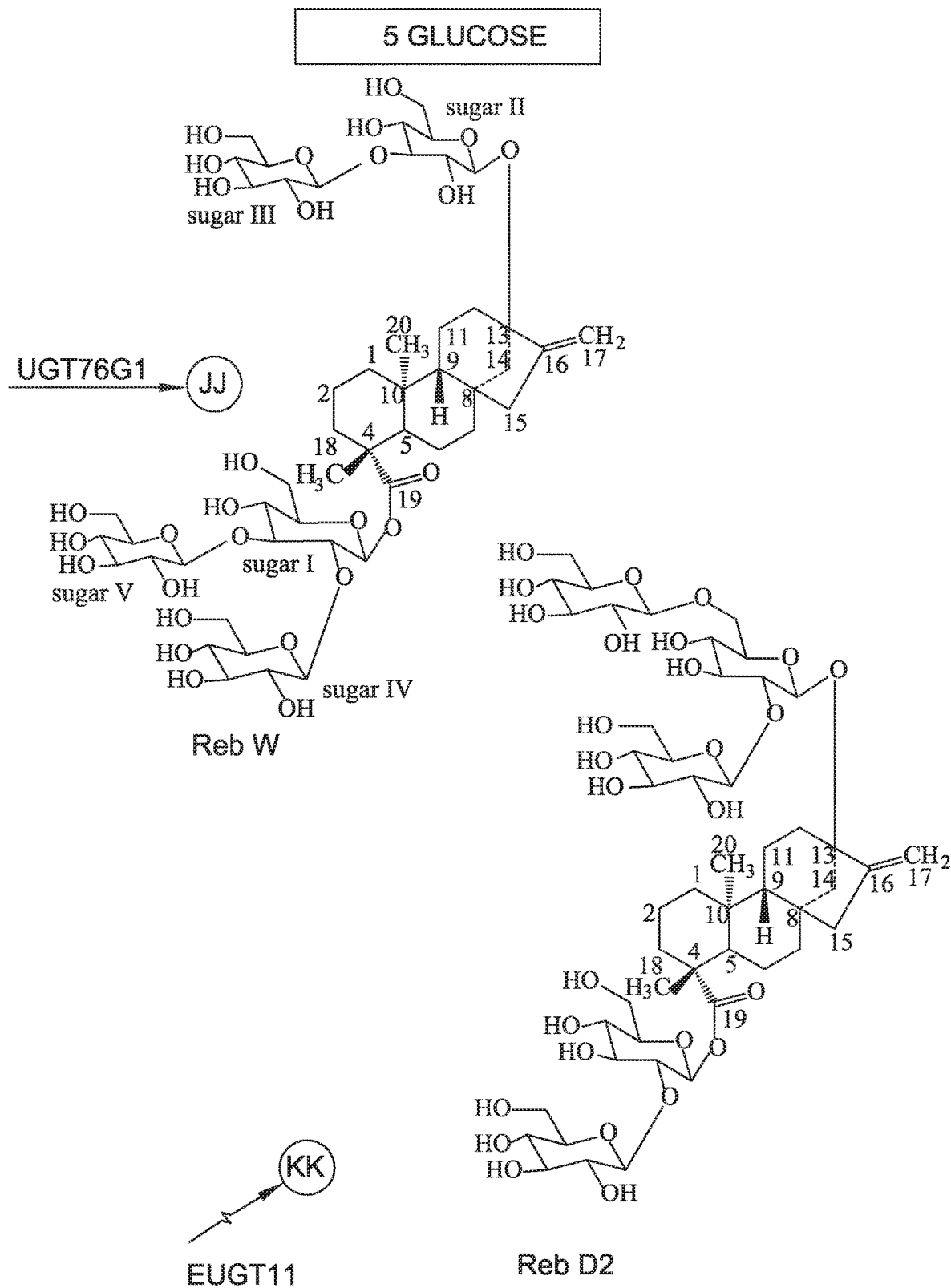
Figure 9G:
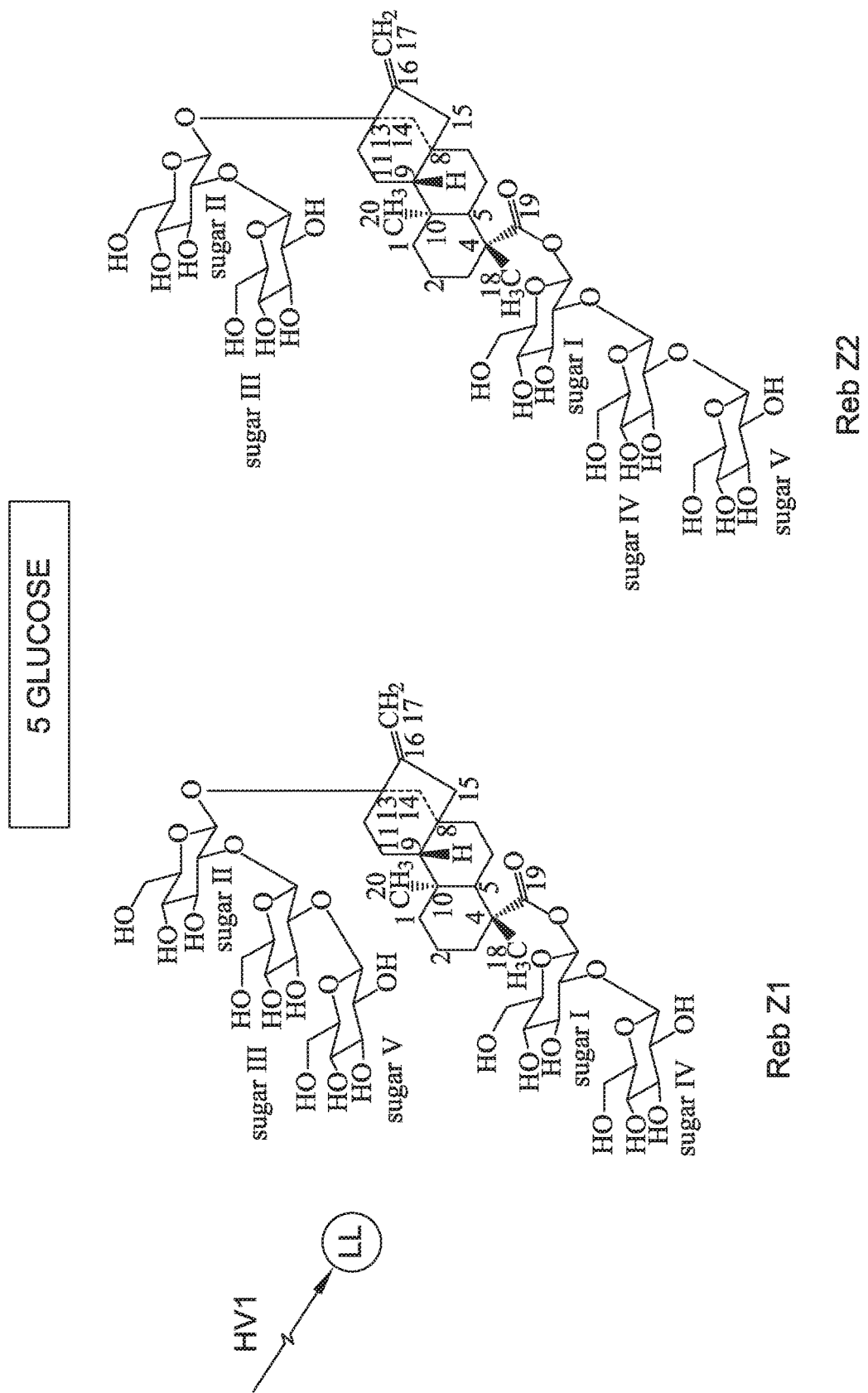
Figure 9H:
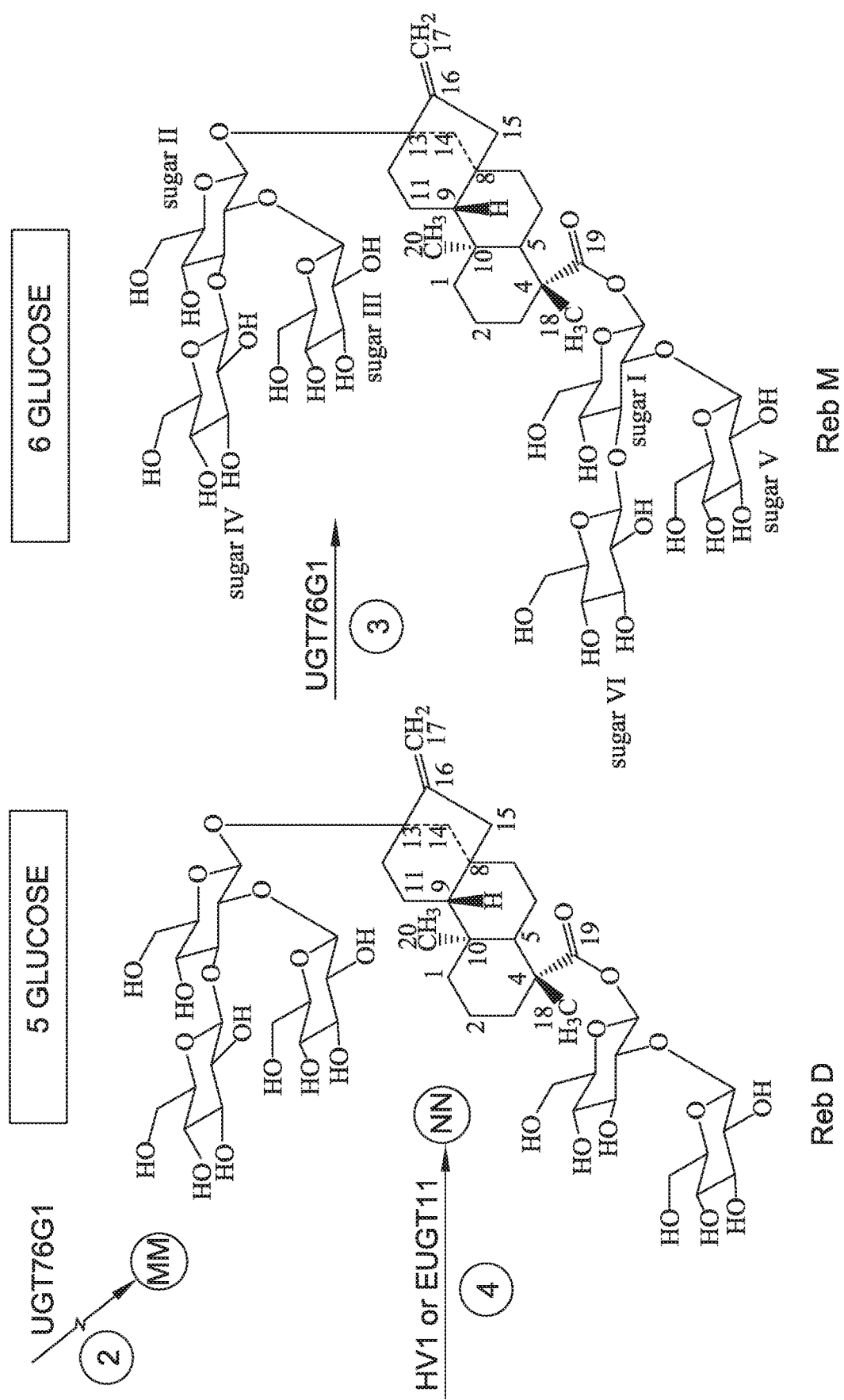

FIG. 8A summarizes the production of rebaudioside D intermediary product ("Reb D") from rebaudioside A ("Reb A") using co-cultured G/K4S2 and G/H5S2 cells at a variety of G/H5S2:G/K4S2 cell density ratios for several times after the introduction of the induced G/K4S2 and G/H5S2 cells into the in vitro reaction system. FIG. 8B summarizes the production of rebaudioside M ("Reb M") from rebaudioside A ("Reb A") using co-cultured G/K4S2 and G/H5S2 cells at a variety of G/H5S2:G/K4S2 cell density ratios 16, 24, and 48 hours after the introduction of the induced G/K4S2 and G/H5S2 cells into the in vitro reaction system.

FIGS. 9A, 9B, 9C, 9D, 9E, 9F, 9G, and 9H are schematic diagrams depicting the biosynthesis pathways of steviol glycosides.

Figure 10:
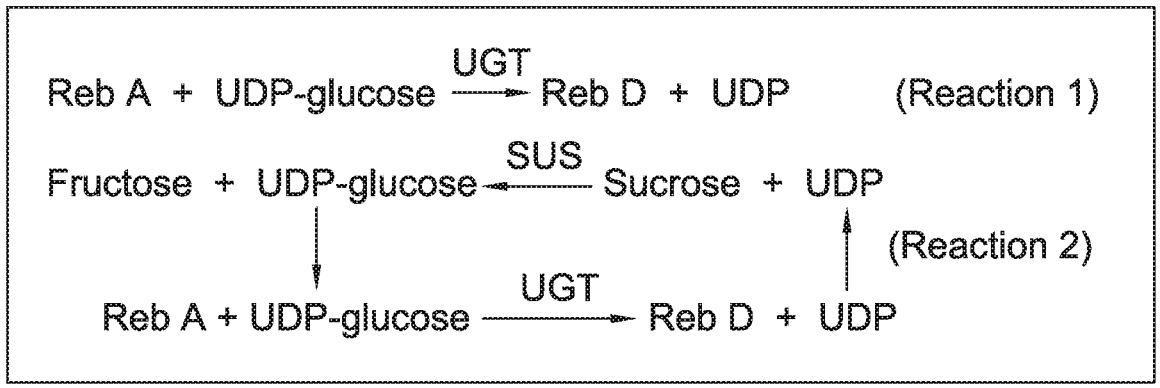

FIG. 10 is a schematic illustration of a coupling reaction system of UDP-glycosyltransferase ("UGT") and sucrose synthase ("SUS"). Reaction 1 shows a UGT catalyzed reaction converting rebaudioside A ("Reb A") to rebaudioside D ("Reb D"), which uses UDP-glucose as a glucose donor and results in the production of UDP. Reaction 2 shows a SUS catalyzed reaction converting UDP to UDP-glucose, which uses sucrose as a glucose donor. Reaction 2 also shows that the SUS catalyzed reaction may be coupled to the UGT catalyzed reaction.

Figure 11:
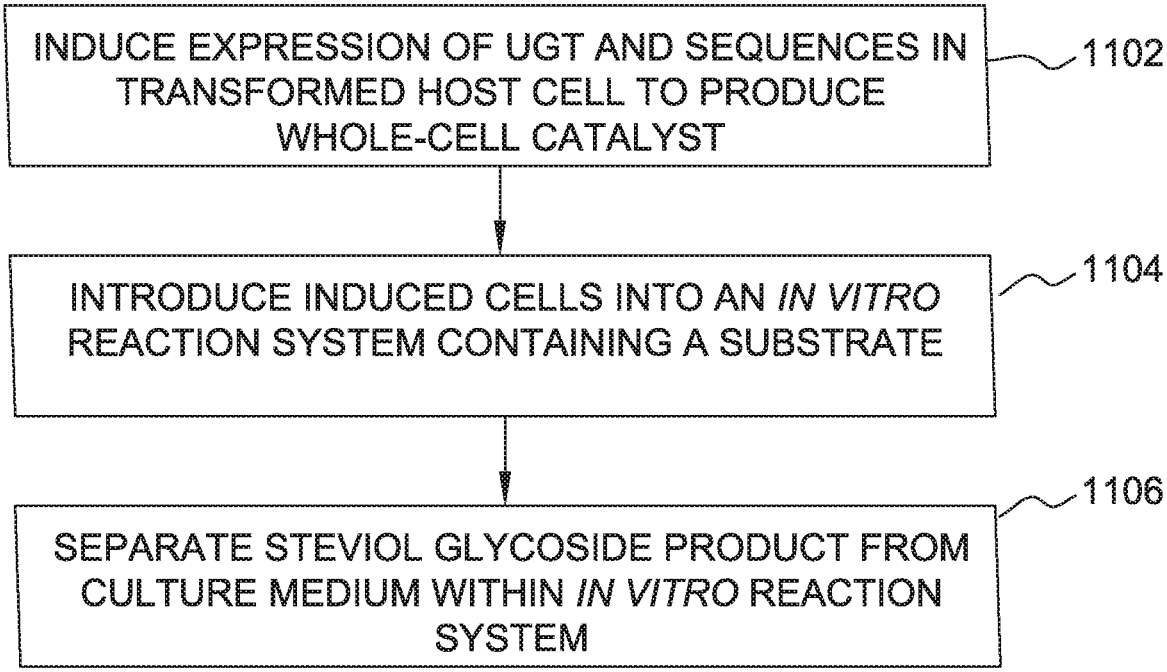

FIG. 11 is a block diagram illustrating a method of producing a steviol glucoside compound using a whole-cell catalyst.

Figure 12A:
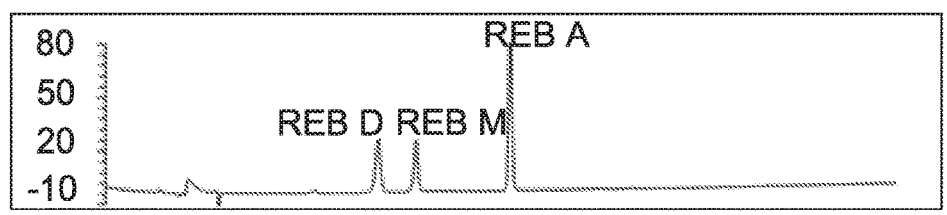
Figure 12B:
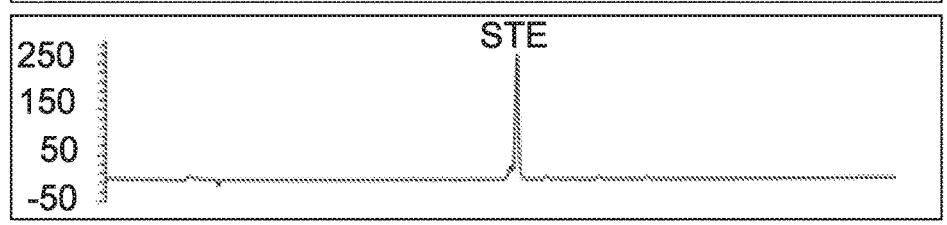
Figure 12C:
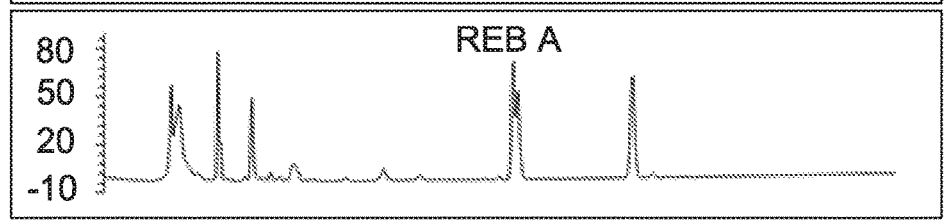
Figure 12D:
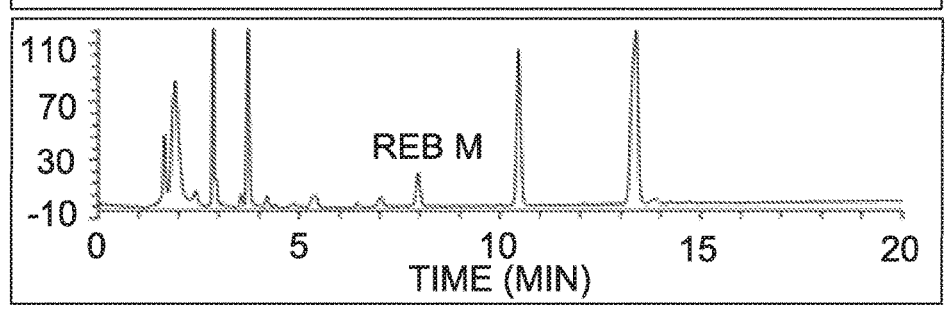

FIGS. 12A, 12B, 12C, and 12D summarize the production of rebaudioside M ("Reb M") from stevioside ("Ste") using co-cultured G/K4S2 and G/H5S2 cells. FIG. 12A and FIG. 12B summarize the HPLC retention times of rebaudioside A ("Reb A"), rebaudioside D ("Reb D"), rebaudioside M ("Reb M"), and stevioside ("Ste") standards, respectively. FIGS. 12C and 12D summarize the HPLC retention time of rebaudioside M, rebaudioside D and rebaudioside A enzymatically produced by the co-cultured G/K4S2 and G/H5S2 cells and of remaining stevioside as sampled from the culture medium 10 hours (FIG. 12C) and 24 hours (FIG. 12D) after the introduction of the induced G/K4S2 and G/H5S2 cells into the in vitro reaction system.

Figure 13A:
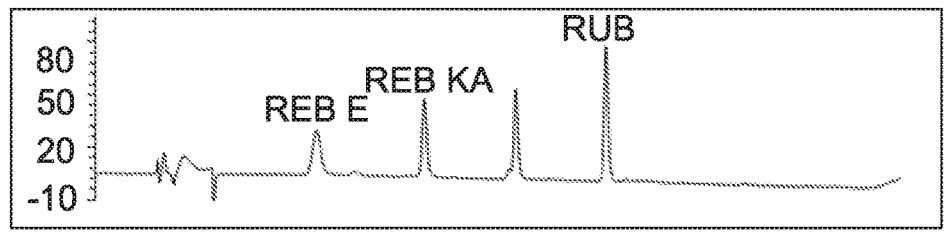
Figure 13B:
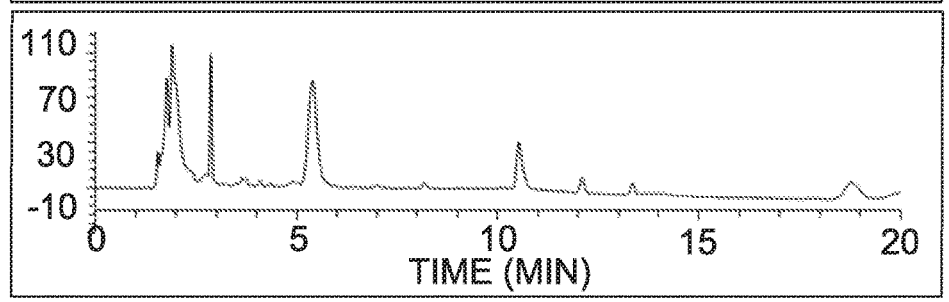

FIGS. 13A and 13B summarize the production of rebaudioside E ("Reb E") from rebaudioside KA ("Reb KA") using cultured G/H5S2 cells. FIG. 13A summarizes the HPLC retention times of rebaudioside E ("Reb E"), rebaudioside KA ("Reb KA"), rubusoside ("Rub") standards, respectively. FIG. 13B summarizes the HPLC retention time of rebaudioside E enzymatically produced by the cultured G/H5S2 cells and of remaining rebaudioside KA as sampled from the culture medium 24 hours after the introduction of the G/H5S2 cells into the in vitro reaction system.

Figure 14A:
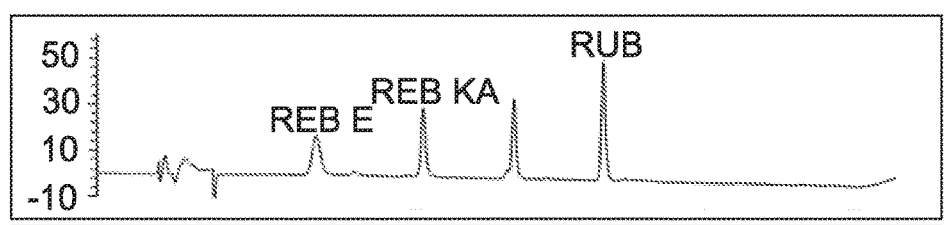
Figure 14B:
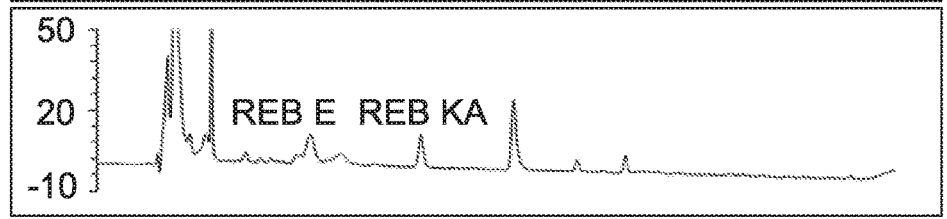
Figure 14C:
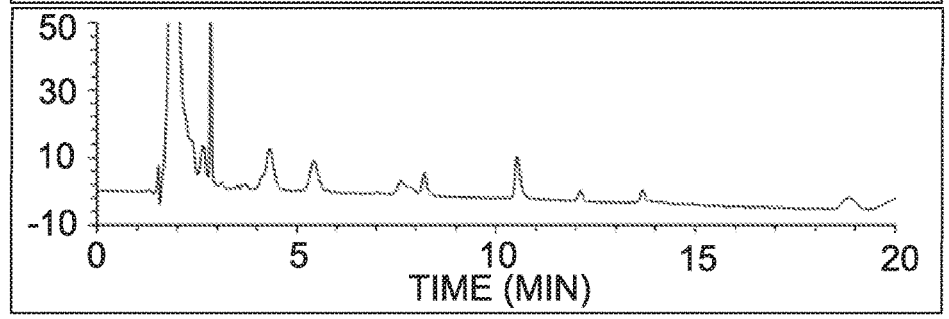

FIGS. 14A, 14B, and 14C summarize the production of rebaudioside KA ("Reb KA") and rebaudioside E ("Reb E") from rubusoside ("Rub") using G/H5S2 cells. FIG. 14A summarizes the HPLC retention times of rebaudioside E ("Reb E"), rebaudioside KA ("Reb KA"), and rubusoside ("Rub") standards, respectively. FIGS. 14B and 14C summarize the HPLC retention time of rebaudioside KA and rebaudioside E enzymatically produced by G/H5S2 cells as sampled from the culture medium 14 hours (FIG. 14B) and 24 hours (FIG. 14C) after the introduction of the induced G/H5S2 cells into the in vitro reaction system.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

The term "complementary" is used according to its ordinary and customary meaning as understood by a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subject technology also includes isolated nucleic acid fragments that are complementary to the complete sequences as reported in the accompanying Sequence Listing as well as those substantially similar nucleic acid sequences.

The terms "nucleic acid" and "nucleotide" are used according to their respective ordinary and customary meanings as understood by a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is used according to its ordinary and customary meaning as understood by a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein refers to a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are used according to their respective ordinary and customary meanings as understood by a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are used according to their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from superfamilies and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical.

"Percent (%) amino acid sequence identity" with respect to the variant polypeptide sequences of the subject technology refers to the percentage of amino acid residues in a candidate sequence that are identical with the amino acid residues of a reference polypeptide after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

"Coding sequence" is used according to its ordinary and customary meaning as understood by a person of ordinary skill in the art, and is used without limitation to refer to a DNA sequence that encodes for a specific amino acid sequence.

"Suitable regulatory sequences" is used according to its ordinary and customary meaning as understood by a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is used according to its ordinary and customary meaning as understood by a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is used according to its ordinary and customary meaning as understood by a person of ordinary skill in the art, and is used without limitation to refer to the transcription and stable accumulation of sense (mRNA) or antisense RNA derived from the nucleic acid fragment of the subject technology. "Overexpression" refers to the production of a gene product in transgenic or recombinant organisms that exceeds levels of production in normal or non-transformed organisms.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are used according to their ordinary and customary meanings as understood by a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are used according to their ordinary and customary meanings as understood by a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described, for example, by Sambrook, J., Fritsch, E. F. and Maniatis, T. Molecular Cloning: A Laboratory Manual, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; the entireties of each of which are hereby incorporated herein by reference to the extent they are consistent herewith.

As used herein, "synthetic" or "organically synthesized" or "chemically synthesized" or "organically synthesizing" or "chemically synthesizing" or "organic synthesis" or "chemical synthesis" are used to refer to preparing the compounds through a series of chemical reactions; this does not include extracting the compound, for example, from a natural source.

The term "orally consumable product" as used herein refers to any beverage, food product, dietary supplement, nutraceutical, pharmaceutical composition, dental hygienic composition and cosmetic product which are contacted with the mouth of man or animal, including substances that are taken into and subsequently ejected from the mouth and substances which are drunk, eaten, swallowed, or otherwise ingested; and that are safe for human or animal consumption when used in a generally acceptable range of concentrations.

The term "food product" as used herein refers to fruits, vegetables, juices, meat products such as ham, bacon and sausage; egg products, fruit concentrates, gelatins and gelatin-like products such as jams, jellies, preserves, and the like; milk products such as ice cream, sour cream, yogurt, and sherbet; icings, syrups including molasses; corn, wheat, rye, soybean, oat, rice and barley products, cereal products, nut meats and nut products, cakes, cookies, confectionaries such as candies, gums, fruit flavored drops, and chocolates, chewing gum, mints, creams, icing, ice cream, pies and breads. "Food product" also refers to condiments such as herbs, spices and seasonings, flavor enhancers, such as monosodium glutamate. "Food product" further refers to also includes prepared packaged products, such as dietetic sweeteners, liquid sweeteners, tabletop flavorings, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. "Food product" also refers to diet or low-calorie food and beverages containing little or no sucrose.

As used herein, the term "stereoisomer" is a general term for all isomers of individual molecules that differ only in the orientation of their atoms in space. "Stereoisomer" includes enantiomers and isomers of compounds with more than one chiral center that are not mirror images of one another (diastereomers).

As used herein, the term "sweetness intensity" refers to the relative strength of sweet sensation as observed or experienced by an individual, e.g., a human, or a degree or amount of sweetness detected by a taster, for example on a Brix scale.

As used herein, the term "enhancing the sweetness" refers to the effect of rebaudioside M and/or rebaudioside D in increasing, augmenting, intensifying, accentuating, magnifying, and/or potentiating the sensory perception of one or more sweetness characteristics of a beverage product or a consumable product of the present disclosure without changing the nature or quality thereof, as compared to a corresponding orally consumable product that does not contain rebaudioside M and/or rebaudioside D.

As used herein, the term "off-taste(s)" refers to an amount or degree of taste that is not characteristically or usually found in a beverage product or a consumable product of the present disclosure. For example, an off-taste is an undesirable taste of a sweetened consumable to consumers, such as, a bitter taste, a licorice-like taste, a metallic taste, an aversive taste, an astringent taste, a delayed sweetness onset, a lingering sweet aftertaste, and the like, etc.

As used herein, the term "w/v-%" refers to the weight of a compound, such as a sugar, (in grams) for every 100 ml of a liquid orally consumable product of the present disclosure containing such compound. As used herein, the term "w/w-%" refers to the weight of a compound, such as a sugar, (in grams) for every gram of an orally consumable product of the present disclosure containing such compound.

As used herein, the term "ppm" refers to part(s) per million by weight, for example, the weight of a compound, such as rebaudioside M and/or rebaudioside D (in milligrams) per kilogram of an orally consumable product of the present disclosure containing such compound (i.e., mg/kg) or the weight of a compound, such as rebaudioside M and/or rebaudioside D (in milligrams) per liter of an orally consumable product of the present disclosure containing such compound (i.e., mg/L); or by volume, for example the volume of a compound, such as rebaudioside M and/or rebaudioside D (in milliliters) per liter of an orally consumable product of the present disclosure containing such compound (i.e., ml/L).

In accordance with the present disclosure, steviol glycoside non-caloric sweeteners and methods for synthesizing the steviol glycosides are disclosed. Also in accordance with the present disclosure a whole-cell catalyst that includes one or more engineered cells producing one or more enzymes, methods of producing the whole-cell catalyst, and methods of using the whole-cell catalysts to prepare the steviol glycosides are disclosed.

Whole-Cell Catalysts

In one aspect, at least one whole-cell catalyst is provided. In this aspect, the at least one whole-cell catalyst is a transformed host cell that expresses at least one enzyme including, but not limited to: a uridine dipospho glycosyltransferase (UDP-glycosyltransferase or UGT) and a sucrose synthase (SUS). In various aspects, described herein below, the at least one whole-cell catalyst may be used in a method of synthesizing a non-caloric sweetener that includes mixing the at least one whole cell catalyst with a suitable substrate; the enzymes produced by the at least one whole-cell catalyst catalyze at least one glycosylation reaction of the substrate and any resulting intermediate products to produce the desired non-caloric sweetener.

In another aspect, the UGT enzyme expressed by the transformed host cell may be displayed on the surface of the host cell. In this aspect, the expressed UGT enzyme may be fused with a display polypeptide to facilitate the display of the expressed UGT enzyme on the surface of the transformed host cell. The display polypeptide fused with the expressed enzyme may be selected based on any one or more of at least several factors including, but not limited to: non-interference with the enzymatic function of the displayed UGT enzyme and compatibility with the type of host cell.

In various aspects, the whole-cell catalyst may include a transformed host cell that expresses a UGT enzyme attached to the surface of the cell and that further expresses a sucrose synthase (SUS) intracellularly. In these various aspects, the host cell is transformed by the incorporation of at least one expression cassette that includes at least one nucleotide sequence that encodes the at least one enzyme including, but not limited to: a uridine dipospho glycosyltransferase (UDP-glycosyltransferase or UGT) and a sucrose synthase (SUS). In addition, the nucleotide sequence encoding the UGT enzyme may further include an additional nucleotide segment encoding a display polypeptide, so that the host cell expresses a fusion polypeptide that includes the UGT enzyme fused with the display protein.

Host Cells

In this aspect, the transformed host cell may be any suitable host cell transformed by at least one expression cassette that includes at least one nucleotide sequence encoding the at least one enzyme expressed by each whole-cell catalyst. Non-limiting examples of suitable host cells for transformation to a whole-cell catalyst include: bacteria, yeast, filamentous fungi, cyanobacteria algae, and plant cells.

In one aspect, the host cell may be a bacteria including, but not limited to: enteric bacteria such as *Escherichia, Salmonella,* and *Klebsiella; Bacillus; Acinetobacter; Pantoea;* Actinomycetes such as *Streptomyces* and *Corynebacterium;* Methanotrophs such as *Methylosinus, Methylomonas, Rhodococcus* and *Pseudomona; Clostridium* such as *Clostridium acetobutylicum;* and Cyanobacteria, such as *Rhodobacter* and *Synechocystis.* In another aspect, the host cell may be yeast including, but not limited to: *Arxula* spp., *Candida* spp., *Debaryomyces* spp., *Hansenula* spp., *Kluyveromyces* spp., *Mucor* spp., *Pachysolen* spp., *Phaffia* spp., *Pichia* spp., *Rhodosporidium* spp., *Saccharomyces* spp., *Saccharomycopsis* spp., *Scwanniomyces* spp., *Tricosporon* spp., *Torulopsis* spp., *Yarrowia* spp., and *Zygosaccharomyces* spp. In yet another aspect, the host cell may be yeast including, but not limited to: *Arxula adeninivorans, Candida albicans, Candida boidinii, Candida famata, Candida maltosa, Candida tropicalis, Candida utilis, Candida shehatae, Hansenula polymorpha, Kluyveromyces marxianus, Kluyveromyces lactis, Pachysolen tannophilus, Phaffia rhodozyma, Pichia guillermondii, Pichia methanolica, Pichia pastoris, Rhodosporidium toruloides, Saccharomyces cerevisiae, Saccharomyces cerevisiae* var. *diastaticus, Saccharomyces boulardii, Saccharomyces pyriformis, Saccharomyces bayanis, Saccharomycopsis fibuligera, Scwanniomyces castellii, Scwanniomyces occidentalis, Tricosporon cutaneum, Yarrowia lipolytica,* and *Zygosaccharomyces rouxii.* In an additional aspect, the host cell may be a filamentous fungus including, but not limited to: *Aspergillus* and *Arthrobotrys.* In another additional aspect, the host cell may be an algae including, but not limited to: *Spirulina, Haemotacoccus,* and *Dunaliella.*

In yet another aspect, the host cell may be a plant cell including, but not limited to, any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multicellular organism capable of photosynthesis, including monocotyledons and dicotyledons. In some embodiments, the plant cell can be an *Arabidopsis* plant cell, a tobacco plant cell, a soybean plant cell, a petunia plant cell, or a cell from another oilseed crop including, but not limited to, a canola plant cell, a rapeseed plant cell, a palm plant cell, a sunflower plant cell, a cotton plant cell, a corn plant cell, a peanut plant cell, a flax plant cell, and a sesame plant cell. Useful plant hosts can include any plant that supports the production of the recombinant polypeptides of the subject technology. Suitable green plants for use as hosts include, but are not limited to, soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* spp.), barley (*Hordeum vulgare*), oats (*Avena sativa*), sorghum (*Sorghum bicolor*), rice (*Oryza sativa*), *Arabidopsis,* cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. In one aspect, the host cells may be plant cells derived from a plant including, but not limited to: *Arabidopsis thaliana,* rice (*Oryza sativa*), *Hordeum vulgare,* switchgrass (*Panicum vigratum*), *Brachypodium* spp., *Brassica* spp., and *Crambe abyssinica.*

In various aspects, the expression cassettes that include at least one nucleoside sequence encoding at least one enzyme maybe incorporated into these and other host cells to prepare large, commercially useful amounts of steviol glycosides.

Enzymes

In various aspects, at least one expression cassette containing at least one nucleotide sequence encoding at least one enzyme is incorporated into the host cell to transform the host cell into a whole-cell catalyst. Typically, the at least one expression cassette is selected for compatibility with the host cell type, and the codons within the at least one nucleotide sequence encoding the at least one enzyme may be subjected to codon-optimization using known methods in order to enhance expression of the at least one enzyme within the selected host cell type. The design of the expression cassette depends on such factors as the choice of the host cell to be transformed, the level of expression of enzyme desired, and the like. The expression cassettes may be introduced into the host cell to thereby produce the recombinant polypeptide enzymes including, but not limited to a uridine dipospho glycosyltransferase (UDP-glycosyltransferase) and a sucrose synthase (SUS).

In an aspect, a nucleotide sequence incorporated into the at least one expression cassette may include at least one nucleotide sequence that encodes a uridine dipospho glycosyltransferase (UDP-glycosyltransferase). UDP-glycosyltransferase (UGT) refers to an enzyme that transfers a sugar residue from an activated donor molecule (typically UDP-glucose) to an acceptor molecule. In various aspects, the UGT enzyme may have any one or more activities related to the synthesis of steviol glycosides including, but not limited to: 1,2-19-O-glucose glycosylation activity, 1,2-13-O-glucose glycosylation activity, 1,3-13-O-glucose glycosylation activity, and 1,3-19-O-glucose glycosylation. The 1,2-19-O-glucose glycosylation activity refers to an enzymatic activity that transfers a sugar moiety to the C-2' of the 19-O-glucose moiety of substrate including, but not limited to: rubusoside, stevioside, rebaudioside A or rebaudioside E (see FIGS. 9A, 9B, 9C, 9D, 9E, 9F, 9G, and 9H). The 1,2-13-O-glucose glycosylation activity refers to an enzymatic activity that transfers a sugar moiety to the C-2' of the 13-O-glucose moiety of a substrate including, but not limited to: rebaudioside KA and rebaudioside E (see FIGS. 9A, 9B, 9C, 9D, 9E, 9F, 9G, and 9H). Any known UGT may be incorporated into the at least one expression cassette including, but not limited to: UGT76G1, HV1, EUGT11, and any combination thereof.

UGT76G1 is a UGT with a 1,3-13-O-glucose glycosylation activity to produce related rebaudiosides A and D from stevioside and rebaudioside E, respectively. In addition, UGT76G1 also has a 1,3-19-O-glucose glycosylation activity to produce rebaudioside M from rebaudioside D. UGT76G1 can also convert rebaudioside KA to Reb V and continue to form Reb W (see FIGS. 9A, 9B, 9C, 9D, 9E, 9F, 9G, and 9H). In one aspect, the UGT76G1 enzyme has the amino acid sequence of SEQ ID NO:9.

In this one aspect, the at least one expression cassette may include a nucleotide sequence encoding the UGT76G1 enzyme that includes a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:10. Suitably, the nucleotide sequence encoding the UGT76G1 enzyme may have an amino acid sequence that has at least 80% sequence identity to the amino acid sequence set forth in SEQ ID NO:9. More suitably, the nucleotide sequence may encode a UGT76G1 enzyme with an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:9. The nucleotide sequence encoding the UGT76G1 enzyme thus includes those nucleotide sequences encoding functional fragments of SEQ ID NO:9, functional variants of SEQ ID NO:9, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:9. As known by those skilled in the art, the nucleic acid sequence encoding the UGT76G1 enzyme can be codon optimized for expression in a suitable host organism such as, for example, bacteria or yeast.

HV1 is a UGT with a 1,2-19-O-glucose glycosylation activity to produce related rebaudiosides E, D and Z from stevioside, rebaudioside A, and rebaudioside E, respectively. HV1 also has 1,2-19-O-glucose glycosylation activity to produce rebaudioside KA from rubusoside. HV1 also can convert Reb G to Reb V and Reb KA to Reb E (see FIGS. 9A, 9B, 9C, 9D, 9E, 9F, 9G, and 9H). HV1 has 1,2-13-O-glucose glycosylation activity to produce rebaudioside Z1 from rebaudioside E. In one aspect, the HV1 enzyme has the amino acid sequence of SEQ ID NO:7.

In this one aspect, the at least one expression cassette may include a nucleotide sequence encoding the HV1 enzyme that includes a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:8. Suitably, the nucleotide sequence encoding the HV1 enzyme may have an amino acid sequence that has at least 80% sequence identity to the amino acid sequence set forth in SEQ ID NO:7. More suitably, the nucleotide sequence may encode a HV1 enzyme with an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:7. The nucleotide sequence encoding the HV1 enzyme thus includes those nucleotide sequences encoding functional fragments of SEQ ID NO:7, functional variants of SEQ ID NO:7, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:7. As known by those skilled in the art, the nucleic acid sequence encoding the HV1 enzyme can be codon optimized for expression in a suitable host organism such as, for example, bacteria or yeast.

EUGT11 is a UGT having at least a 1,2-19-O-glucose glycosylation activity and a 1,2-13-O-glucose glycosylation activity. EUGT11 may catalyze the glycosylation of stevioside to rebaudioside E and the glycosylation rebaudioside A to rebaudioside D (see FIGS. 9A, 9B, 9C, 9D, 9E, 9F, 9G, and 9H). EUGT11 may also be used in vitro to synthesize rebaudioside D2 from rebaudioside E by another enzyme activity, β1,6-13-O-glucose glycosylation activity. EUGT11 also has a 1,2-19-O-glucose glycosylation activity to produce rebaudioside KA from rubusoside.

In various aspects, the UGT may be fused with a display polypeptide as described herein above so that the UGT may be displayed on the surface of the transformed host cell. In one aspect, the at least one expression cassette may include at least one nucleotide sequence that includes a first nucleotide portion that includes a sequence encoding a UGT enzyme as described herein previously and a second nucleotide portion that encodes a display polypeptide. In this one aspect, the at least one nucleotide sequence may express a fusion protein that includes the UGT enzyme attached to the display polypeptide so that the UGT enzyme is attached to the cell surface of the host cells via the display polypeptide.

In various aspects, the display polypeptide may be selected to be compatible with the type of host cell transformed to produce the whole-cell catalyst. In an aspect, if the host cell is a bacteria cell, the UGT enzyme may be fused with a bacterial cell surface protein including, but not limited to: a bacterial outer membrane protein or a fimbriae or flagella protein. In another aspect, if the host cell is a yeast cell, the UGT enzyme may be fused with a yeast cell surface protein including, but not limited to: a yeast cell wall protein such as GCW61 (SEQ ID NO:5), a subunit of a yeast mating adhesion protein such as agglutinin, or a biotin-binding peptide. In this other aspect, if the UGT enzyme is fused with a subunit of a yeast mating adhesion protein such as agglutinin, the yeast host cell may be further transformed to express a corresponding subunit of the yeast mating adhesion protein attached to the yeast cell wall so that the expressed UGT-agglutinin fusion protein may bind to the corresponding subunit attached to the yeast cell wall, resulting in the display of the UGT enzyme on the cell wall surface. In this other aspect, if the UGT enzyme is fused with a biotin-binding peptide, the yeast cell may be further modified to display biotin on the yeast cell surface and to biotinylate the fusion protein prior to secretion; the yeast cell is contacted with avidin, which binds to the biotin in the yeast cell wall as well as to the biotinylated fusion proteins.

In one aspect, if the host cell is a Pichia pastoris yeast cell, the display polypeptide fused with the UGT enzyme may be a Pichia cell wall protein (GCW61) having the amino acid sequence of SEQ ID NO:5.

In this one aspect, the at least one expression cassette may include a nucleotide sequence encoding a Pichia cell wall protein (GCW61) that includes a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:6. Suitably, the nucleotide sequence encoding the Pichia cell wall protein (GCW61) may have an amino acid sequence that has at least 80% sequence identity to the amino acid sequence set forth in SEQ ID NO:5. More suitably, the nucleotide sequence may encode a Pichia cell wall protein (GCW61) with an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:5. The nucleotide sequence encoding the Pichia cell wall protein (GCW61) thus includes those nucleotide sequences encoding functional fragments of SEQ ID NO:5, functional variants of SEQ ID NO:5, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:5. As known by those skilled in the art, the nucleic acid sequence encoding the Pichia cell wall protein (GCW61) can be codon optimized for expression in a suitable host organism such as, for example, bacteria or yeast.

In another aspect, the nucleotide sequence encoding the Pichia cell wall protein (GCW61) may be inserted in frame to the C-terminal of the nucleotide sequence encoding the UGT enzyme. In this other aspect, the nucleotide sequence encoding the UGT enzyme may include any of the nucleotide sequences described herein above including, but not limited to: SEQ ID NO:10 encoding the UGT76G1 enzyme and SEQ ID NO:8 encoding the HV1 enzyme. In this other aspect, the fusion nucleotide sequence that includes the GCW61 sequence (SEQ ID NO:6) inserted in frame to the C-terminal of the UGT76G1 nucleotide sequence (SEQ ID NO:10) or HV1 nucleotide sequence (SEQ ID NO:8) is expressed as one of the fusion proteins UGT76G1-GCW61 (SEQ ID NO:3) or HV1-GCW61 (SEQ ID NO:1), respectively.

In this other aspect, the at least one expression cassette may include a nucleotide sequence encoding a fused UGT enzyme-cell wall polypeptide (UGT76G1-GCW61) that includes a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:4. Suitably, the nucleotide sequence encoding the fused UGT enzyme-cell wall polypeptide (UGT76G1-GCW61) may have an amino acid sequence that has at least 80% sequence identity to the amino acid sequence set forth in SEQ ID NO:3. More suitably, the nucleotide sequence may encode a fused UGT enzyme-cell wall polypeptide (UGT76G1-GCW61) with an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:3. The nucleotide sequence encoding the fused UGT enzyme-cell wall polypeptide (UGT76G1-GCW61) thus includes those nucleotide sequences encoding functional fragments of SEQ ID NO:3, functional variants of SEQ ID NO:3, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:3. As known by those skilled in the art, the nucleic acid sequence encoding the fused UGT enzyme-cell wall polypeptide (UGT76G1-GCW61) can be codon optimized for expression in a suitable host organism such as, for example, bacteria or yeast.

In this other aspect, the at least one expression cassette may also include a nucleotide sequence encoding a fused UGT enzyme-cell wall polypeptide (HV1-GCW61) that includes a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:2. Suitably, the nucleotide sequence encoding the fused UGT enzyme-cell wall polypeptide (HV1-GCW61) may have an amino acid sequence that has at least 80% sequence identity to the amino acid sequence set forth in SEQ ID NO:1. More suitably, the nucleotide sequence may encode a fused UGT enzyme-cell wall polypeptide (HV1-GCW61) with an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:1. The nucleotide sequence encoding the fused UGT enzyme-cell wall polypeptide (HV1-GCW61) thus includes those nucleotide sequences encoding functional fragments of SEQ ID NO:1, functional variants of SEQ ID NO:1, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:1. As known by those skilled in the art, the nucleic acid sequence encoding the fused UGT enzyme-cell wall polypeptide (HV1-GCW61) can be codon optimized for expression in a suitable host organism such as, for example, bacteria or yeast.

In another aspect, a nucleotide sequence incorporated into the at least one expression cassette may include at least one nucleotide sequence that encodes a sucrose synthase (SUS). Sucrose synthases (SUS) catalyze the conversion of the UDP to UDP-glucose in the presence of sucrose (see FIG. 10). Thus, for a glycosylation reaction utilizing UDP-glucose (such as those catalyzed by the UGTs), SUS can be used to regenerate UDP-glucose from UDP, enhancing the efficiency of such reaction.

The nucleotide sequence encoding any suitable sucrose synthase may be incorporated into the at least one expression cassette without limitation. In general, sucrose synthases are classified as glycosyltransferase, with the systematic name NDP-glucose:D-fructose 2-alpha-D-glucosyltransferase. Non-limiting examples of other names used to describe sucrose synthases include: UDP glucose-fructose glucosyltransferase, sucrose synthetase, sucrose-UDP glucosyltransferase, sucrose-uridine diphosphate glucosyltransferase, and uridine diphosphoglucose-fructose glucosyltransferase.

In one aspect, suitable sucrose synthases include, but are not limited to those derived from *Arabidopsis thaliana* and *Vigna radiate* SUS genes, or from any gene that encodes a functional homolog of the sucrose synthase encoded by the *Arabidopsis thaliana* and *Vigna radiate* SUS1 sequence, or the functional homologs thereof. Non-limiting examples of suitable sucrose synthases include: an *Arabidopsis* sucrose synthase 1; an *Arabidopsis* sucrose synthase 3; and a *Vigna radiate* sucrose synthase (mbSUS1). In one aspect, the sucrose synthase may be an mbSUS1 enzyme with an amino acid sequence of SEQ ID NO:11.

In this one aspect, the at least one expression cassette may include a nucleotide sequence encoding the mbSUS1 enzyme that includes a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:12. Suitably, the nucleotide sequence encoding the mbSUS1 enzyme may have an amino acid sequence that has at least 80% sequence identity to the amino acid sequence set forth in SEQ ID NO:11. More suitably, the nucleotide sequence may encode a mbSUS1 enzyme with an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:11. The nucleotide sequence encoding the mbSUS1 enzyme thus includes those nucleotide sequences encoding functional fragments of SEQ ID NO:11, functional variants of SEQ ID NO:11, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:11. As known by those skilled in the art, the nucleic acid sequence encoding the mbSUS1 enzyme can be codon optimized for expression in a suitable host organism such as, for example, bacteria or yeast.

Expression Cassettes

In various aspects, the at least one nucleotide sequence encoding at least one enzyme as described above are incorporated into at least one expression cassette that is introduced into the host cell in order to produce the transformed host cell used as a whole-cell catalyst. Any expression cassette, expression plasmid, expression vector, or any other known means of introducing foreign genetic material into a host cell may be selected for use as the at least expression cassette of the whole-cell catalyst. In an aspect, the expression cassette may be selected based in any one or more of at least several factors including, but not limited to: compatibility with the type of host cell, efficiency of expression, ease of use, and any other relevant factor.

For microbial host cells including, but not limited to bacteria cells and yeast cells, microbial host cell expression systems and expression vectors containing regulatory sequences that direct high level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. Molecular and App. Gen., 1:483 498 (1982), the entirety of which is hereby incorporated herein to the extent it is consistent herewith), and the promoter of the chlorophyll a/b binding protein. These two promoters are known to be light-induced in plant cells (see, for example, Genetic Engineering of Plants, an Agricultural Perspective, A. Cashmore, Plenum, N.Y. (1983), pages 29 38; Coruzzi, G. et al., The Journal of Biological Chemistry, 258:1399 (1983), and Dunsmuir, P. et al., Journal of Molecular and Applied Genetics, 2:285 (1983), each of which is hereby incorporated herein by reference to the extent they are consistent herewith).

The choice of plasmid vector depends upon the method that will be used to transform host plants. The skilled artisan is well aware of the genetic elements that must be present on the plasmid vector in order to successfully transform, select and propagate host cells containing the chimeric polynucleotide. The skilled artisan will also recognize that different independent transformation events will result in different levels and patterns of expression (Jones et al., EMBO J. 4:2411 2418 (1985); De Almeida et al., Mol. Gen. Genetics 218:78 86 (1989), each of which is hereby incorporated herein by reference to the extent they are consistent herewith), and thus that multiple events must be screened in order to obtain lines displaying the desired expression level and pattern. Such screening may be accomplished by Southern analysis of DNA blots, Northern analysis of mRNA expression, Western analysis of protein expression, or phenotypic analysis.

Introduction of the expression vector of the subject technology into a plant cell can be performed by a variety of methods known to those of ordinary skill in the art including insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a polynucleotide of interest can be performed by agro-infiltration methods. In this regard, a suspension of *Agrobacterium tumefaciens* containing a polynucleotide of interest can be grown in culture and then injected into a plant by placing the tip of a syringe against the underside of a leaf while gentle counter-pressure is applied to the other side of the leaf. The *Agrobacterium* solution is then injected into the airspaces inside the leaf through stomata. Once inside the leaf, the *Agrobacterium* transforms the gene of interest to a portion of the plant cells where the gene is then transiently expressed.

As another example, transformation of a plasmid of interest into a plant cell can be performed by particle gun bombardment techniques (i.e., biolistics). In this regard, a suspension of plant embryos can be grown in liquid culture and then bombarded with plasmids or polynucleotides that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

Host cells can be unmodified cells or cell lines, or cell lines that have been genetically modified. In some embodiments, the host cell is a cell line that has been modified to allow for growth under desired conditions, such as at a lower temperature.

Standard recombinant DNA methodologies may be used to obtain a nucleic acid that encodes a recombinant polypeptide described herein, incorporate the nucleic acid into an expression vector, and introduce the vector into a host cell, such as those described in Sambrook, et al. (eds.), Molecular Cloning; A Laboratory Manual, Third Edition, Cold Spring Harbor, (2001); and Ausubel, F. M. et al. (eds.) Current Protocols in Molecular Biology, John Wiley & Sons (1995). A nucleic acid encoding a polypeptide may be inserted into an expression vector or vectors such that the nucleic acids are operably linked to transcriptional and translational control sequences (such as a promoter sequence, a transcription termination sequence, etc.). The expression vector and expression control sequences are generally chosen to be compatible with the expression host cell used.

The expression of polypeptide in a host described herein can be further improved by codon-optimization. For example, modifying a less-common codon with a more common codon may affect the half-life of the mRNA or alter its structure by introducing a secondary structure that interferes with translation of the message. All or a portion of a coding region can be optimized. In some cases the desired modulation of expression is achieved by optimizing essentially the entire gene. In other cases, the desired modulation will be achieved by optimizing part of, but not the entire, sequence of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria may include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

In certain embodiments, the codon optimized nucleic acid sequence can express its protein, at a level which is about 110%, about 150%, about 200%, about 250%, about 300%, about 350%, about 400%, about 450%, or about 500%, of that expressed by a nucleic acid sequence that has not been codon optimized.

In addition to the nucleic acid that encodes the recombinant polypeptide of the subject technology, the expression vector of the subject technology may additionally carry regulatory sequences that control the expression of the protein in a host cell, such as promoters, enhancers or other expression control elements that control the transcription or translation of the nucleic acid(s). Such regulatory sequences are known in the art. It will be appreciated by those skilled in the art that the design of the expression vector, including the selection of regulatory sequences may depend on such factors as the choice of the host cell to be transformed, the level of expression of protein desired, etc. In addition, the recombinant expression vectors of the subject technology may carry additional sequences, such as sequences that regulate replication of the vector in host cells (e.g., origins of replication) and selectable marker genes.

In various aspects, the at least one expression cassette may include at least one nucleotide sequence encoding at least one enzyme including, but not limited to a uridine dipospho glycosyltransferase (UDP-glycosyltransferase or UGT) and a sucrose synthase (SUS) as described herein above. In one aspect, the at least one expression cassette may include a first expression cassette that includes at least one UGT sequence and a second expression cassette that includes at least one SUS sequence. In another aspect, the at least one expression cassette may include one expression cassette that includes both the at least one UGT sequence and the at least one USU sequence.

In various other aspects, the degree of expression of the UGT and/or SUS sequences may be modulated by the incorporation of multiple copies of the UGT sequences and/or multiple copies of the SUS sequences. In one aspect, the at least one expression cassette used to transform the host cell may include a single expression cassette that includes multiple copies of a UGT sequence and/or multiple copies of an SUS sequence. In another aspect, the at least one expression cassette may include multiple copies of a first cassette that includes a single copy of a UGT sequence and multiple copies of a second cassette that includes a single copy of a SUS sequence.

In one aspect, the at least one expression cassette may include one copy of a UGT76G1 nucleotide sequence (SEQ ID NO: 10) encoding the UGT76G1 enzyme (SEQ ID NO: 9). In other aspects, the at least one expression cassette may include two copies of the UGT76G1 nucleotide sequence, three copies of the UGT76G1 nucleotide sequence, four copies of the UGT76G1 nucleotide sequence, five copies of the UGT76G1 nucleotide sequence, six copies of the UGT76G1 nucleotide sequence, seven copies of the UGT76G1 nucleotide sequence, eight copies of the UGT76G1 nucleotide sequence, nine copies of the UGT76G1 nucleotide sequence, or ten copies of the UGT76G1 nucleotide sequence.

In one aspect, the at least one expression cassette may include one copy of a HV1 nucleotide sequence (SEQ ID NO: 8) encoding the HV1 enzyme (SEQ ID NO: 7). In other aspects, the at least one expression cassette may include two copies of the HV1 nucleotide sequence, three copies of the HV1 nucleotide sequence, four copies of the HV1 nucleotide sequence, five copies of the HV1 nucleotide sequence, six copies of the HV1 nucleotide sequence, seven copies of the HV1 nucleotide sequence, eight copies of the HV1 nucleotide sequence, nine copies of the HV1 nucleotide sequence, or ten copies of the HV1 nucleotide sequence.

In one aspect, the at least one expression cassette may include one copy of a UGT76G1-GCW61 nucleotide sequence (SEQ ID NO: 4) encoding the UGT76G1 enzyme fused with the GCW61 cell wall protein (SEQ ID NO: 3). In other aspects, the at least one expression cassette may include two copies of the UGT76G1-GCW61 nucleotide sequence, three copies of the UGT76G1-GCW61 nucleotide sequence, four copies of the UGT76G1-GCW61 nucleotide sequence, five copies of the UGT76G1-GCW61 nucleotide sequence, six copies of the UGT76G1-GCW61 nucleotide sequence, seven copies of the UGT76G1-GCW61 nucleotide sequence, eight copies of the UGT76G1-GCW61 nucleotide sequence, nine copies of the UGT76G1-GCW61 nucleotide sequence, or ten copies of the UGT76G1-GCW61 nucleotide sequence.

In one aspect, the at least one expression cassette may include one copy of a HV1-GCW61 nucleotide sequence (SEQ ID NO: 2) encoding the HV1-GCW61 enzyme (SEQ ID NO: 1). In other aspects, the at least one expression cassette may include two copies of the HV1-GCW61 nucleotide sequence, three copies of the HV1-GCW61 nucleotide sequence, four copies of the HV1-GCW61 nucleotide sequence, five copies of the HV1-GCW61 nucleotide sequence, six copies of the HV1-GCW61 nucleotide sequence, seven copies of the HV1-GCW61 nucleotide sequence, eight copies of the HV1-GCW61 nucleotide sequence, nine copies of the HV1-GCW61 nucleotide sequence, or ten copies of the HV1-GCW61 nucleotide sequence.

In one aspect, the at least one expression cassette may include one copy of an mbSUS1 nucleotide sequence (SEQ ID NO:12) encoding the mbSUS1 enzyme (SEQ ID NO:11). In other aspects, the at least one expression cassette may include two copies of the mbSUS1 nucleotide sequence, three copies of the mbSUS1 nucleotide sequence, four copies of the mbSUS1 nucleotide sequence, five copies of the mbSUS1 nucleotide sequence, six copies of the mbSUS1 nucleotide sequence, seven copies of the mbSUS1 nucleotide sequence, eight copies of the mbSUS1 nucleotide sequence, nine copies of the mbSUS1 nucleotide sequence, or ten copies of the mbSUS1 nucleotide sequence.

In one aspect, an expression cassette may include one or more copies of a nucleotide sequence encoding a single UGT sequence encoding a UGT enzyme selected from UGT76G1, HV1, or EUGT11 as described herein above. In another aspect, an expression cassette may include one or more copies of two or more UGT enzymes selected from UGT76G1, HV1, EUGT11, and any combination thereof. In this other aspect, the transformed host cell may express two or more types of UGT enzymes according to need.

In one aspect, the expression vector may contain multiple expression cassettes, in which each expression cassette contains a single copy of a nucleotide sequence encoding a single UGT sequence encoding a UGT enzyme selected from UGT76G1, HV1, or EUGT11 as described herein above, or a single mbSUS1 sequence encoding the mbSUS1 enzyme. After transformation, the multiple expression cassettes may be integrated into the genome of the transformed host cell.

Method of Producing Steviol Glycosides

In various aspects the whole-cell catalysts described herein above may be used to produce a desired steviol glycoside compound from a substrate according to a method as disclosed herein. FIG. 11 is a block diagram illustrating a method of producing a steviol glycoside compound using the whole-cell catalyst in one aspect. Referring to FIG. 11, the method includes inducing expression of the nucleotide sequences encoding the at least one UGT enzyme (UGT76G1, HV1, and/or EUGT11) and the SUS enzyme (mbSUS1) in the transformed host cell at step 1102. The expression of the UGT and SUS sequences results in a whole-cell catalyst characterized by a plurality of UGT enzymes displayed on the cell surface and an amount of intracellular SUS enzyme within the whole-cell catalyst.

Referring again to FIG. 11, the method further includes cultivating the whole-cell catalysts within a culture medium that includes a steviol glycoside substrate, UDP or UDP-glucose, and an amount of sucrose at step 1104. As described herein previously the UGT enzyme catalyzes a glycosylation of the substrate to produce the desired steviol glycoside compound. Over time, the substrate contained within the culture medium is converted to the desired steviol glycoside compound, which is also contained within the culture medium.

FIG. 10 illustrates exemplary reactions that may be catalyzed by the whole-cell catalyst within the culture medium according to the method. In Reaction 1, the substrate within the culture medium (Reb A) may be glycosylated to produce Reb D, as catalyzed by the UGT enzyme using UDP-glucose as a donor compound. In Reaction 2, the UDP by-product of Reaction 1 may be combined with sucrose in the culture medium to regenerate additional UDP-glucose for use in the additional production of Reb D according to Reaction 1.

Referring again to FIG. 11, after a residence time in the culture medium sufficient to produce the desired steviol glycoside compound, at least a portion of the desired steviol glycoside compound may be separated from the cell culture containing the whole-cell catalysts at step 1106. Any known method of separating a protein from an aqueous solution may be used without limitation. In one non-limiting example, the desired steviol glycoside compound may be separated from the cell culture using high-performance liquid chromatography (HPLC) methods.

The transformed host cells that are induced in step 1102 may be any of the transformed host cells produced using any of the materials and methods described herein above. The method of inducing the transformed host cell may vary depending on any one or more of at least several factors including, but not limited to: the type of host cell, the promoter or promoters including in the at least one expression cassette incorporated into the host cell, and any other relevant factor. By way of non-limiting example, if the transformed host cell is a transformed Pichia pastoris strain in which the introduced expression cassette included an AOX1 promoter may be induced by an amount of methanol sufficient to induce expression via the AOX1 promoter according to known methods. The transformed host cell may be induced for any suitable time period without limitation to ensure that sufficient amounts of the at least one UGT enzyme and the SUS enzyme are produced. In various aspects, the transformed host cells may be induced to express the UGT and SUS enzymes for at least 1 hour, at least 2 hours, at least 4 hours, at least 6 hours, at least 8 hours, at least 10 hours, at least 12 hours, at least 16 hours, at least 20 hours, at least 24 hours, at least 30 hours, at least 36 hours, at least 42 hours, at least 48 hours, at least 60 hours, or at least 72 hours.

In an aspect, the whole-cell catalysts resulting from step 1102 may be transferred into a culture medium containing the substrate to be glycosylated to produce the desired steviol glycoside compound according to reactions described herein above. In an aspect, whole-cell catalysts may be introduced to an in vitro reaction system containing the culture medium. Any known in vitro reaction system and culture medium may be used in the method as described herein without limitation. In one aspect, the in vitro reaction system and culture medium may be selected based on any one or more of at least several factors including, but not limited to: the type of host cell, the scale of production of the desired steviol glycoside compound, the particular glycosylation reaction to be catalyzed by the whole-cell catalyst, and any other relevant factor. By way of non-limiting example, if the whole-cell catalyst is a transformed Pichia cell as described herein above, the transformed Pichia cells may be suspended in a shaking incubator or fermentator within the culture medium containing the substrate.

Any known culture medium may be used to cultivate the whole-cell catalysts with the substrate without limitation. In various aspects, the composition of the culture medium may vary depending on any one or more of at least several factors including, but not limited to: the type of host cell, the particular glycosylation reaction to be catalyzed by the whole-cell catalyst, and any other relevant factor. In one aspect, the culture medium may include the substrate, sucrose, UDP-glucose, and UDP. In another aspect, the culture medium may include additional compounds to maintain the viability of the whole-cell catalysts or otherwise facilitate the production of the desired steviol glycoside compound. Non-limiting examples of suitable additional compounds include potassium phosphate buffer, a pH-adjusting compound such as an acid or base, $MgCl_2$, and any other suitable additional compound.

The whole-cell catalyst may be incubated with the culture medium containing the substrate for any suitable time period without limitation to ensure that sufficient amounts of the desired steviol glycoside compound are produced. In various aspects, the whole-cell catalyst may be incubated within the culture medium for at least 1 hour, at least 2 hours, at least 4 hours, at least 6 hours, at least 8 hours, at least 10 hours, at least 12 hours, at least 16 hours, at least 20 hours, at least 24 hours, at least 30 hours, at least 36 hours, at least 42 hours, at least 48 hours, at least 60 hours, or at least 72 hours.

The substrate included within the culture medium in step 1104 of the method may be selected depending on the type of UGT enzyme and the particular steviol glycoside compound to be produced. In one aspect, the substrate may be selected from any one or more of: rubusoside, rebaudioside KA, stevioside, rebaudioside A, rebaudioside D, and rebaudioside E. Referring to FIGS. 9A, 9B, 9C, 9D, 9E, 9F, 9G, and 9H, these substrates may be glycosylated according to any one or more of the reactions schematically illustrated to produce the desired steviol glycoside compound including, but not limited to: rebaudioside KA, rebaudioside A, rebaudioside D, rebaudioside E, and rebaudioside M. Specific combinations of substrate and whole-cell catalysts that may be used in the method as disclosed are described in more detail herein below.

Method of Producing Rebaudioside a from Stevioside.

The method as disclosed may be used to synthesize rebaudioside A from a stevioside substrate. The method includes culturing induced cells expressing an amount of UDP-glycosyltransferase (UGT76G1) and an amount of sucrose synthase (mbSUS1) with the stevioside substrate for a sufficient time to produce rebaudioside A, wherein a glucose is covalently coupled to the stevioside to produce the rebaudioside A according to reaction 1 of FIGS. 9A, 9B, 9C, 9D, 9E, 9F, 9G, and 9H. In an aspect, the whole-cell catalyst may be the induced G/K4S2 strain of Pichia pastoris and the culture medium may further include: potassium phosphate buffer, $MgCl_2$, sucrose, UDP or UDP-glucose, and any combination thereof.

Method of Producing Rebaudioside M from Rebaudioside D.

The method as disclosed may be used to synthesize rebaudioside M from a rebaudioside D substrate. The method includes culturing induced cells expressing an amount of UDP-glycosyltransferase (UGT76G1) and an amount of sucrose synthase (mbSUS1) with the rebaudioside D substrate for a sufficient time to produce rebaudioside M substrate, wherein a glucose is covalently coupled to the rebaudioside D to produce the rebaudioside M according to reaction 3 of FIGS. 9A, 9B, 9C, 9D, 9E, 9F, 9G, and 9H. In an aspect, the whole-cell catalyst may be the induced G/K4S2 strain of Pichia pastoris and the culture medium may further include: potassium phosphate buffer, $MgCl_2$, sucrose, UDP or UDP-glucose, and any combination thereof.

Method of Producing Rebaudioside D from Rebaudioside E.

The method as disclosed may be used to synthesize rebaudioside D from a rebaudioside E substrate. The method includes culturing induced cells expressing an amount of UDP-glycosyltransferase (UGT76G1) and an amount of sucrose synthase (mbSUS1) with the rebaudioside E substrate for a sufficient time to produce rebaudioside D, wherein a glucose is covalently coupled to the rebaudioside E to produce the rebaudioside D according to reaction 2 of FIGS. 9A, 9B, 9C, 9D, 9E, 9F, 9G, and 9H. In an aspect, the whole-cell catalyst may be the G/K4S2 strain of *Pichia pastoris* and the culture medium may further include: potassium phosphate buffer, $MgCl_2$, sucrose, UDP or UDP-glucose, and any combination thereof.

Method of Producing Rebaudioside D from Rebaudioside A.

The method as disclosed may be used to synthesize rebaudioside D from a rebaudioside A substrate. The method includes culturing induced cells expressing an amount of UDP-glycosyltransferase (HV1) and an amount of sucrose synthase (mbSUS1) with the rebaudioside A substrate for a sufficient time to produce rebaudioside D, wherein a glucose is covalently coupled to the rebaudioside A to produce the rebaudioside D according to reaction 4 of FIGS. 9A, 9B, 9C, 9D, 9E, 9F, 9G, and 9H. In an aspect, the whole-cell catalyst may be the G/H5S2 strain of *Pichia pastoris* and the culture medium may further include: potassium phosphate buffer, $MgCl_2$, sucrose, UDP or UDP-glucose, and any combination thereof.

Method of Producing Rebaudioside E from Stevioside.

The method as disclosed may be used to synthesize rebaudioside E from a stevioside substrate. The method includes culturing induced cells expressing an amount of UDP-glycosyltransferase (HV1) and an amount of sucrose synthase (mbSUS1) with the stevioside substrate for a sufficient time to produce rebaudioside E, wherein a glucose is covalently coupled to the stevioside to produce the rebaudioside E according to reaction 5 of FIGS. 9A, 9B, 9C, 9D, 9E, 9F, 9G, and 9H. In an aspect, the whole-cell catalyst may be the G/H5S2 strain of *Pichia pastoris* and the culture medium may further include: potassium phosphate buffer, $MgCl_2$, sucrose, UDP or UDP-glucose, and any combination thereof.

Method of Producing Rebaudioside M from Stevioside and/or Rebaudioside A.

The method as disclosed may be used to synthesize rebaudioside M from a stevioside and/or rebaudioside A substrate. The method includes culturing induced cells that include a first induced cell expressing an amount of UDP-glycosyltransferase (UGT76G1) and an amount of sucrose synthase (mbSUS1); and a second induced cell expressing an amount of UDP-glycosyltransferase (HV1) and an amount of sucrose synthase (mbSUS1) with the stevioside and/or rebaudioside A substrate(s) for a sufficient time to produce rebaudioside M, wherein a glucose is covalently coupled to the stevioside and/or rebaudioside A to produce the rebaudioside M according to reactions 5, 2 and 3 and/or 1, 4, and 3 of FIGS. 9A, 9B, 9C, 9D, 9E, 9F, 9G, and 9H. In an aspect, the first induced cell may be the G/K4S2 strain of *Pichia pastoris*, the second induced cell may be the G/H5S2 strain of *Pichia pastoris*, and the culture medium may further include: potassium phosphate buffer, $MgCl_2$, sucrose, UDP or UDP-glucose, and any combination thereof.

Method of Producing Rebaudioside E from Rebaudioside KA.

The method as disclosed may be used to synthesize rebaudioside E from a rebaudioside KA substrate. The method includes culturing induced cells expressing an amount of UDP-glycosyltransferase (HV1) and an amount of sucrose synthase (mbSUS1) with the rebaudioside KA substrate for a sufficient time to produce rebaudioside E, wherein a glucose is covalently coupled to the rebaudioside KA to produce the rebaudioside E according to reaction 6 of FIGS. 9A, 9B, 9C, 9D, 9E, 9F, 9G, and 9H. In an aspect, the whole-cell catalyst may be the G/H5S2 strain of *Pichia pastoris* and the culture medium may further include: potassium phosphate buffer, $MgCl_2$, sucrose, UDP or UDP-glucose, and any combination thereof.

Method of Producing Rebaudioside KA and Rebaudioside E from Rubusoside.

The method as disclosed may be used to synthesize rebaudioside KA and rebaudioside E from a rubusoside substrate. The method includes culturing induced cells expressing an amount of UDP-glycosyltransferase (HV1) and an amount of sucrose synthase (mbSUS1) with the rubusoside substrate for a sufficient time to produce rebaudioside KA, wherein a glucose is covalently coupled to the rubusoside to produce the rebaudioside KA according to reaction 7 of FIGS. 9A, 9B, 9C, 9D, 9E, 9F, 9G, AND 9H. Furthermore, a glucose is covalently coupled to rebaudioside KA to produce the rebaudioside E according to reaction 6 of FIGS. 9A, 9B, 9C, 9D, 9E, 9F, 9G, and 9H. In an aspect, the whole-cell catalyst may be the G/H5S2 strain of *Pichia pastoris* and the culture medium may further include: potassium phosphate buffer, $MgCl_2$, sucrose, UDP or UDP-glucose, and any combination thereof.

In one aspect, the reactions conducted to produce the desired steviol glycoside compound may be performed in a batch method, defined herein as introducing a discrete amount of the whole-cell catalysts into the in vitro reactor and removing a discrete amount of culture medium from the in vitro reactor containing the desired steviol glycoside compound. In this aspect, at least one discrete batch of the desired steviol glycoside compound may be produced, or the batch method may be repeated by replacing the culture medium multiple times to produce multiple discrete batches of the desired steviol glycoside compound. In another aspect, the reactions conducted to produce the desired steviol glycoside compound may be performed in a continuous feed method, defined herein as maintaining a colony of the whole-cell catalysts within the in vitro reactor and continuously introducing an amount of culture medium containing the substrate while continuously removing an amount of the culture medium containing the desired steviol glycoside compound. In both aspects, any known methods of batch or continuous feed bioproduction methods may be used without limitation.

In various aspects, for those production methods involving multiple glycosylation reactions, such as the production of rebaudioside M from a stevioside and/or rebaudioside A substrate, all reactions may be conducted within the same in vitro reactor, as described herein above. In another aspect, each of the multiple glycosylation reactions may be conducted in one of at least two interconnected in vitro reactors, wherein the cell culture containing an intermediary product may be transferred from a first reactor to a second reactor.

By way of non-limiting example, the method as disclosed may be used to synthesize rebaudioside M from a stevioside and/or rebaudioside A substrate in three separate in vitro reactors according to reactions 1, 4, and 3 of FIGS. 9A, 9B, 9C, 9D, 9E, 9F, 9G, and 9H. The first reactor may contain a whole-cell catalyst expressing an amount of UDP-glycosyltransferase (UGT76G1) and an amount of sucrose synthase (mbSUS1). The second reactor may contain a whole-cell catalyst expressing an amount of UDP-glycosyltransferase (HV1) and an amount of sucrose synthase (mbSUS1). The third reactor may contain a whole-cell catalyst expressing an amount of UDP-glycosyltransferase (UGT76G1) and an amount of sucrose synthase (mbSUS1). with a culture medium including a stevioside and/or rebaudioside A substrate for a sufficient time to produce rebaudioside M, wherein a glucose is covalently coupled to the stevioside and/or rebaudioside A to produce the rebaudioside M according to reactions 1, 4, and 3 of FIGS. 9A, 9B, 9C, 9D, 9E, 9F, 9G, and 9H. The first reactor may conduct reaction 1 of FIGS. 9A, 9B, 9C, 9D, 9E, 9F, 9G, and 9H to produce rebaudioside A from a stevioside substrate. The second reactor may conduct reaction 4 of FIGS. 9A, 9B, 9C, 9D, 9E, 9F, 9G, and 9H to produce rebaudioside D from rebaudioside A transferred from the first reactor. The third reactor may conduct reaction 3 of FIGS. 9A, 9B, 9C, 9D, 9E, 9F, 9G, and 9H to produce rebaudioside M from rebaudioside D transferred from the second reactor.

By way of non-limiting example, the method as disclosed may be used to synthesize rebaudioside M from a stevioside and/or rebaudioside A substrate in three separate in vitro reactors according to reactions 5, 2, and 3 of FIGS. 9A, 9B, 9C, 9D, 9E, 9F, 9G, and 9H. The first reactor may contain a whole-cell catalyst expressing an amount of UDP-glycosyltransferase (HV1) and an amount of sucrose synthase (mbSUS1). The second reactor may contain a whole-cell catalyst expressing an amount of UDP-glycosyltransferase (UGT76G1) and an amount of sucrose synthase (mbSUS1). The third reactor may contain a whole-cell catalyst expressing an amount of UDP-glycosyltransferase (UGT76G1) and an amount of sucrose synthase (mbSUS1) with a culture medium including a stevioside and/or rebaudioside A substrate for a sufficient time to produce rebaudioside M, wherein a glucose is covalently coupled to the stevioside to produce the rebaudioside M according to reactions 5, 2, and 3 of FIGS. 9A, 9B, 9C, 9D, 9E, 9F, 9G, and 9H. The first reactor may conduct reaction 5 of FIGS. 9A, 9B, 9C, 9D, 9E, 9F, 9G, and 9H to produce rebaudioside E from a stevioside substrate. The second reactor may conduct reaction 2 of FIGS. 9A, 9B, 9C, 9D, 9E, 9F, 9G, and 9H to produce rebaudioside D from rebaudioside E transferred from the first reactor. The third reactor may conduct reaction 3 of FIGS. 9A, 9B, 9C, 9D, 9E, 9F, 9G, and 9H to produce rebaudioside M from rebaudioside D transferred from the second reactor.

In this non-limiting example, each reactor may provide reaction conditions that are individually tuned to enhance the production of each reactor's product. Non-limiting examples of reactions conditions that may be individually tuned include: pH, temperature, stirring, composition of culture medium, density of whole-cell catalysts, and any other relevant reaction condition. In addition, the configuration of each whole-cell catalyst may be individually modulated to enhance the production of each reactor's product. Non-limiting examples of methods of modulating the configuration of each whole-cell catalyst include: modulating the induction period, altering the number of copies of UGT and/or SUS sequences in the at least one expression cassette of the transformed host cell, altering the type of host cell, and any other suitable method.

The disclosure will be more fully understood upon consideration of the following non-limiting Examples.

EXAMPLES

The following examples demonstrate various aspects of the disclosure.

Example 1: Transformation of *Pichia pastoris* to Produce Engineered Whole-Cell Catalyst Strains To demonstrate the transformation of *Pichia pastoris* cells to produce several engineered *Pichia* strains suitable for use as whole-cell catalysts, the following experiments were conducted.

Full-length DNA fragments of candidate UGT genes were synthesized for use in the transformation of the *Pichia pastoris* cells. Specifically, the cDNAs were codon optimized for *Pichia pastoris* expression (Genscript, Piscataway, N.J.) to produce two UDP-glycosyltransferase sequences: HV1 (SEQ ID NO:8) and UGT76G1 (SEQ ID NO:10). A Flag tag was inserted in frame between a nucleotide sequence encoding a factor signal peptide and the nucleotide sequence encoding HV1 (SEQ ID NO: 8) or UGT76G1 (SEQ ID NO:10). In addition, a gene encoding a *Pichia* cell wall protein (GCW61, SEQ ID NO:6) was inserted in frame to the C-terminal of the HV1 or UGT76G1 sequence to produce two fusion genes: a factor signal peptide—Flag-HV1-GCW61 and a factor signal peptide-Flag-UGT76G1-GCW61. The synthesized fusion genes were cloned into pHKA vector, a modified *Pichia* expression vector (pPICZα A, Invitrogen). In addition, the codon optimized sucrose synthase cDNA (mbSUS1, SEQ ID NO:12) was cloned into the *Pichia* expression vector pPICZα A (Invitrogen). In the vector, each expression cassette contains AOX1 promoter, gene and AOX1 transcription terminator.

To generate the multiple copies of the expression cassette, the above constructs were digested with BamHI and BglII. The expression cassette was collected and inserted into BamHI digested plasmids. After digestion analysis, plasmids with 5 copies of HV1 expression cassettes, plasmids with 4 copies of UGT76G1 expression cassettes, and plasmids with 2 copies of mbSUS expression cassettes were identified.

The linearized expression plasmid was transformed into *Pichia pastoris* (GS115) cells using known methods and the expression cassette was integrated into the *Pichia* genome. After screening, the positive strains were identified, as summarized in Table 2.

TABLE 2

Summary of *Pichia pastoris* strains

| Name of strain | Gene(s) | Description |
| --- | --- | --- |
| G/K4S2 | Flag-UGT76G1-GCW61 mbSUS1 | 4 copies of UGT76G1 expression cassettes 2 copies of mbSUS1 expression cassettes |
| H5 | Flag-HV1-GCW61 | 5 copies of HV1 expression cassettes |
| G/H5S2 | Flag-HV1-GCW61 mbSUS1 | 5 copies of HV1 expression cassettes 2 copies of mbSUS1 expression cassettes |

Example 2: Glycosylation of Stevioside to Produce Rebaudioside A Using the Engineered *Pichia pastoris* Strain G/K4S2

To demonstrate the enzymatic production of rebaudioside A by induced G/K4S2 cells using a stevioside substrate, the following experiment was conducted. A single colony of the *Pichia pastoris* strain G/K4S2 was inoculated in BMGY medium in a baffled flask and grown at 28-30° C. in a shaking incubator (250-300 rpm) until the culture reached an OD600 of 2-6 (log-phase growth). The G/K4S2 cells were harvested by centrifuging and resuspended to an OD600 of 1.0 in BMMY medium to induce expression. 100% methanol was added to the BMMY medium to a final concentration of 1% methanol every 24 hours to maintain induction of expression. 72 hours after induction, the G/K4S2 cells were harvested by centrifuging and subjected to glycosylation activity analysis as described herein below.

The induced G/K4S2 cells were assayed for glycosylation activity using stevioside as the substrate. The induced G/K4S2 cells (60 OD) were tested in a 200 µl in vitro reaction system containing 50 mM potassium phosphate buffer, pH 7.2, 3 mM $MgCl_2$, 3 mg/ml stevioside (*Stevia* extract containing 95% stevioside; Blue California, Calif.), 1 mM UDP or UDP-glucose (UDPG), and 250 mM sucrose. The induced G/K4S2 cells were maintained in the reaction system at 28-30° C. for 24 hours, after which the reaction was terminated by adding 1-butanol. Samples from the reaction system were extracted three times with 200 µL 1-butanol. The pooled extracted fraction of the samples was dried and dissolved in 80% methanol for high-performance liquid chromatography (HPLC) analysis.

HPLC analysis was performed using a UPLC Ultimate 3000 System (Dionex, Sunnyvale, Calif.) that included a quaternary pump, a temperature controlled column compartment, an auto sampler and a UV absorbance detector. A Synergi Hydro-RP column (Phenomenex) with guard column was used for the characterization of steviol glycosides in the pooled samples. Acetonitrile in water was used for isocratic elution in the HPLC analysis. The detection wavelength used in the HPLC analysis was 210 nm.

FIG. 2C is a graph summarizing the HPLC detection of the rebaudioside A enzymatically produced by the induced G/K4S2 cells as sampled from the in vitro reaction system 24 hours after the introduction of the induced G/K4S2 cells.

The results of this experiment demonstrated the enzymatic glycosylation of stevioside by induced G/K4S2 cells to produce rebaudioside A.

Example 3: Glycosylation of Rebaudioside D to Produce Rebaudioside M Using the Engineered *Pichia pastoris* Strain G/K4S2

To demonstrate the enzymatic production of rebaudioside M by induced G/K4S2 cells using a rebaudioside D substrate, the following experiment was conducted. Expression was induced in a culture of *Pichia pastoris* strain G/K4S2 for 72 hours and the induced cells were harvested using a method similar to that described for Example 2. The induced G/K4S2 cells were assayed for glycosylation of a rebaudioside D substrate using methods similar to those described for Example 2. The induced G/K4S2 cells (60 OD) were introduced into a 200 µl in vitro reaction system containing 50 mM potassium phosphate buffer, pH 7.2, 3 mM $MgCl_2$, 0.5 mg/ml rebaudioside D (98% purity; Blue California, Calif.), 1 mM UDP or UDPG, and 250 mM sucrose. The induced G/K4S2 cells were maintained in the reaction system at 28-30° C. for 24 hours, after which the reaction was terminated by adding 1-butanol. Samples from the reaction system were extracted and subjected to high-performance liquid chromatography (HPLC) analysis using methods similar to those described in Example 2.

Figure 1A:
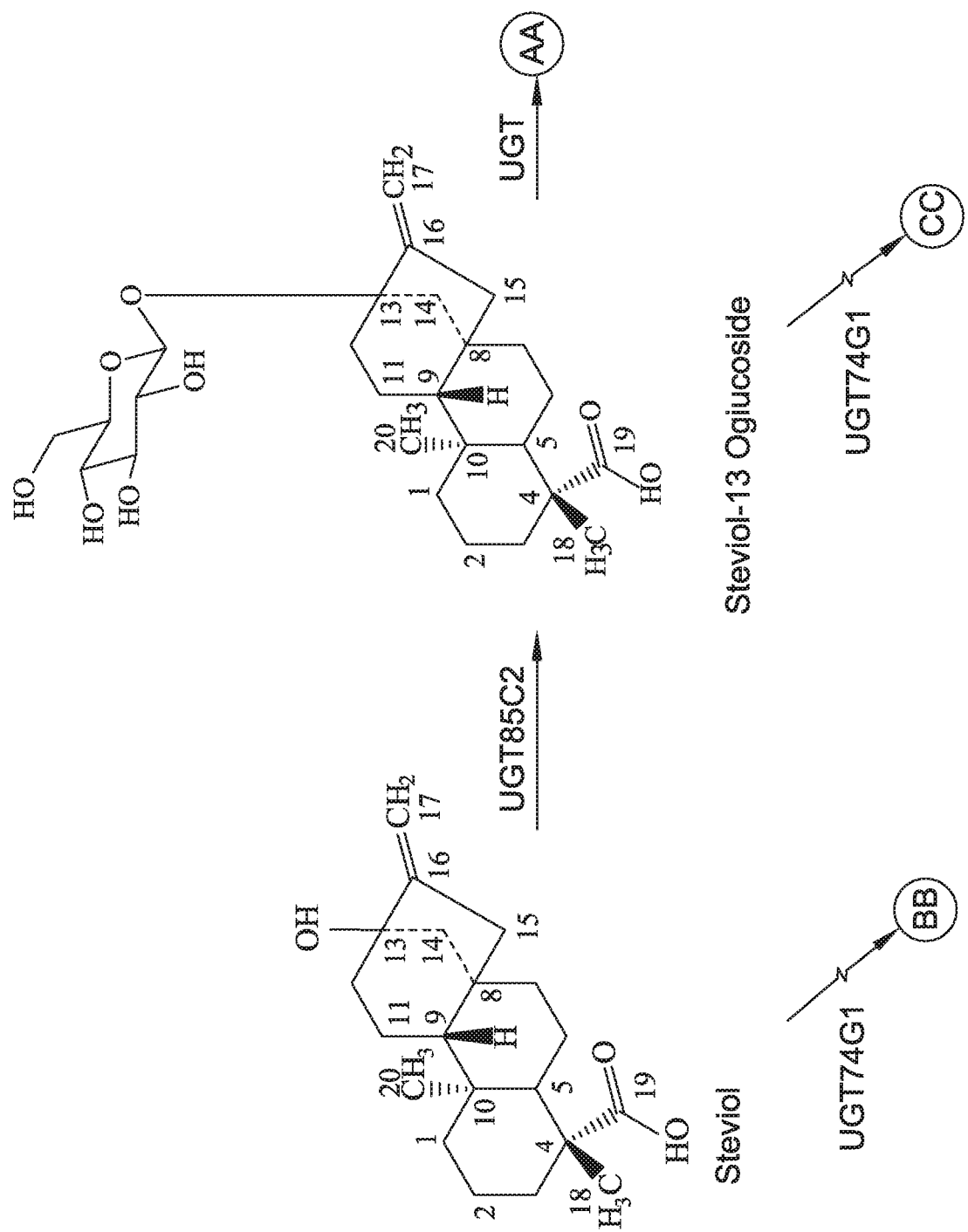
Figure 1B:
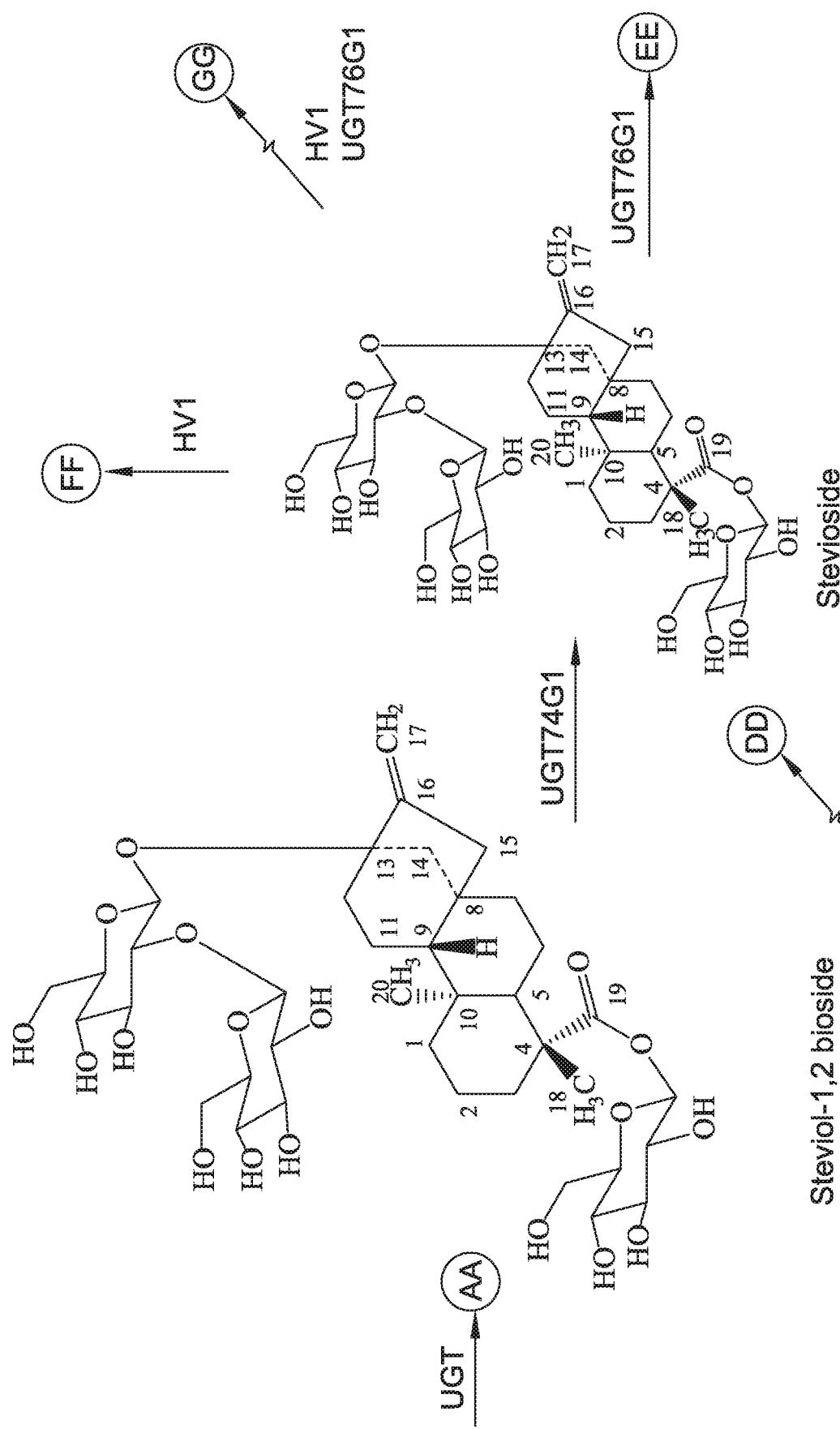
Figure 1C:
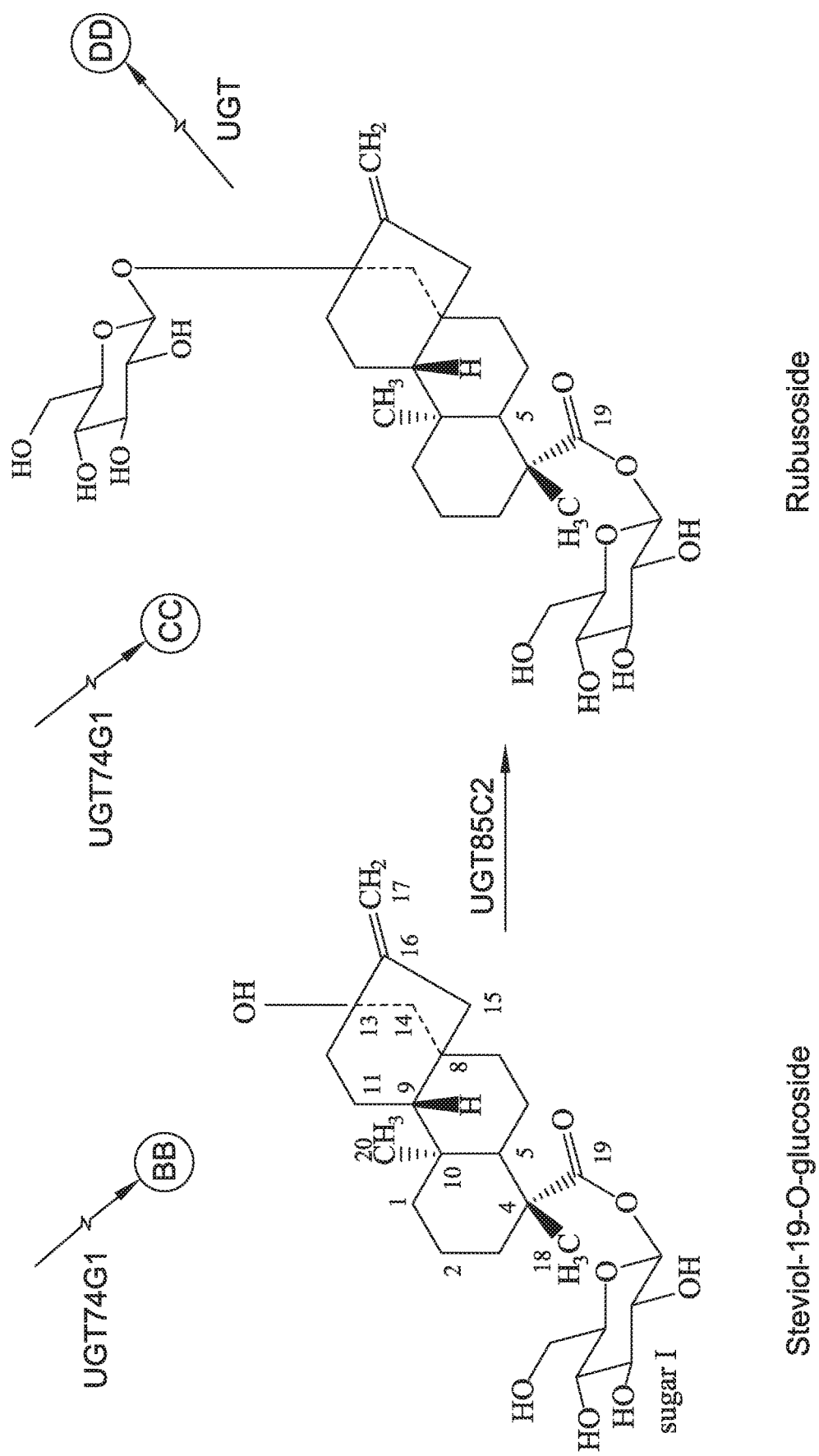
Figure 1E:
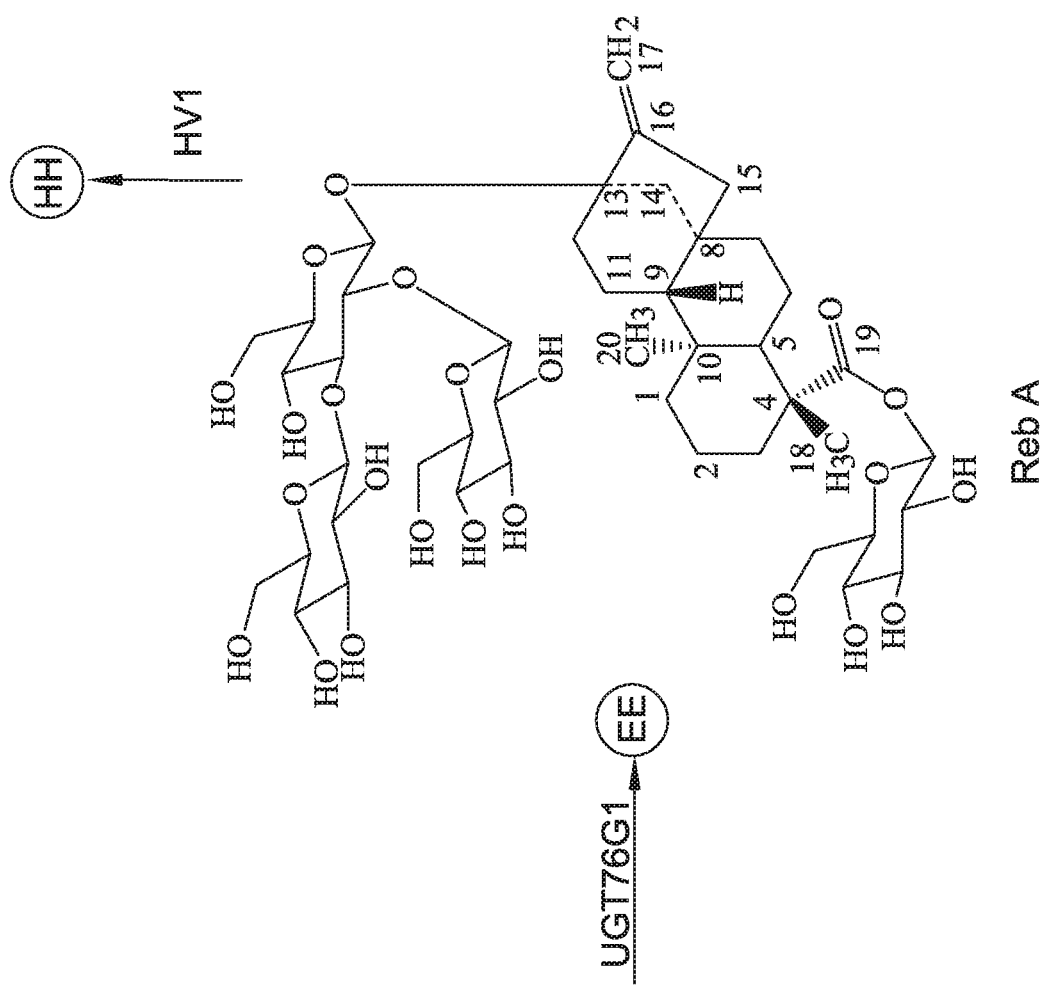
Figure 3A:
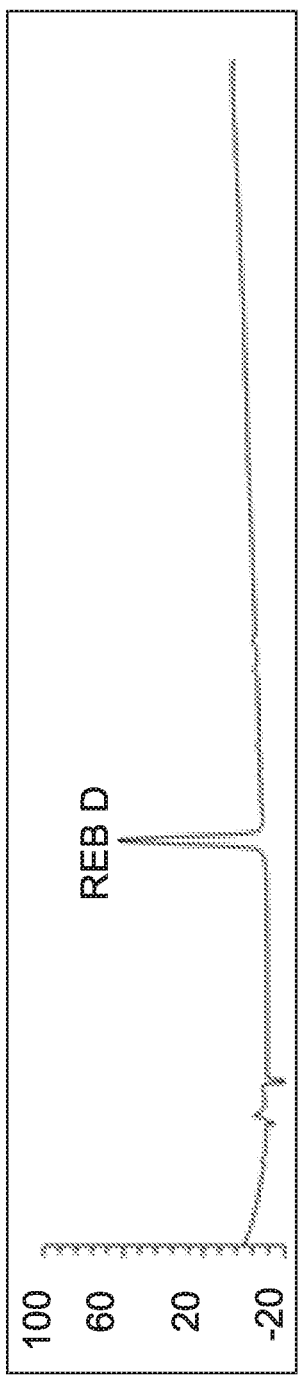
FIGS. 3A, 3B, and 3C summarize the production of rebaudioside M ("Reb M") from rebaudioside D ("Reb D") using cultured G/K4S2 cells.
Figure 3B:
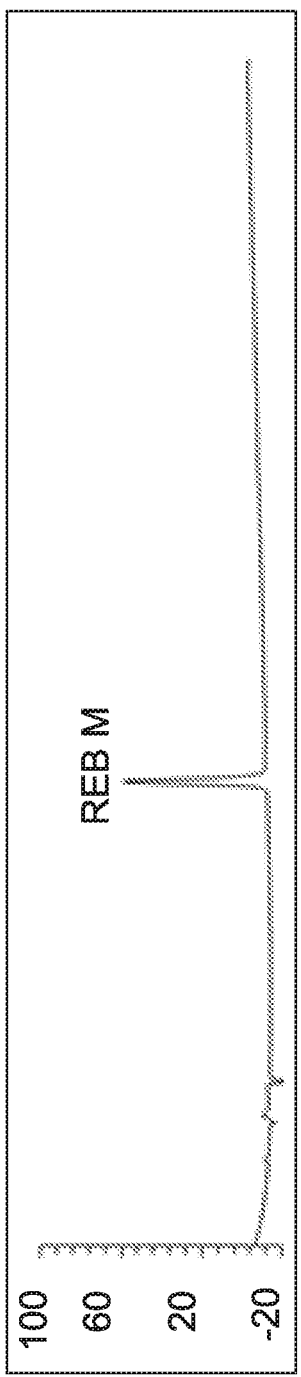
Figure 3C:
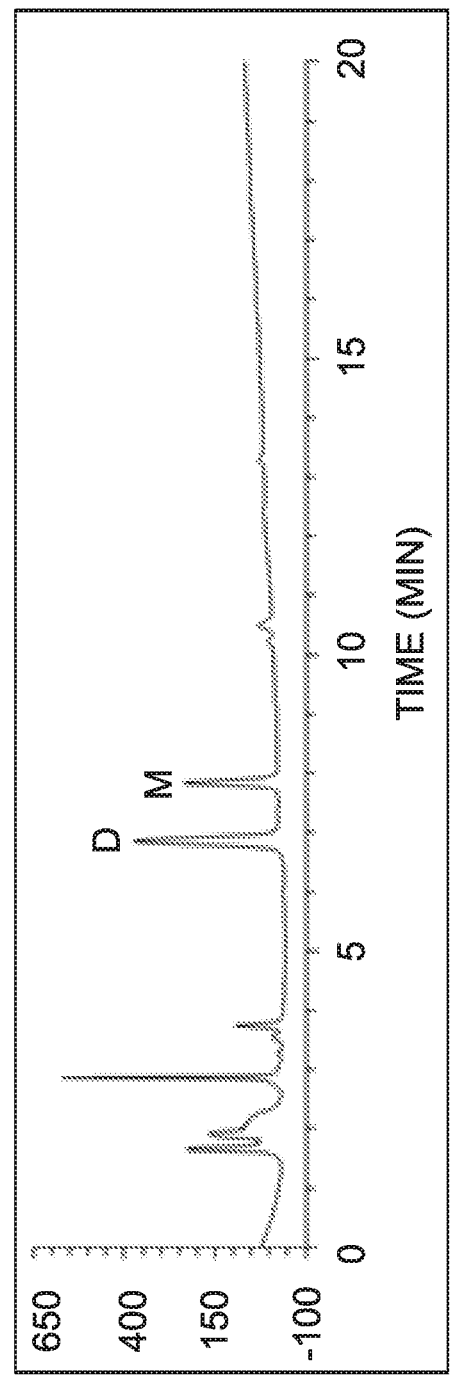

FIG. 3C is a graph summarizing the HPLC detection of the rebaudioside M enzymatically produced by the induced G/K4S2 cells as sampled from the in vitro reaction system 24 hours after the introduction of the induced G/K4S2 cells.

The results of this experiment demonstrated the enzymatic glycosylation of rebaudioside D by induced G/K4S2 cells to produce rebaudioside M.

Example 4: Glycosylation of Rebaudioside E to Produce Rebaudioside D Using the Engineered *Pichia pastoris* Strain G/K4S2

To demonstrate the enzymatic production of rebaudioside D by induced G/K4S2 cells using a rebaudioside E substrate, the following experiment was conducted. Expression was induced in a culture of the *Pichia pastoris* strain G/K4S2 for 72 hours and the induced cells were harvested using a method similar to that described for Example 2. The induced G/K4S2 cells were assayed for glycosylation of a rebaudioside E substrate using methods similar to those described for Example 2. The induced G/K4S2 cells (60 OD) were tested in a 200 µl in vitro reaction system containing 50 mM potassium phosphate buffer, pH 7.2, 3 mM $MgCl_2$, 3 mg/ml rebaudioside E (95% Blue California, Calif.), 1 mM UDP or UDPG, and 250 mM sucrose. The induced G/K4S2 cells were maintained in the reaction system at 28-30° C. for 24 hours, after which the reaction was terminated by adding 1-butanol. Samples from the reaction system were extracted and subjected to high-performance liquid chromatography (HPLC) analysis using methods similar to those described in Example 2.

FIG. 4C is a graph summarizing the HPLC detection of the rebaudioside D enzymatically produced by the induced G/K4S2 cells as sampled from the in vitro reaction system 24 hours after the introduction of the induced G/K4S2 cells.

The results of this experiment demonstrated the enzymatic glycosylation of rebaudioside E by G/K4S2 cells to produce rebaudioside D.

Example 5: Glycosylation of Rebaudioside A to Produce Rebaudioside D Using the Engineered *Pichia pastoris* Strain G/H5 S2

To demonstrate the enzymatic production of rebaudioside D by induced G/H5S2 cells using a rebaudioside A substrate, the following experiment was conducted. Expression was induced in the *Pichia pastoris* strain G/H5S2 for 72 hours and the induced cells were harvested using a method similar to that described for Example 2. The induced G/H5S2 cells were assayed for glycosylation activity using rebaudioside A as the substrate using methods similar to those described for Example 2. The induced G/H5S2 cells (60 OD) were tested in a 200 µl in vitro reaction system containing 50 mM potassium phosphate buffer, pH 7.2, 3 mM $MgCl_2$, 3 mg/ml rebaudioside A (99% Blue California, Calif.), 1 mM UDP or UDPG, and 250 mM sucrose. The induced G/H5S2 cells were maintained in the reaction system at 28-30° C. for 24 hours, after which the reaction was terminated by adding 1-butanol. Samples from the reaction system were extracted and subjected to high-performance liquid chromatography (HPLC) analysis using methods similar to those described in Example 2. For comparison, a similar assay and HPLC analysis was performed for two additional induced *Pichia pastoris* strains: the H5 strain in which only the HV1 sequences were introduced, and the pHKA (control) strain in which empty vectors were introduced.

Figure 5A:
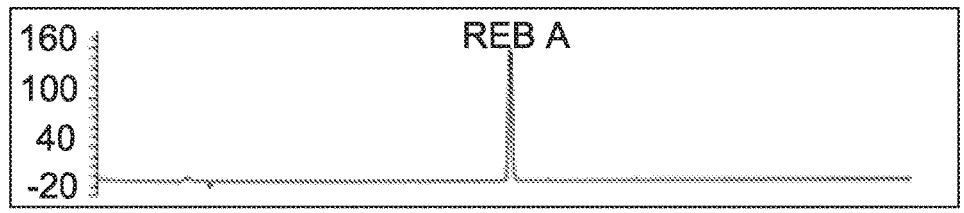
FIGS. 5A, 5B, 5C, 5D, and 5E summarize the production of rebaudioside D ("Reb D") from rebaudioside A ("Reb A") using cultured G/H5S2 cells.
Figure 5B:
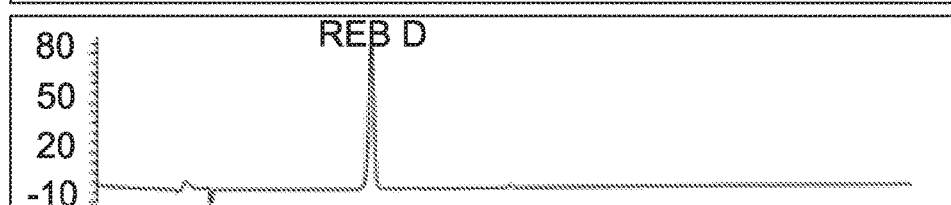
Figure 5C:
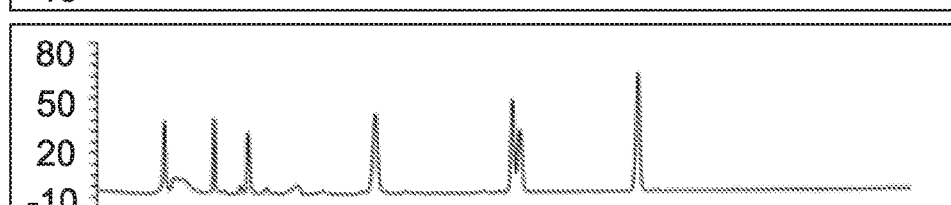
Figure 5D:
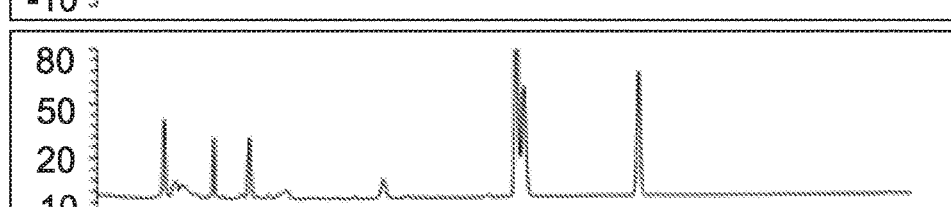
Figure 5E:
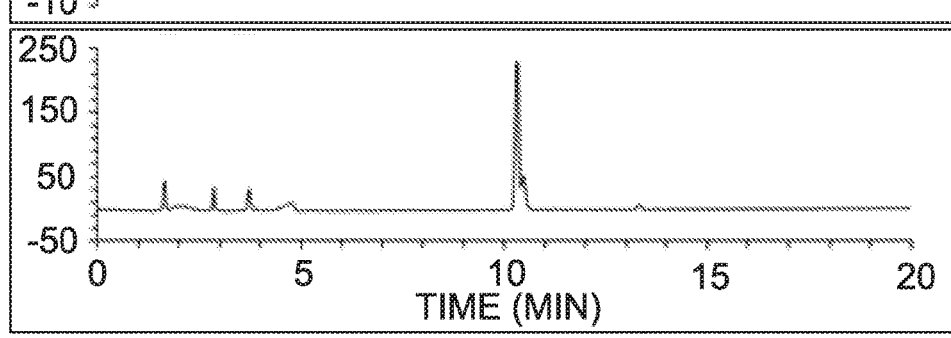

FIGS. 5C, 5D, and 5E are graphs summarizing the HPLC detection of the rebaudioside D enzymatically produced by the induced G/H5S2 cells, induced H5 cells, and induced pHKA cells, respectively, as sampled from the in vitro reaction system 24 hours after the introduction of the induced cells. As illustrated in FIGS. 5C and 5D, both induced G/H5S2 cells (FIG. 5C) and induced H5 cells (FIG. 5D) enzymatically produce rebaudioside D, but the induced G/H5S2 exhibited higher induced G/H5S2 activity, indicating the creation of UGT-SUS coupling system (see FIG. 10) in the induced G/H5S2 cells. As a result of this UGT-SUS coupling system, the induced G/H5S2 cells recycled the expended UDP as illustrated in FIG. 10, whereas additional UDPG was added to the induced H5 cells to enable the production of additional rebaudioside D. No rebaudioside D was enzymatically produced by the induced pHKA cells, demonstrating that rebaudioside D was not produced in the absence of the HV1 sequences.

The results of this experiment demonstrated the enzymatic glycosylation of rebaudioside A by G/H5S2 cells to produce rebaudioside D.

Example 6: Glycosylation of Stevioside to Produce Rebaudioside E Using the Engineered *Pichia pastoris* Strain G/H5 S2

To demonstrate the enzymatic production of rebaudioside E by G/H5S2 cells using a stevioside substrate, the following experiment was conducted. Expression was induced in a culture of the *Pichia pastoris* strain G/H5S2 for 72 hours and the induced cells were harvested using a method similar to that described for Example 2. The induced G/H5S2 cells were assayed for glycosylation activity using stevioside as the substrate using methods similar to those described for Example 2. The induced G/H5S2 cells (60 OD) were tested in a 200 µl in vitro reaction system containing 50 mM potassium phosphate buffer, pH 7.2, 3 mM $MgCl_2$, 3 mg/ml stevioside (95%, Blue California, Calif.), 1 mM UDP or UDPG, and 250 mM sucrose. The induced G/H5S2 cells were maintained in the reaction system at 28-30° C. for 24 hours, after which the reaction was terminated by adding 1-butanol. Samples from the reaction system were extracted and subjected to high-performance liquid chromatography (HPLC) analysis using methods similar to those described in Example 2. For comparison, a similar assay and HPLC analysis was performed for the pHKA (control) strain in which empty vectors were introduced.

Figure 6A:
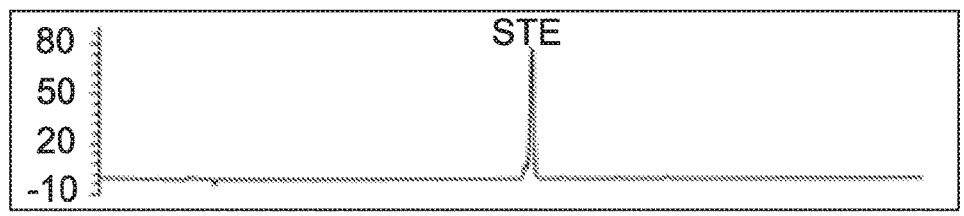
FIGS. 6A, 6B, 6C, and 6D summarize the production of rebaudioside E ("Reb E") from stevioside ("Ste") using cultured G/H5S2 cells.
Figure 6B:
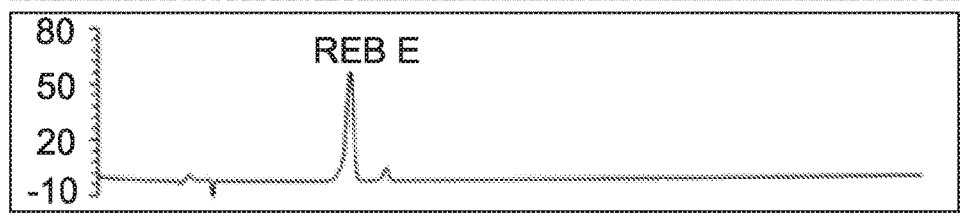
Figure 6C:
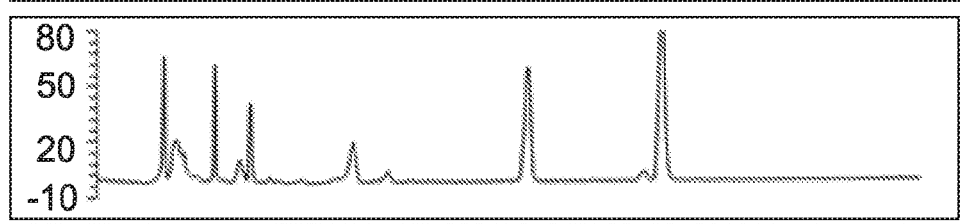
Figure 6D:
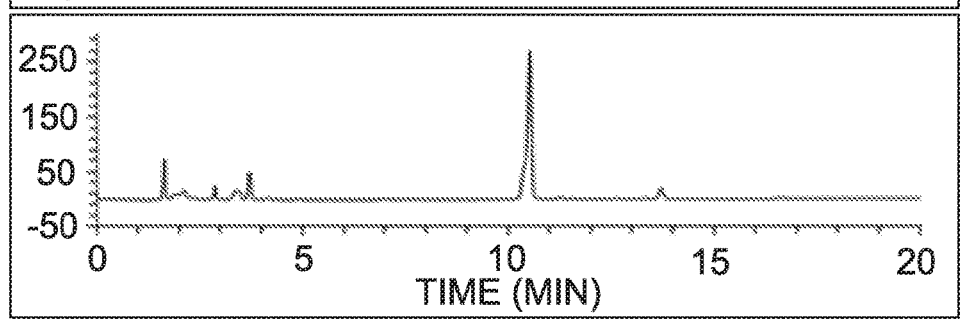

FIGS. 6C and 6D are graphs summarizing the HPLC detection of the rebaudioside E enzymatically produced by the induced G/H5S2 cells and the induced pHKA cells, respectively, as sampled from the in vitro reaction system 24 hours after the introduction of the induced cells. As illustrated in FIG. 6C, the induced G/H5S2 cells enzymatically produce rebaudioside E. As illustrated in FIG. 6D, the induced pHKA cells failed to produce rebaudioside E.

The results of this experiment demonstrated the enzymatic glycosylation of stevioside by G/H5S2 cells to produce rebaudioside E.

Example 7: Glycosylation of Rebaudioside A to Produce Rebaudioside M Using the Engineered *Pichia pastoris* Strains G/H5S2 and G/K4S2

To demonstrate the enzymatic production of rebaudioside M and rebaudioside D by a combination of induced G/K4S2 and induced G/H5S2 cells using a rebaudioside A substrate, the following experiment was conducted. Expression was induced in a culture of the *Pichia pastoris* strains G/K4S2 and G/H5S2 for 72 hours and the induced cells were harvested using a method similar to that described for Example 2. The induced G/K4S2 and G/H5S2 cells were assayed for glycosylation activity using rebaudioside A as the substrate using methods similar to those described for Example 2. The induced G/K4S2 and G/H5S2 cells (60 OD) were tested in a 200 µl in vitro reaction system containing 50 mM potassium phosphate buffer, pH 7.2, 3 mM $MgCl_2$, 1 mg/ml rebaudioside A (99% purity, Blue California, Calif.), 1 mM UDP or UDPG, and 250 mM sucrose. The induced G/K4S2 and G/H5S2 cells were maintained in the reaction system at 28-30° C. for 24 and 48 hours, after which the reaction was terminated by adding 1-butanol. Samples from the reaction system were extracted and subjected to high-performance liquid chromatography (HPLC) analysis using methods similar to those described in Example 2.

FIGS. 7D and 7E are graphs summarizing the HPLC detection of the rebaudioside D and rebaudioside M enzymatically produced by the induced G/K4S2 cells and G/H5S2 cells as sampled from the in vitro reaction system 24 hours (FIG. 7D) and 48 hours (FIG. 7E) after the introduction of the induced G/K4S2 cells and G/H5S2 cells.

The results of this experiment demonstrated the enzymatic glycosylation of rebaudioside A by a combination of induced G/K4S2 and G/H5S2 cells to produce rebaudioside M. Reb D and Reb M was produced by the induced G/K4S2 and G/H5S2 cells, indicating both HV1 and UGT76G1 glycosylation activities in the reaction according to reactions. The G/H5S2 cells initially convert the rebaudioside A substrate to rebaudioside D as illustrated in reaction 4 of FIGS. 9A, 9B, 9C, 9D, 9E, 9F, 9G, and 9H, and the G/K4S2 cells catalyze the conversion of rebaudioside D to rebaudioside M as illustrated in reaction 3 of FIGS. 9A, 9B, 9C, 9D, 9E, 9F, 9G, and 9H.

Example 8: Glycosylation of Rebaudioside A to Produce Rebaudioside M Using the Engineered *Pichia pastoris* Strains G/H5S2 and G/K4S2-Effect of G/H5S2:G/K4S2 Ratio To demonstrate the sensitivity of the enzymatic production of rebaudioside M and rebaudioside D using a rebaudioside A substrate by a combination of induced G/K4S2 cells and induced G/H5S2 cells at different ratios of G/K4S2 and G/H5S2 cells, the following experiment was conducted. The glycosylation activity of a combination of induced G/K4S2 and G/H5S2 cells using rebaudioside A as the substrate was assessed using methods similar to those of Example 7 for several ratios of G/H5S2:G/K4S2 cells: 2:1, 1:1, 1:2 and 1:3. In addition, samples were extracted from the reaction system after reaction times of 16 hr, 24 hr, and 48 hr for each G/H5S2:G/K4S2 cell ratio. All samples were subjected to high-performance liquid chromatography (HPLC) analysis using methods similar to those described in Example 2.

FIGS. 8A and 8B are graphs summarizing the HPLC detection of the rebaudioside D and rebaudioside M, respectively, enzymatically produced by the induced G/K4S2 cells and G/H5S2 cells in various G/H5S2:G/K4S2 cell ratios as sampled from the in vitro reaction system at various times after the introduction of the induced G/K4S2 cells and G/H5S2 cells. As illustrated in FIG. 8A, a higher G/H5S2:G/K4S2 ratio may result in the accumulation of more Reb D.

As illustrated in FIG. 8B, a lower G/H5S2:G/K4S2 ratio may result in the conversion of more Reb D into Reb M.

The results of this experiment demonstrated that the enzymatic glycosylation of rebaudioside A by a combination of G/K4S2 and G/H5S2 cells to produce rebaudioside M was sensitive to the G/H5S2:G/K4S2 cell ratio.

Example 9: Glycosylation of Stevioside to Produce Rebaudioside M Using the Engineered *Pichia pastoris* Strains G/H5S2 and G/K4S2

To demonstrate the enzymatic production of rebaudioside M by a combination of induced G/K4S2 and induced G/H5S2 cells using a stevioside substrate, the following experiment was conducted. Expression was induced in a culture of the *Pichia pastoris* strains G/K4S2 and G/H5S2 for 72 hours and the induced cells were harvested using a method similar to that described for Example 2. The induced G/K4S2 and G/H5S2 cells were assayed for glycosylation activity using stevioside as the substrate using methods similar to those described for Example 2. The induced G/K4S2 and G/H5S2 cells (60 OD) were tested in a 200 μl in vitro reaction system containing 50 mM potassium phosphate buffer, pH 7.2, 3 mM $MgCl_2$, 1 mg/ml stevioside (95% purity, Blue California, Calif.), 1 mM UDP or UDPG, and 250 mM sucrose. The induced G/K4S2 and G/H5S2 cells were maintained in the reaction system at 28-30° C. for 10 and 24 hours, after which the reaction was terminated by adding 1-butanol. Samples from the reaction system were extracted and subjected to high-performance liquid chromatography (HPLC) analysis using methods similar to those described in Example 2.

FIGS. 12C and 12D are graphs summarizing the HPLC detection of the rebaudioside D and rebaudioside M enzymatically produced by the induced G/K4S2 cells and G/H5S2 cells as sampled from the in vitro reaction system 10 hours (FIG. 12C) and 24 hours (FIG. 12D) after the introduction of the induced G/K4S2 cells and G/H5S2 cells.

The results of this experiment demonstrated the enzymatic glycosylation of stevioside by a combination of induced G/K4S2 and G/H5S2 cells to produce rebaudioside M.

Example 10: Glycosylation of Rebaudioside KA to Produce Rebaudioside E Using the Engineered *Pichia pastoris* Strains G/H5S2

To demonstrate the enzymatic production of rebaudioside E by G/H5S2 cells using a rebaudioside KA substrate, the following experiment was conducted. Expression was induced in a culture of the *Pichia pastoris* strain G/H5S2 for 72 hours and the induced cells were harvested using a method similar to that described for Example 2. The induced G/H5S2 cells were assayed for glycosylation activity using rebaudioside KA as the substrate using methods similar to those described for Example 2. The induced G/H5S2 cells (60 OD) were tested in a 200 μl in vitro reaction system containing 50 mM potassium phosphate buffer, pH 7.2, 3 mM $MgCl_2$, 1 mg/ml rebaudioside KA (98%, Blue California, Calif.), 1 mM UDP or UDPG, and 250 mM sucrose. The induced G/H5S2 cells were maintained in the reaction system at 28-30° C. for 24 hours, after which the reaction was terminated by adding 1-butanol. Samples from the reaction system were extracted and subjected to high-performance liquid chromatography (HPLC) analysis using methods similar to those described in Example 2.

FIG. 13B is a graph summarizing the HPLC detection of the rebaudioside E enzymatically produced by the induced G/H5S2, as sampled from the in vitro reaction system 24 hours after the introduction of the induced cells. As illustrated in FIG. 13B, the induced G/H5S2 cells enzymatically produce rebaudioside E.

The results of this experiment demonstrated the enzymatic glycosylation of rebaudioside KA by G/H5S2 cells to produce rebaudioside E.

Example 10: Glycosylation of Rubusoside to Produce Rebaudioside KA and Rebaudioside E Using the Engineered *Pichia pastoris* Strains G/H5S2

To demonstrate the enzymatic production of rebaudioside KA by G/H5S2 cells using a rubusoside substrate, the following experiment was conducted. Expression was induced in a culture of the *Pichia pastoris* strain G/H5S2 for 72 hours and the induced cells were harvested using a method similar to that described for Example 2. The induced G/H5S2 cells were assayed for glycosylation activity using rubusoside as the substrate using methods similar to those described for Example 2. The induced G/H5S2 cells (60 OD) were tested in a 200 μl in vitro reaction system containing 50 mM potassium phosphate buffer, pH 7.2, 3 mM $MgCl_2$, 1 mg/ml rubusoside (98%, Blue California, Calif.), 1 mM UDP or UDPG, and 250 mM sucrose. The induced G/H5S2 cells were maintained in the reaction system at 28-30° C. for 24 hours, after which the reaction was terminated by adding 1-butanol. Samples from the reaction system were extracted and subjected to high-performance liquid chromatography (HPLC) analysis using methods similar to those described in Example 2.

FIGS. 14B and 14C are graphs summarizing the HPLC detection of the rebaudioside KA enzymatically produced by the induced G/H5S2, as sampled from the in vitro reaction system 14 and 24 hours after the introduction of the induced cells. As illustrated in FIGS. 14B and 14C, the induced G/H5S2 cells enzymatically produce rebaudioside KA and rebaudioside E. Produced rebaudioside KA can be converted to rebaudioside E.

The results of this experiment demonstrated the enzymatic glycosylation of rubusoside by G/H5S2 cells to produce rebaudioside KA and rebaudioside E.

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A whole-cell catalyst composition for the production of a steviol glycoside, the whole-cell catalyst composition comprising a first whole-cell catalyst, said first whole-cell catalyst being a *Pichia pastoris* host cell transformed by at least one expression cassette such that the host cell comprises:

(a) at least one first nucleotide sequence encoding a HV1-GCW61 fusion protein in which a display polypeptide is fused to the C-terminal of a UDP-glycosyltransferase (UGT) enzyme such that when expressed the UGT enzyme is attached to the surface of the host cell, wherein the first nucleotide sequence comprises a sequence that is at least 80% identical to the sequence set forth in SEQ ID NO: 2; and (b) at least one second nucleotide sequence encoding an intracellular *sucrose* synthase (SUS).

2. The whole-cell catalyst composition of claim 1, wherein the SUS comprises at least one of: an SUS derived from *Arabidopsis thaliana*, an SUS derived from *Vigna radiate*.

3. The whole-cell catalyst composition of claim 2, wherein the SUS comprises at least one of: *Arabidopsis sucrose* synthase 1; *Arabidopsis sucrose* synthase 3; and *Vigna radiate* sucrose synthase (mbSUS1).

4. The whole-cell catalyst composition of claim 1, wherein the *Pichia pastoris* host cell is transformed to include five copies of the first nucleotide sequence and two copies of the second nucleotide sequence, wherein the second nucleotide sequence comprises the sequence set forth in SEQ ID NO: 12.

5. The whole-cell catalyst composition of claim 1, wherein the whole-cell catalyst composition comprises a second whole-cell catalyst, said second whole-cell catalyst being a *Pichia pastoris* host cell transformed to include four copies of a third nucleotide sequence encoding a UGT76G1-GCW61 fusion protein, wherein the third nucleotide sequence comprises the sequence set forth in SEQ ID NO: 4 and two copies of the second nucleotide sequence, wherein the second nucleotide sequence comprises the sequence set forth in-SEQ ID NO: 12.

6. The whole-cell catalyst composition of claim 1, wherein the first nucleotide sequence comprises the sequence set forth in SEQ ID NO: 2.

7. A method of producing a desired steviol glycoside from a starting steviol glycoside substrate, the method comprising:
   incubating a whole-cell catalyst composition in a culture medium comprising said starting steviol glycoside substrate, sucrose, UDP and/or UDP-glucose for period such that said starting steviol glycoside substrate is converted to the desired steviol glycoside in the culture medium;
   wherein the whole-cell catalyst composition comprises a first whole-cell catalyst, said first whole-cell catalyst being a *Pichia pastoris* host cell transformed by at least one expression cassette such that the host cell comprises:
   (a) at least one first nucleotide sequence encoding a HV1-GCW61 fusion protein in which a display polypeptide is fused to the C-terminal of a UDP-glycosyltransferase (UGT) enzyme such that when expressed the UGT enzyme is attached to the surface of the host cell, wherein the first nucleotide sequence comprises a sequence that is at least 80% identical to the sequence set forth in SEQ ID NO: 2; and
   (b) at least one second nucleotide sequence encoding an intracellular sucrose synthase (SUS).

8. The method of claim 7, wherein the first nucleotide sequence comprises the sequence set forth in SEQ ID NO: 2.

9. The method of claim 7, wherein the SUS comprises at least one of: an SUS derived from *Arabidopsis thaliana*, an SUS derived from *Vigna radiate*.

10. The method of claim 9, wherein the SUS comprises at least one of: *Arabidopsis sucrose* synthase 1; *Arabidopsis sucrose* synthase 3; and *Vigna radiate* sucrose synthase (mbSUS1).

11. The method of claim 7, wherein the whole-cell catalyst composition comprises a second whole-cell catalyst, said second whole-cell catalyst being a *Pichia pastoris* host cell transformed to include four copies of a third nucleotide sequence encoding a UGT76G1-GCW61 fusion protein, wherein the third nucleotide sequence comprises the sequence set forth in SEQ ID NO: 4 and two copies of the second nucleotide sequence, wherein the second nucleotide sequence comprises the sequence set forth in-SEQ ID NO: 12.

12. The method of claim 7, wherein the *Pichia pastoris* host cell is transformed to include five copies of the first nucleotide sequence and two copies of the second nucleotide sequence, wherein the second nucleotide sequence comprises the sequence set forth in-SEQ ID NO: 12.

13. The method of claim 11, wherein the starting steviol glycoside substrate is stevioside and the produced steviol glycoside is rebaudioside A.

14. The method of claim 11, wherein the starting steviol glycoside substrate is rebaudioside D and the produced steviol glycoside is rebaudioside M.

15. The method of claim 11, wherein the starting steviol glycoside substrate is rebaudioside E and the produced steviol glycoside is rebaudioside D.

16. The method of claim 12, wherein the starting steviol glycoside substrate is rebaudioside A and the produced steviol glycoside is rebaudioside D.

17. The method of claim 12, wherein the starting steviol glycoside substrate is stevioside and the produced steviol glycoside is rebaudioside E.

18. The method of claim 11, wherein the starting steviol glycoside substrate comprises stevioside, rebaudioside A, or any combination thereof and the produced steviol glycoside is rebaudioside M.

19. The method of claim 12, wherein the starting steviol glycoside substrate is rebaudioside KA and the produced steviol glycoside is rebaudioside E.

20. The method of claim 12, wherein the starting steviol glycoside substrate is rubusoside and the produced steviol glycoside is rebaudioside KA.

21. The method of claim 12, wherein the starting steviol glycoside substrate is rubusoside and the produced steviol glycoside is rebaudioside E.

22. The method of claim 7, wherein the starting steviol glycoside substrate is selected from the group consisting of rubusoside, rebaudioside KA, stevioside, rebaudioside A, rebaudioside D, rebaudioside E, and any combination thereof.

23. The method of claim 7 for producing a steviol glycoside selected from the group consisting of rebaudioside KA, rebaudioside A, rebaudioside D, rebaudioside E, rebaudioside M, and any combination thereof by glycosylating a starting steviol glycoside substrate selected from the group consisting of rubusoside, rebaudioside KA, stevioside, rebaudioside A, rebaudioside D, rebaudioside E, and any combination thereof.

24. The method of claim 7, further comprising separating said desired steviol glycoside from the culture medium.

25. The whole-cell catalyst composition of claim 1, wherein the *Pichia pastoris* host cell is transformed to include more than one copy of each of said first and second nucleotide sequences.

* * * * *

SEQUENCE LISTING

<160> NUMBER OF SEQ ID NOS: 12

<210> SEQ ID NO 1
<211> LENGTH: 508
<212> TYPE: PRT
<213> ORGANISM: Artificial Sequence
<220> FEATURE:
<223> OTHER INFORMATION: Synthetic

<400> SEQUENCE: 1

```
Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
            35                  40                  45

Ile Ala Arg Leu Pro Pro Leu Arg Pro Ala Val Ala Pro Leu Val Asp
        50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
            115                 120                 125

Phe His His Trp Ala Ala Ala Ala Val Glu Asn Lys Val Pro Cys
        130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
            245                 250                 255

Glu Asp Ala Ala Val Arg Trp Leu Asp Ala Gln Pro Ala Lys Ser Val
        260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
            325                 330                 335

Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
```

```
                355                 360                 365
Pro Leu Ile Met Leu Pro Ile Ser Ser Asp Gln Gly Pro Asn Ala Arg
        370                 375                 380
Leu Met Glu Gly Arg Lys Val Gly Met Gln Val Pro Arg Asp Glu Ser
385                 390                 395                 400
Asp Gly Ser Phe Arg Arg Glu Asp Val Ala Thr Val Arg Ala Val
                405                 410                 415
Ala Val Glu Glu Asp Gly Arg Arg Val Phe Thr Ala Asn Ala Lys Lys
                420                 425                 430
Met Gln Glu Ile Val Ala Asp Gly Ala Cys His Glu Arg Cys Ile Asp
        435                 440                 445
Gly Phe Ile Gln Gln Leu Arg Ser Tyr Lys Ala Thr Arg Asn Asn Leu
        450                 455                 460
Ser Asn Glu Ser Asn Gly Thr Asn His Ser Asn His Thr Ser Ser Val
465                 470                 475                 480
Pro Thr Gly Ala Ala Val Arg Ala Ser Gly Met Gly Ala Gly Leu Leu
                485                 490                 495
Gly Ala Gly Val Val Ala Gly Val Ala Leu Leu Ile
                500                 505

<210> SEQ ID NO 2
<211> LENGTH: 1527
<212> TYPE: DNA
<213> ORGANISM: Artificial Sequence
<220> FEATURE:
<223> OTHER INFORMATION: Synthetic

<400> SEQUENCE: 2
atggatggta actcctcttc ttcccctctt cacgtcgtca tttgcccttg gcttgctctt      60
ggacacttgt tgccttgctt ggacattgca gagagattgg cttccagagg tcatagagtt     120
tcatttgtca gtaccccaag aaacattgct agacttccac cttttgagac agctgttgcc     180
cctttggttg atttcgtcgc tcttccattg cctcatgttg acggtttgcc agagggagct     240
gaatcaacaa atgatgttcc ttacgacaag tttgaacttc acagaaaggc ttttgatggt     300
ttggctgccc cattttctga gttccttaga gcagcttgtg ctgaaggtgc cggttctaga     360
ccagattggt tgattgttga acttttcat cactgggccg cagctgccgc agttgagaac     420
aaggttcctt gcgtcatgtt gcttttgggt gctgccacag ttatcgcagg tttcgctaga     480
ggagtctctg aacacgcagc tgccgcagtt ggaaaggaga ccagctgc cgaagctcct     540 tcatttgaaa ctgagagaag aaaattgatg actacacaaa atgcaagtgg tatgactgtt     600
gctgaaagat acttccttac attgatgaga tcagatttgg ttgccatcag aagttgtgca     660
gaatgggagc cagaatctgt tgcagctctt accactttgg ctggtaaacc agttgtccct     720
ttgggacttt tgccaccttc tcctgagggt ggaagaggtg tttccaagga agatgccgca     780
gtcagatggt tggacgccca accagcaaaa tcagttgtct atgttgctct tggaagtgag     840
gtccctttga gagccgagca ggttcatgaa cttgctttgg tcttgaatt gtctggagct     900 agatttcttt gggccttgag aaaaccaact gatgctcctg acgctgccgt tttgccacct     960
ggtttcgaag agagaaccag aggtagagga ttggttgtca ctggatgggt tccacaaatt    1020
ggtgtcttgg ctcatggagc cgttgcagct tcttgacac actgcggttg gaactccacc    1080
atcgagggtc ttttgttcgg acacccactt attatgttgc ctatctcttc cgatcaaggt    1140
ccaaatgcta gattgatgga aggtagaaaa gttggaatgc aggtccctag agatgagtct    1200
```

```
gacggttctt ttagaagaga agatgttgcc gcaacagtca gagcagttgc tgtcgaagag    1260
gacggtagaa gagtcttcac cgccaacgca aagaaaatgc aggaaattgt tgctgacgga    1320
gcctgtcacg aaagatgtat tgatggtttt atccagcagt tgagaagtta caaagcaacg    1380
cgtaacaacc tatcaaacga gagtaatggt actaatcact ccaaccatac ttcttccgtg    1440
ccaactggag ctgccgttcg tgcctctggt atgggagctg gcttgttggg agctggtgtt    1500
gtagccggtg ttgctctatt gatttaa                                        1527
```

<210> SEQ ID NO 3
<211> LENGTH: 507
<212> TYPE: PRT
<213> ORGANISM: Artificial Sequence
<220> FEATURE:
<223> OTHER INFORMATION: Synthetic

<400> SEQUENCE: 3

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300
```

```
Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
        340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Ser Ser Tyr Glu Ser Leu
        435                 440                 445

Glu Ser Leu Val Ser Tyr Ile Ser Ser Leu Thr Arg Asn Asn Leu Ser
450                 455                 460

Asn Glu Ser Asn Gly Thr Asn His Ser Asn His Thr Ser Ser Val Pro
465                 470                 475                 480

Thr Gly Ala Ala Val Arg Ala Ser Gly Met Gly Ala Gly Leu Leu Gly
            485                 490                 495

Ala Gly Val Val Ala Gly Val Ala Leu Leu Ile
        500                 505
```

<210> SEQ ID NO 4
<211> LENGTH: 1524
<212> TYPE: DNA
<213> ORGANISM: Artificial Sequence
<220> FEATURE:
<223> OTHER INFORMATION: Synthetic

<400> SEQUENCE: 4

```
atggagaata agaccgagac taccgtcaga agaagaagaa gaatcatttt gttcccagtt     60
cctttccaag gtcacatcaa ccctatcttg caacttgcta cgttttgta cagtaaggga    120
ttctctatca ctatcttcca tacaaacttc aataagccaa agacctctaa ttaccctcac    180
ttcacttta gattcatttt ggataacgac ccacaggatg aaagaatctc caatttgcca    240
actcatggac ctcttgctgg tatgagaatc ccaattatca cgaacacgg tgccgacgag    300
ttgagaagag aacttgagtt gcttatgttg gcctcagaag aggatgaaga ggttagttgt    360
tgatcacag acgcactttg gtactttgca caatccgttg ctgattcatt gaaccttaga    420
agattggtcc ttatgaccct ttccttgttc aattttcatg ctcacgtttc attgccacaa    480
ttcgatgaat gggatacct tgaccctgat gacaaaacta gattggaaga gcaggcttcc    540
ggtttcccaa tgttgaaggt taaggatatc aagtctgcct attccaactg caaattttg    600
aaggaaatcc ttggaaagat gattaaacag accaaggctt caagtggtgt tatctggaac    660
tcttttaagg aattggagga gtctgaactt gagactgtca ttagagagat cccagcacct    720
tctttcttga ttccacttcc taaacatttg actgcttctt cctcaagttt gcttgatcac    780
gacagaacag ttttttcaatg gttggatcaa cagccacctt cttccgtttt gtacgtctct    840
ttcggttcta cttctgaagt tgatgagaaa gacttttttgg aaattgctag aggtcttgtc    900
```

```
gattcaaagc agagtttctt gtgggttgtc agaccaggat ttgttaaagg ttctacatgg      960
gtcgaaccat tgcctgacgg tttccttgga gagagaggta gaattgttaa gtgggtccct     1020
caacaggaag ttttggcaca tggagctatc ggtgcctttt ggacacacag tggttggaac     1080
tctaccttgg aatccgtttg cgagggagtc ccaatgattt tctccgattt tggtttggac     1140
caacctctta acgctagata tatgtctgat gttttgaagg ttggagtcta tcttgaaaac     1200
ggatgggaaa gaggagagat tgctaatgcc atcagaagag ttatggtcga tgaagaggga     1260
gagtatatta gacaaaatgc agagttttg aagcagaaag cagacgtctc tttgatgaaa      1320
ggtggatcaa gttacgaatc tttggagtcc cttgtttcat atatctcttc cttgacgcgt     1380
aacaacctat caaacgagag taatggtact aatcactcca accatacttc ttccgtgcca     1440
actggagctg ccgttcgtgc ctctggtatg ggagctggct tgttgggagc tggtgttgta     1500
gccggtgttg ctctattgat ttaa                                            1524
```

<210> SEQ ID NO 5
<211> LENGTH: 47
<212> TYPE: PRT
<213> ORGANISM: Artificial Sequence
<220> FEATURE:
<223> OTHER INFORMATION: Synthetic

<400> SEQUENCE: 5

Asn Asn Leu Ser Asn Glu Ser Asn Gly Thr Asn His Ser Asn His Thr
1               5                   10                  15

Ser Ser Val Pro Thr Gly Ala Ala Val Arg Ala Ser Gly Met Gly Ala
            20                  25                  30

Gly Leu Leu Gly Ala Gly Val Val Ala Gly Val Ala Leu Leu Ile
        35                  40                  45

<210> SEQ ID NO 6
<211> LENGTH: 150
<212> TYPE: DNA
<213> ORGANISM: Artificial Sequence
<220> FEATURE:
<223> OTHER INFORMATION: Synthetic

<400> SEQUENCE: 6

```
acgcgtaaca acctatcaaa cgagagtaat ggtactaatc actccaacca tacttcttcc       60
gtgccaactg gagctgccgt tcgtgcctct ggtatgggag ctggcttgtt gggagctggt      120
gttgtagccg gtgttgctct attgatttaa                                      150
```

<210> SEQ ID NO 7
<211> LENGTH: 459
<212> TYPE: PRT
<213> ORGANISM: Artificial Sequence
<220> FEATURE:
<223> OTHER INFORMATION: Synthetic

<400> SEQUENCE: 7

Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Val Glu Asn Lys Val Pro Cys
130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255

Glu Asp Ala Ala Val Arg Trp Leu Asp Ala Gln Pro Ala Lys Ser Val
            260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
        355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
        435                 440                 445

Gly Phe Ile Gln Gln Leu Arg Ser Tyr Lys Ala
    450                 455

<210> SEQ ID NO 8
<211> LENGTH: 1377
<212> TYPE: DNA

<213> ORGANISM: Artificial Sequence
<220> FEATURE:
<223> OTHER INFORMATION: Synthetic

<400> SEQUENCE: 8

```
atggatggta actcctcttc ttcccctctt cacgtcgtca tttgcccttg gcttgctctt      60
ggacacttgt tgccttgctt ggacattgca gagagattgg cttccagagg tcatagagtt     120
tcatttgtca gtaccccaag aaacattgct agacttccac ctttgagacc agctgttgcc     180
cctttggttg atttcgtcgc tcttccattg cctcatgttg acggtttgcc agagggagct     240
gaatcaacaa atgatgttcc ttacgacaag tttgaacttc acagaaaggc ttttgatggt     300
ttggctgccc cattttctga gttccttaga gcagcttgtg ctgaaggtgc cggttctaga     360
ccagattggt tgattgttga tacttttcat cactgggccg cagctgccgc agttgagaac     420
aaggttcctt gcgtcatgtt gcttttgggt gctgccacag ttatcgcagg tttcgctaga     480
ggagtctctg aacacgcagc tgccgcagtt ggaaaggaga gaccagctgc cgaagctcct     540
tcatttgaaa ctgagagaag aaaattgatg actacacaaa atgcaagtgg tatgactgtt     600
gctgaaagat acttccttac attgatgaga tcagatttgg ttgccatcag aagttgtgca     660
gaatgggagc cagaatctgt tgcagctctt accactttgg ctggtaaacc agttgtccct     720
ttgggacttt tgccaccttc tcctgagggt ggaagaggtg tttccaagga agatgccgca     780
gtcagatggt tggacgccca accagcaaaa tcagttgtct atgttgctct ggaagtgag     840
gtcccttga gagccgagca ggttcatgaa cttgctttgg gtcttgaatt gtctggagct     900
agatttcttt gggccttgag aaaaccaact gatgctcctg acgctgccgt tttgccacct     960
ggtttcgaag agagaaccag aggtagagga ttggttgtca ctggatgggt tccacaaatt    1020
ggtgtcttgg ctcatggagc cgttgcagct ttccttgacac actgcggttg gaactccacc    1080
atcgagggtc ttttgttcgg acacccactt attatgttgc ctatctcttc cgatcaaggt    1140
ccaaatgcta gattgatgga aggtagaaaa gttggaatgc aggtccctag agatgagtct    1200
gacggttctt ttagaagaga agatgttgcc gcaacagtca gagcagttgc tgtcgaagag    1260
gacggtagaa gagtcttcac cgccaacgca aagaaaatgc aggaaattgt tgctgacgga    1320
gcctgtcacg aaagatgtat tgatggtttt atccagcagt tgagaagtta caaagca       1377
```

<210> SEQ ID NO 9
<211> LENGTH: 458
<212> TYPE: PRT
<213> ORGANISM: Artificial Sequence
<220> FEATURE:
<223> OTHER INFORMATION: Synthetic

<400> SEQUENCE: 9

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95
```

Gly Ala Asp Glu Leu Arg Arg Glu Leu Glu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
            165                 170                 175

Glu Gln Ala Ser Gly Phe Pro Met Leu Lys Val Lys Asp Ile Lys Ser
        180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser
            245                 250                 255

Leu Leu Asp His Asp Arg Thr Val Phe Gln Trp Leu Asp Gln Gln Pro
        260                 265                 270

Pro Ser Ser Val Leu Tyr Val Ser Phe Gly Ser Thr Ser Glu Val Asp
    275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
        340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Gly Glu Tyr Ile Arg Gln Asn Ala Arg Val Leu Lys Gln
        420                 425                 430

Lys Ala Asp Val Ser Leu Met Lys Gly Gly Ser Ser Tyr Glu Ser Leu
    435                 440                 445

Glu Ser Leu Val Ser Tyr Ile Ser Ser Leu
450                 455

<210> SEQ ID NO 10
<211> LENGTH: 1374
<212> TYPE: DNA
<213> ORGANISM: Artificial Sequence
<220> FEATURE:
<223> OTHER INFORMATION: Synthetic

<400> SEQUENCE: 10

```
atggagaata agaccgagac taccgtcaga agaagaagaa gaatcatttt gttcccagtt      60
cctttccaag gtcacatcaa ccctatcttg caacttgcta acgttttgta cagtaaggga     120
ttctctatca ctatcttcca tacaaacttc aataagccaa agacctctaa ttaccctcac     180
ttcacttttta gattcatttt ggataacgac ccacaggatg aaagaatctc caatttgcca     240
actcatggac tcttgctgg tatgagaatc ccaattatca acgaacacgg tgccgacgag      300
ttgagaagag aacttgagtt gcttatgttg gcctcagaag aggatgaaga ggttagttgt     360
ttgatcacag acgcactttg gtactttgca caatccgttg ctgattcatt gaaccttaga     420
agattggtcc ttatgacctc ttccttgttc aattttcatg ctcacgtttc attgccacaa     480
ttcgatgaat tgggatacct tgaccctgat gacaaaacta gattggaaga gcaggcttcc     540
ggtttcccaa tgttgaaggt taaggatatc aagtctgcct attccaactg gcaaattttg     600
aaggaaatcc ttggaaagat gattaaacag accaaggctt caagtggtgt tatctggaac     660
tcttttaagg aattggagga gtctgaactt gagactgtca ttagagagat cccagcacct     720
tctttcttga ttccacttcc taaacatttg actgcttctt cctcaagttt gcttgatcac     780
gacagaaacg ttttttcaatg gttggatcaa cagccaccttt cttccgtttt gtacgtctct     840
ttcggttcta cttctgaagt tgatgagaaa gactttttgg aaattgctag aggtcttgtc     900
gattcaaagc agagtttctt gtgggttgtc agaccaggat ttgttaaagg ttctacatgg     960
gtcgaaccat tgcctgacgg tttccttgga gagagaggta gaattgttaa gtgggtccct    1020
caacaggaag ttttggcaca tggagctatc ggtgccttt ggacacacag tggttggaac    1080
tctaccttgg aatccgtttg cgagggagtc ccaatgattt tctccgattt tggtttggac    1140
caacctctta acgctagata tatgtctgat gtttttgaagg ttggagtcta tcttgaaaac    1200
ggatgggaaa gaggagagat tgctaatgcc atcagaagag ttatggtcga tgaagaggga    1260
gagtatatta gacaaaatgc cagagttttg aagcagaaag cagacgtctc tttgatgaaa    1320
ggtggatcaa gttacgaatc tttggagtcc cttgtttcat atatctcttc cttg          1374
```

<210> SEQ ID NO 11
<211> LENGTH: 805
<212> TYPE: PRT
<213> ORGANISM: Artificial Sequence
<220> FEATURE:
<223> OTHER INFORMATION: Synthetic

<400> SEQUENCE: 11

Met Ala Thr Asp Arg Leu Thr Arg Val His Glu Leu Arg Glu Arg Leu
1               5                   10                  15

Asp Glu Thr Leu Ser Ala Asn Arg Asn Glu Ile Leu Ala Leu Leu Ser
            20                  25                  30

Arg Ile Glu Gly Lys Gly Lys Gly Ile Leu Gln His His Gln Val Ile
        35                  40                  45

Ala Glu Phe Glu Glu Ile Pro Glu Glu Ser Arg Gln Lys Leu Thr Asp
    50                  55                  60

Gly Ala Phe Gly Glu Val Leu Arg Ser Thr Gln Glu Ala Ile Val Leu
65                  70                  75                  80

Pro Pro Trp Val Ala Leu Ala Val Arg Pro Arg Gly Val Trp Glu
                85                  90                  95

Tyr Leu Arg Val Asn Val His Ala Leu Val Val Glu Val Leu Gln Pro
            100                 105                 110

Ala Glu Tyr Leu Arg Phe Lys Glu Glu Leu Val Asp Gly Ser Ser Asn

```
                 115                 120                 125
Gly Asn Phe Val Leu Glu Leu Asp Phe Glu Pro Phe Thr Ala Ser Phe
            130                 135                 140
Pro Arg Pro Thr Leu Asn Lys Ser Ile Gly Asn Gly Val Gln Phe Leu
145                 150                 155                 160
Asn Arg His Leu Ser Ala Lys Leu Phe His Asp Lys Glu Ser Leu His
                165                 170                 175
Pro Leu Leu Glu Phe Leu Arg Leu His Ser Val Lys Gly Lys Thr Leu
            180                 185                 190
Met Leu Asn Asp Arg Ile Gln Asn Pro Asp Ala Leu Gln His Val Leu
        195                 200                 205
Arg Lys Ala Glu Glu Tyr Leu Gly Thr Val Pro Pro Glu Thr Pro Tyr
        210                 215                 220
Ser Ala Phe Glu His Lys Phe Gln Glu Ile Gly Leu Glu Arg Gly Trp
225                 230                 235                 240
Gly Asp Asn Ala Glu Arg Val Leu Glu Ser Ile Gln Leu Leu Leu Asp
                245                 250                 255
Leu Leu Glu Ala Pro Asp Pro Cys Thr Leu Glu Thr Phe Leu Gly Arg
            260                 265                 270
Ile Pro Met Val Phe Asn Val Ile Leu Ser Pro His Gly Tyr Phe
        275                 280                 285
Ala Gln Asp Asn Val Leu Gly Tyr Pro Asp Thr Gly Gly Gln Val Val
        290                 295                 300
Tyr Ile Leu Asp Gln Val Arg Ala Leu Glu Asn Glu Met Leu His Arg
305                 310                 315                 320
Ile Lys Gln Gln Gly Leu Asp Ile Val Pro Arg Ile Leu Ile Ile Thr
                325                 330                 335
Arg Leu Leu Pro Asp Ala Val Gly Thr Thr Cys Gly Gln Arg Leu Glu
            340                 345                 350
Lys Val Phe Gly Thr Glu His Ser His Ile Leu Arg Val Pro Phe Arg
        355                 360                 365
Thr Glu Asn Gly Ile Val Arg Lys Trp Ile Ser Arg Phe Glu Val Trp
    370                 375                 380
Pro Tyr Leu Glu Thr Tyr Thr Glu Asp Val Ala His Glu Leu Ala Lys
385                 390                 395                 400
Glu Leu Gln Gly Lys Pro Asp Leu Ile Val Gly Asn Tyr Ser Asp Gly
                405                 410                 415
Asn Ile Val Ala Ser Leu Leu Ala His Lys Leu Gly Val Thr Gln Cys
            420                 425                 430
Thr Ile Ala His Ala Leu Glu Lys Thr Lys Tyr Pro Glu Ser Asp Ile
        435                 440                 445
Tyr Trp Lys Lys Leu Glu Glu Arg Tyr His Phe Ser Cys Gln Phe Thr
    450                 455                 460
Ala Asp Leu Phe Ala Met Asn His Thr Asp Phe Ile Ile Thr Ser Thr
465                 470                 475                 480
Phe Gln Glu Ile Ala Gly Ser Lys Asp Thr Val Gly Gln Tyr Glu Ser
                485                 490                 495
His Thr Ala Phe Thr Leu Pro Gly Leu Tyr Arg Val Val His Gly Ile
            500                 505                 510
Asp Val Phe Asp Pro Lys Phe Asn Ile Val Ser Pro Gly Ala Asp Gln
        515                 520                 525
Thr Ile Tyr Phe Pro His Thr Glu Thr Ser Arg Arg Leu Thr Ser Phe
    530                 535                 540
```

His Thr Glu Ile Glu Glu Leu Leu Tyr Ser Ser Val Glu Asn Glu Glu
545                 550                 555                 560

His Ile Cys Val Leu Lys Asp Arg Ser Lys Pro Ile Ile Phe Thr Met
            565                 570                 575

Ala Arg Leu Asp Arg Val Lys Asn Ile Thr Gly Leu Val Glu Trp Tyr
        580                 585                 590

Gly Lys Asn Ala Lys Leu Arg Glu Leu Val Asn Leu Val Val Ala
    595                 600                 605

Gly Asp Arg Arg Lys Glu Ser Lys Asp Leu Glu Glu Lys Ala Glu Met
610                 615                 620

Lys Lys Met Tyr Ser Leu Ile Glu Thr Tyr Lys Leu Asn Gly Gln Phe
625                 630                 635                 640

Arg Trp Ile Ser Ser Gln Met Asn Arg Val Arg Asn Gly Glu Leu Tyr
                645                 650                 655

Arg Val Ile Ala Asp Thr Lys Gly Ala Phe Val Gln Pro Ala Val Tyr
            660                 665                 670

Glu Ala Phe Gly Leu Thr Val Val Glu Ala Met Thr Cys Gly Leu Pro
        675                 680                 685

Thr Phe Ala Thr Cys Asn Gly Gly Pro Ala Glu Ile Ile Val His Gly
    690                 695                 700

Lys Ser Gly Phe His Ile Asp Pro Tyr His Gly Asp Arg Ala Ala Asp
705                 710                 715                 720

Leu Leu Val Glu Phe Phe Glu Lys Val Lys Val Asp Pro Ser His Trp
                725                 730                 735

Asp Lys Ile Ser Gln Ala Gly Leu Gln Arg Ile Glu Glu Lys Tyr Thr
            740                 745                 750

Trp Gln Ile Tyr Ser Gln Arg Leu Leu Thr Leu Thr Gly Val Tyr Gly
        755                 760                 765

Phe Trp Lys His Val Ser Asn Leu Asp Arg Arg Glu Ser Arg Arg Tyr
    770                 775                 780

Leu Glu Met Phe Tyr Ala Leu Lys Tyr Arg Lys Leu Ala Glu Ser Val
785                 790                 795                 800

Pro Leu Ala Val Glu
            805

<210> SEQ ID NO 12
<211> LENGTH: 2418
<212> TYPE: DNA
<213> ORGANISM: Artificial Sequence
<220> FEATURE:
<223> OTHER INFORMATION: Synthetic

<400> SEQUENCE: 12
atggctactg acagattgac tagagttcac gaattgagag aaagattgga cgaaaccttg      60
tctgctaata gaaacgagat tttggccttg ttgtctagaa ttgaaggaaa gggtaagggt     120
attttgcaac accatcaggt tattgcagag ttcgaggaaa tcccagaaga gtctagacag     180
aagttgactg atggagcttt cggagaagtc ttgagatcca ctcaagaggc tattgtcttg     240
ccaccatggg ttgccttggc agtcagacca agacctggtg tctggaata cttgagagtt     300 aatgtccatg ctttggttgt tgaggttttg cagcctgccg agtatttgag atttaaggaa     360
gagttggttg atggatcttc taacggtaat ttcgtcttgg agttggattt cgagcctttt     420
actgcctctt ttcctagacc aacattgaat aagtctatcg gtaatggtgt ccagttttg      480 aacagacatt tgtctgccaa attgtttcat gataaggaat ctttgcatcc attgttggag     540

-continued

```
ttcttgagat tgcattctgt taagggaaaa actttgatgt tgaacgatag aatccaaaac    600
ccagacgcat tgcagcatgt tttgagaaag gctgaagagt acttgggaac agttccacca    660
gaaacacctt actctgcatt cgagcataag ttccaggaaa tcggattgga gagaggttgg    720
ggtgataacg ctgagagagt tttggaatct attcagttgt tgttggactt gttggaggcc    780
ccagacccat gtactttgga gactttcttg ggtagaatcc ctatggtttt caacgtcgtt    840
atcttgtctc cacatggtta ctttgctcag gataacgttt tgggttaccc tgacactgga    900
ggtcaagtcg tttacatttt ggatcaagtt agagccttgg agaacgaaat gttgcacaga    960
attaaacaac agggtttgga tattgttcca agaatcttga ttattactag attgttgcct   1020
gacgccgttg gaactacttg tggtcagaga ttggaaaaag tcttcggtac agaacactct   1080
catattttga gagtcccatt tagaactgaa aacggtattg ttagaaagtg gatctctaga   1140
ttcgaggttt ggccatactt ggaaacttat acagaggatg ttgctcatga attggctaag   1200
gagttgcagg gaaagccaga tttgatcgtt ggtaactact ctgacggaaa tatcgtcgct   1260
tctttgttgg cccacaaatt gggtgttact caatgtacta ttgctcacgc attggaaaag   1320
acaaagtacc cagaatctga tatttactgg aaaaagttgg aagagagata ccacttctct   1380
tgtcagttta cagctgattt gtttgctatg aaccatactg atttcattat tacttctact   1440
tttcaggaaa tcgcaggttc taaggatact gttggtcaat acgaatctca cacagcattc   1500
actttgccag gtttgtatag agttgttcac ggaatcgatg tttttgatcc aaagtttaac   1560
attgtttctc caggagctga tcaaactatc tatttcccac ataccgagac ctctagaaga   1620
ttgacttctt tccacacaga gattgaggaa ttgttgtatt cttctgttga aaacgaggaa   1680
cacatttgtg ttttgaaaga cagatccaag cctatcattt tcactatggc tagattggat   1740
agagtcaaga acatcactgg tttggtcgaa tggtacggta agaatgctaa gttgagagaa   1800
ttggttaact tggtcgttgt tgccggtgat agaagaaagg aatctaaaga cttggaggaa   1860
aaggctgaaa tgaagaagat gtactctttg attgaaactt acaaattgaa cggtcaattc   1920
agatggatct cttctcagat gaacagagtc agaaacggtg aattgtacag agttattgct   1980
gatactaagg gtgcatttgt tcaaccagca gtctacgaag ctttcggttt gactgttgtt   2040
gaagctatga cttgtggttt gcctacattt gcaacttgta atggtggacc agctgagatc   2100
atcgttcatg gaaagtctgg ttttcatatt gatccttacc atggagatag agctgcagac   2160
ttgttggttg agttcttcga gaaggttaag gttgacccat ctcattggga taagatttct   2220
caagctggat tgcaaagaat tgaagaaaaa tacacttggc aaatttactc tcaaagattg   2280
ttgacattga ctggagttta tggtttctgg aagcatgttt ctaatttgga cagaagagaa   2340
tctagaagat acttggaaat gttttacgct ttgaaatata gaaaattggc cgagtctgtt   2400
ccattggctg ttgagtaa                                                  2418
```